(12) United States Patent
Shiloh et al.

(10) Patent No.: US 6,211,336 B1
(45) Date of Patent: Apr. 3, 2001

(54) ATAXIA-TELANGIECTASIA GENE

(75) Inventors: Yosef Shiloh, Tel Aviv (IL); Danilo A. Tagle, Gaithersburg; Francis Collins, Rockville, both of MD (US)

(73) Assignees: The United States of America as represented by the Department of Health and Human Services, Washington, DC (US); Ramot University Authority for Applied Research and Industrial Dev. (IL)

( * ) Notice: Subject to any disclaimer, the term of this patent is extended or adjusted under 35 U.S.C. 154(b) by 0 days.

(21) Appl. No.: 08/952,127

(22) PCT Filed: May 16, 1996

(86) PCT No.: PCT/US96/07040

§ 371 Date: Feb. 26, 1998

§ 102(e) Date: Feb. 26, 1998

(87) PCT Pub. No.: WO96/36695

PCT Pub. Date: Nov. 21, 1996

Related U.S. Application Data

(63) Continuation-in-part of application No. 08/508,836, filed on Jul. 28, 1995, now Pat. No. 5,777,093, which is a continuation-in-part of application No. 08/493,092, filed on Jun. 21, 1995, now Pat. No. 5,728,807, which is a continuation-in-part of application No. 08/441,822, filed on May 16, 1995, now Pat. No. 5,756,288.

(51) Int. Cl.[7] .............................. C07K 1/00; C07K 14/00; C07K 17/00

(52) U.S. Cl. ............................................ 530/350; 530/326

(58) Field of Search ...................................... 530/326, 350

(56) References Cited

U.S. PATENT DOCUMENTS

| | | | |
|---|---|---|---|
| 4,666,828 | 5/1987 | Gusella | 435/6 |
| 4,683,202 | 7/1987 | Mullis | 435/91 |
| 4,801,531 | 1/1989 | Frossard | 435/6 |
| 5,192,659 | 3/1993 | Simons | 435/6 |
| 5,272,057 | 12/1993 | Smulson | 435/6 |
| 5,395,767 | 3/1995 | Murname | 435/320.1 |
| 5,464,764 | 11/1995 | Capecchi | 435/172.3 |
| 5,487,992 | 1/1996 | Capecchi | 435/172.3 |
| 5,728,807 * | 3/1998 | Shiloh et al. | 530/350 |
| 5,756,288 * | 5/1998 | Shiloh | 435/6 |
| 5,777,093 * | 7/1998 | Shiloh et al. | 536/23.5 |
| 5,858,661 * | 1/1999 | Shiloh | 435/6 |

OTHER PUBLICATIONS

Aicardi et al., "Ataxia–ocularmotor apraxia: A syndrome mimicking ataxia–telangiectasia" *Ann. Neurol.* 24:497–502 (1988).

Anderson and Kunkel, "The molecular and biochemical basis of Duchenne muscular dystrophy" *Trends Biochem. Sci.* 17:289–292 (1992).

Ballabio et al., "Molecular heterogeneity of steroid sulfatase deficiency: a multicenter study on 57 unrelated patients, at DNA and protein levels" *Genomics* 4:36–40 (1989).

Beaudet and Tsui, "A suggested nomenclature for designating mutations" *Hum. Mutat.* 2:245–248 (1993).

Blunt et al., 1995. Defective DNA–dependent protein kinase activity is linked to V(D)J recombination and DNA repair defects associated with the murine scid mutation. Cell 80:813–823.

Bosma and Carroll, 1991. The SCID mouse mutant: definition, characterization, and potential uses. Rev. Immunol. 9:323–350. [n/a—will mail in].

Boyle et al., 1992. Rapid physical mapping of cloned DNA on banded mouse chromosomes by fluorescence in situ hybridization. Genomics 12:106–115.

Broughton et al., "Mutations in the xeroderma pigmentosum group D DNA repair/transcription gene in patients with trichothiodystrophy" *Nature Genet.* 7:189–194 (1994).

Broughton et al., "Molecular and cellular analysis of the DNA repair defect in a patient in xeroderma pigmentosum group D who has the clinical features of xeroderma pigmentosum and Cockayne's syndrome" *Am. J. Hum. Genet.* 56:167–174 (1995).

Brown et al., "Control of p70 S6 kinase by kinase activity of FRAP in vivo" Nature 377:441–446 (1995).

Byrne et al., "Ataxia–without–telangiectasia" *J Neurol. Sci.* 66:307–317 (1984).

Chessa et al., "Heterogeneity in ataxia telangiectasia: classical phenotype associated with intermediate cellular radiosensitivity" *Am. J. Med. Genet.* 42:741–746 (1992).

Chillon et al., "Mutations in the cystic fibrosis gene in patients with congenital absence of the vas deferens" *New Engl. J. Med.* 332:1475–1480 (1995).

Copeland and Jenkins, 1991. Development and applications of a molecular genetic linkage map of the mouse genome. Trends Genet. 7:113–118.

Copeland et al., 1993. A genetic linkage map of the mouse: current applications and future prospects. Science 262:57–66.

Derry et al., "WASP gene mutations in Wiskott–Aldrich syndrome and X–linked thrombocytopenia" *Hum. Mol. Genet.* 4:1127–1135 (1995).

Dietz and Kendzior, "Maintenance of an open reading frame as an additional level of scrutiny during splice site selection" *Nature Genet.* 8:183–188 (1994).

Fiorilli et al., "Variant of ataxia–telangiectasia with low–level radiosensitivity" *Hum. Genet.* 70:274–277 (1985).

(List continued on next page.)

Primary Examiner—Marianne M. Cintins
Assistant Examiner—C. Delacroix-Muirheid
(74) Attorney, Agent, or Firm—Kohn & Associates

(57) ABSTRACT

There is provided a purified amino acid sequence selected from the group of Sequence ID No.: 3 and analogs thereof and mutations of Sequence ID No.: 3 which cause ataxia-telangiectasia. Also provided is a purified amino acid sequence as set forth in Sequence ID No.: 3 and analogs thereof.

5 Claims, 4 Drawing Sheets

OTHER PUBLICATIONS

Fodor et al, "Multiplexed biochemical assays with biological chips", *Nature* 364:555–556 (1993).

Friedman and Weitberg, "Ataxia without telangiectasia" *Movement Disorders* 8:223–226 (1993).

Fukao et al., 1990. Molecular cloning and sequence of the complementary DNA encoding human mitochondrial acetoacrtyl–coenzyme A thiolase and study of the variant enzymes in cultured fibroblasts from patients with 3–ketothiolase deficiency. J. Clin. Inves. 86:2086–2092.

Gibson et al., "A nonsense mutation and exon skipping in the Fanconi anaemia group C gene" *Hum. Mol. Genet.* 2:797–799 (1993).

Gottlieb and Jackson, "Protein kinases and DNA damage" *Trends Biochem. Sci.* 19:500–503 (1994).

Greenwell et al., "TEL1, a gene involved in controlling telomere length in *Saccharomyces cerevisiae,* is homologous to the human ataxia telangiectasia (ATM) gene" Cell 82:823–829 (1995).

Harding, "Clinical features and classification of inherited ataxias" *Adv. Neurol.* 61:1–14 (1993).

Harnden, "The nature of ataxia–telangiectasia: problems and perspectives" *Int. J. Radiat. Biol.* 66:S13–S19 (1994).

Hartley et al., 1995. DNA–dependent protein kinase catalytic subunit: a relative of phosphatidylinositol 3–kinase and the ataxia telangiectasia gene product. Cell 82:849–856.

Jarvi et al., "Cystic fibrosis transmembrane conductance regulator and obstructive azzospermia" *The Lancet* 345:1578 (1995).

Jaspers et al., "Genetic complementation analysis of Ataxia–Telangiectasia and Nijmegen breakage syndrome: A survey of 50 patients", *Cytogenet. Cell Genet.,* 49:259–263 (1988).

Jenkins et al., 1982. "Organization, distribution and stability of endogenous ecotropic murine leukemia virus DNA sequences in chromosomes of *Mus musculus*" . J. Virol. 43:26–36.

Kingsley et al., 1989. A molecular genetic linkage map of mouse chromosome 9 with new regional localizations for Gsta, T3g, Ets–1, and Ldlr loci. Genetics 123:165–172.

Kolluri et al., "Identification of WASP mutations in patients with Wiskott–Aldrich syndrome and isolated thrombocytopenia reveals allelic heterogeneity at the WAS locus" *Hum. Mol. Genet.* 4:1119–1126 (1995).

Liu and Sommer, "Restriction endonuclease fingerprinting (REF): a sensitive method for screening mutations in long, contiguous segments of DNA" *BioTechniques* 18:470–477 (1995).

Maserati et al., "Ataxia–without–telangiectasia in two sisters with rearrangements of chromosomes 7 and 14" *Clin. Genet.* 34:283–287 (1988).

Nadeau and Taylor 1984. Lengths of chromosomal segments conserved since divergence of man and mouse. Proc. Natl. Acad. Sci. USA 81:814–818.

Regnier et al., 1989. Identification of two murine loci homologous to the v–cbl oncogene. J. Virol. 63:3678–3682.

Richard et al., "A radiation hybrid map of human chromosme 11q22–23 containing the Ataxia–Telangiectasia disease locus", *Genomics* 17, 1–5 (1993).

Ried et al., 1992. Simultaneous visualization of seven different DNA probes using combinatorial labeling and digital imaging microscopy. Proc. Natl. Acad. Sci. USA 89:1388–1392.

Rotman et al., "Rapid identification of polymorphic CA–repeats in YAC clones" *Molecular Biotechnology* (1995).

Savitsky et al., "The complete sequence of the coding region of the ATM gene reveals similarity to cell cycle regulators in different species" *Hum. Mol. Genet.* 4:2025–2032 (1995b).

Sommer, "Recent human germ–line mutation: Inferences from patients with hemophilia B" *Trends Gene.* 11:141–147 (1995).

Steingrimsdottir et al., "Mutations which alter splicing in the human hypoxanthine–guanine phosphoribosyl–transferase gene" *Nucleic Acids Res.* 6:1201–1208 (1992).

Szpirer et al., 1994. The genes encoding the glutamate receptor subunits KA1 and KA2 (GRIK4 and GRIK5) are located on separate chromosomes in human, mouse and rat. Proc. Natl. Acad. Sci. USA 91:11849–11853.

Taylor et al., "Genetic and cellular features of ataxia telangiectasia" *Int. J. Radiat. Biol.* 65:65–70 (1994).

Taylor et al., Variant forms of ataxia telangiectasia. J. Med. Genet. 24, 669–677 (1987).

Thomas et al., 1991. Phosphorylation of c–Src on tyrosine 527 by anchor protein tyrosine kinase. Science 254:568–571.

Weemaes et al., "Nijmegen breakage syndrome: A progress report" *Int. J. Radiat. Biol.* 66:S185–S188 (1994).

Ying and Decoteau, "Cytogenetic anomalies in a patient with ataxia, immune deficiency, and high alpha–fetoprotein in the absence of telangiectasia" *Cancer Genet. Cytogenet.* 4:311–317 (1983).

Zakian, "ATM–related genes: What do they tell us about functions of the human gene?" *Cell* 82:685–687 (1995).

Ziv et al., "Ataxia telangiectasia: a variant with altered in vitro phenotype of fibroblast cells" *Mutation Res.* 210:211–219 (1989).

* cited by examiner

```
2708 LPKIIDCVGSDGKERRQLVKGRDDLRQDAVMQQVFQMCNTLLQRNTETRK 2757
     |||||||||||||||||||||||||||||||||||||||||||||||||
2698 LPKIIDCVGSDGKERRQLVKGRDDLRQDAVMQQVFQMCNTLLQRNTETRK 2747

2758 RKLTICTYKVVPLSQRSGVLEWCTGTVPIGEYLVNSEDGAHRRYRPNDFS 2807
     ||||||||||||||||||||||||||||||:||.|||.||||:||||||
2748 RKLTICTYKVVPLSQRSGVLEWCTGTVPIGEFLVNNEDGAHKRYRPNDFS 2797

2808 ANQCQKKMMEVQKKSFEEKYDTFMTICQNFEPVFRYFCMEKFLDPAVWFE 2857
     |.|||||||||||||||||:||.||:|:|.||||||||||||||||:||
2798 AFQCQKKMMEVQKKSFEEKYEVFMDVCQNFQPVFRYFCMEKFLDPAIWFE 2847

2858 KRLAYTRSVATSSIVGYILGLGDRHVQNILINEQSAELVHIDLGVAFEQG 2907
     |||||||||||||||||||||||||||||||||||||||||||||||||
2848 KRLAYTRSVATSSIVGYILGLGDRHVQNILINEQSAELVHIDLGVAFEQG 2897

2908 KILPTPETVPFRLSRDIVDGMGITGVEGVFRRCCEKTMEVMRSSQETLLT 2957
     |||||||||||||.||||||||||||||||||||||||||||.||||||
2898 KILPTPETVPFRLTRDIVDGMGITGVEGVFRRCCEKTMEVMRNSQETLLT 2947

2958 IVEVLLYDPLFDWTMNPLKALYLQQRPEDESDLHSTPNADDQECKQSLSD 3007
     |||||||||||||||||||||||||||.||:.|||||||||||:...||
2948 IVEVLLYDPLFDWTMNPLKALYLQQRPEDETELHPTLNADDQECKRNLSD 2997

3008 TDQSFNKVAERVLMRLQEKLKGVEEGTVLSVGGQVNLLIQQAMDPKNLSR 3057
     .|||:|||||||||||||||||||||||||||||||||||||:|||||| 
2998 IDQSFDKVAERVLMRLQEKLKGVEEGTVLSVGGQVNLLIQQAIDPKNLSR 3047

3058 LFPGWKAWV 3066
     |||||||||
3048 LFPGWKAWV 3056
```

Fig-4

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 5912 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (B) CLONE: 7-9

(xi) SEQUENCE DESCRIPTION: SEQ ID NO:1:

```
CATACTTTTT CCTCTTAGTC TACAGGTTGG CTGCATAGAA GAAAAAGGTA GAGTTATTTA      60
TAATCTTGTA AATCTTGGAC TTTGAGTCAT CTATTTTCTT TTACAGTCAT CGAATACTTT     120
TGGAAATAAG GTAATATATG CCTTTTGAGC TGTCTTGACG TTCACAGATA TAAAATATTA     180
AATATATTTT AATTTTGTGC CCTTGCAGAT TGATCACTTA TTCATTAGTA ATTTACCAGA     240
GATTGTGGTG GAGTTATTGA TGACGTTACA TGAGCCAGCA AATTCTAGTG CCAGTCAGAG     300
CACTGACCTC TGTGACTTTT CAGGGGATTT GGATCCTGCT CCTAATCCAC CTCATTTTCC     360
ATCGCATGTG ATTAAAGCAA CATTTGCCTA TATCAGCAAT TGTCATAAAA CCAAGTTAAA     420
AAGCATTTTA GAAATTCTTT CCAAAAGCCC TGATTCCTAT CAGAAAATTC TTCTTGCCAT     480
ATGTGAGCAA GCAGCTGAAA CAAATAATGT TTATAAGAAG CACAGAATTC TTAAAATATA     540
TCACCTGTTT GTTAGTTTAT TACTGAAAGA TATAAAAAGT GGCTTAGGAG GAGCTTGGGC     600
CTTTGTTCTT CGAGACGTTA TTTATACTTT GATTCACTAT ATCAACCAAA GGCCTTCTTG     660
TATCATGGAT GTGTCATTAC GTAGCTTCTC CCTTTGTTGT GACTTATTAA GTCAGGTTTG     720
CCAGACAGCC GTGACTTACT GTAAGGATGC TCTAGAAAAC CATCTTCATG TTATTGTTGG     780
TACACTTATA CCCCTTGTGT ATGAGCAGGT GGAGGTTCAG AAACAGGTAT GGACTTGTT     840
GAAATACTTA GTGATAGATA ACAAGGATAA TGAAAACCTC TATATCACGA TTAAGCTTTT     900
AGATCCTTTT CCTGACCATG TTGTTTTTAA GGATTTGCGT ATTACTCAGC AAAAAATCAA     960
ATACAGTAGA GGACCCTTTT CACTCTTGGA GGAAATTAAC CATTTTCTCT CAGTAAGTGT    1020
TTATGATGCA CTTCCATTGA CAAGACTTGA AGGACTAAAG GATCTTCGAA GACAACTGGA    1080
ACTACATAAA GATCAGATGG TGGACATTAT GAGAGCTTCT CAGGATAATC CGCAAGATGG    1140
GATTATGGTG AAACTAGTTG TCAATTTGTT GCAGTTATCC AAGATGGCAA TAAACCACAC    1200
TGGTGAAAAA GAAGTTCTAG AGGCTGTTGG AAGCTGCTTG GGAGAAGTGG GTCCTATAGA    1260
TTTCTCTACC ATAGCTATAC AACATAGTAA AGATGCATCT TATACCAAGG CCCTTAAGTT    1320
ATTTGAAGAT AAAGAACTTC AGTGGACCTT CATAATGCTG ACCTACCTGA ATAACACACT    1380
GGTAGAAGAT TGTGTCAAAG TTCGATCAGC AGCTGTTACC TGTTTGAAAA ACATTTTAGC    1440
CACAAAGACT GGACATAGTT TCTGGGAGAT TTATAAGATG ACAACAGATC CAATGCTGGC    1500
CTATCTACAG CCTTTTAGAA CATCAAGAAA AAAGTTTTTA GAAGTACCCA GATTTGACAA    1560
AGAAAACCCT TTTGAAGGCC TGGATGATAT AAATCTGTGG ATTCCTCTAA GTGAAAATCA    1620
TGACATTTGG ATAAAGACAC TGACTTGTGC TTTTTTGGAC AGTGGAGGCA CAAAATGTGA    1680
```

-continued

```
AATTCTTCAA TTATTAAAGC CAATGTGTGA AGTGAAAACT GACTTTTGTC AGACTGTACT    1740

TCCATACTTG ATTCATGATA TTTTACTCCA AGATACAAAT GAATCATGGA GAAATCTGCT    1800

TTCTACACAT GTTCAGGGAT TTTTCACCAG CTGTCTTCGA CACTTCTCGC AAACGAGCCG    1860

ATCCACAACC CCTGCAAACT TGGATTCAGA GTCAGAGCAC TTTTTCCGAT GCTGTTTGGA    1920

TAAAAAATCA CAAAGAACAA TGCTTGCTGT TGTGGACTAC ATGAGAAGAC AAAAGAGACC    1980

TTCTTCAGGA ACAATTTTTA ATGATGCTTT CTGGCTGGAT TTAAATTATC TAGAAGTTGC    2040

CAAGGTAGCT CAGTCTTGTG CTGCTCACTT TACAGCTTTA CTCTATGCAG AAATCTATGC    2100

AGATAAGAAA AGTATGGATG ATCAAGAGAA AGAAGTCTT GCATTTGAAG AAGGAAGCCA    2160

GAGTACAACT ATTTCTAGCT TGAGTGAAAA AGTAAAGAA GAAACTGGAA TAAGTTTACA    2220

GGATCTTCTC TTAGAAATCT ACAGAAGTAT AGGGGAGCCA GATAGTTTGT ATGGCTGTGG    2280

TGGAGGGAAG ATGTTACAAC CCATTACTAG ACTACGAACA TATGAACACG AAGCAATGTG    2340

GGGCAAAGCC CTAGTAACAT ATGACCTCGA ACAGCAATC CCCTCATCAA CACGCCAGGC     2400

AGGAATCATT CAGGCCTTGC AGAATTTGGG ACTCTGCCAT ATTCTTTCCG TCTATTTAAA    2460

AGGATTGGAT TATGAAAATA AAGACTGGTG TCCTGAACTA AAGAACTTC ATTACCAAGC     2520

AGCATGGAGG AATATGCAGT GGGACCATTG CACTTCCGTC AGCAAAGAAG TAGAAGGAAC    2580

CAGTTACCAT GAATCATTGT ACAATGCTCT ACAATCTCTA AGAGACAGAG AATTCTCTAC    2640

ATTTTATGAA AGTCTCAAAT ATGCCAGAGT AAAAGAAGTG GAAGAGATGT GTAAGCGCAG    2700

CCTTGAGTCT GTGTATTCGC TCTATCCCAC ACTTAGCAGG TTGCAGGCCA TTGGAGAGCT    2760

GGAAAGCATT GGGGAGCTTT TCTCAAGATC AGTCACACAT AGACAACTCT CTGAAGTATA    2820

TATTAAGTGG CAGAAACACT CCCAGCTTCT CAAGGACAGT GATTTTAGTT TTCAGGAGCC    2880

TATCATGGCT CTACGCACAG TCATTTTGGA GATCCTGATG GAAAAGGAAA TGGACAACTC    2940

ACAAAGAGAA TGTATTAAGG ACATTCTCAC CAAACACCTT GTAGAACTCT CTATACTGGC    3000

CAGAACTTTC AAGAACACTC AGCTCCCTGA AGGGCAATA TTTCAAATTA AACAGTACAA     3060

TTCAGTTAGC TGTGGAGTCT CTGAGTGGCA GCTGGAAGAA GCACAAGTAT TCTGGGCAAA    3120

AAAGGAGCAG AGTCTTGCCC TGAGTATTCT CAAGCAAATG ATCAAGAAGT GGATGCCAG    3180

CTGTGCAGCG AACAATCCCA GCCTAAAACT TACATACACA GAATGTCTGA GGGTTTGTGG    3240

CAACTGGTTA GCAGAAACGT GCTTAGAAAA TCCTGCGGTC ATCATGCAGA CCTATCTAGA    3300

AAAGGCAGTA GAAGTTGCTG AAATTATGA TGGAGAAAGT AGTGATGAGC TAAGAAATGG     3360

AAAAATGAAG GCATTTCTCT CATTAGCCCG GTTTTCAGAT ACTCAATACC AAAGAATTGA    3420

AAACTACATG AAATCATCGG AATTTGAAAA CAAGCAAGCT CTCCTGAAAA GAGCCAAAGA    3480

GGAAGTAGGT CTCCTTAGGG AACATAAAAT TCAGACAAAC AGATACACAG TAAAGGTTCA    3540

GCGAGAGCTG GAGTTGGATG AATTAGCCCT GCGTGCACTG AAAGAGGATC GTAAACGCTT    3600

CTTATGTAAA GCAGTTGAAA ATTATATCAA CTGCTTATTA AGTGGAGAAG AACATGATAT    3660

GTGGGTATTC CGACTTTGTT CCCTCTGGCT TGAAAATTCT GGAGTTTCTG AAGTCAATGG    3720

CATGATGAAG AGAGACGGAA TGAAGATTCC AACATATAAA TTTTTGCCTC TTATGTACCA    3780

ATTGGCTGCT AGAATGGGGA CCAAGATGAT GGGAGGCCTA GGATTTCATG AAGTCCTCAA    3840

TAATCTAATC TCTAGAATTT CAATGGATCA CCCCCATCAC ACTTTGTTTA TTATACTGGC    3900

CTTAGCAAAT GCAAACAGAG ATGAATTTCT GACTAAACCA GAGGTAGCCA GAAGAAGCAG    3960

AATAACTAAA AATGTGCCTA AACAAAGCTC TCAGCTTGAT GAGGATCGAA CAGAGGCTGC    4020

AAATAGAATA ATATGTACTA TCAGAAGTAG GAGACCTCAG ATGGTCAGAA GTGTTGAGGC    4080
```

```
ACTTTGTGAT GCTTATATTA TATTAGCAAA CTTAGATGCC ACTCAGTGGA AGACTCAGAG    4140

AAAAGGCATA AATATTCCAG CAGACCAGCC AATTACTAAA CTTAAGAATT TAGAAGATGT    4200

TGTTGTCCCT ACTATGGAAA TTAAGGTGGA CCACACAGGA GAATATGGAA ATCTGGTGAC    4260

TATACAGTCA TTTAAAGCAG AATTTCGCTT AGCAGGAGGT GTAAATTTAC CAAAAATAAT    4320

AGATTGTGTA GGTTCCGATG GCAAGGAGAG GAGACAGCTT GTTAAGGGCC GTGATGACCT    4380

GAGACAAGAT GCTGTCATGC AACAGGTCTT CCAGATGTGT AATACATTAC TGCAGAGAAA    4440

CACGGAAACT AGGAAGAGGA AATTAACTAT CTGTACTTAT AAGGTGGTTC CCCTCTCTCA    4500

GCGAAGTGGT GTTCTTGAAT GGTGCACAGG AACTGTCCCC ATTGGTGAAT TTCTTGTTAA    4560

CAATGAAGAT GGTGCTCATA AAAGATACAG GCCAAATGAT TTCAGTGCCT TTCAGTGCCA    4620

AAAGAAAATG ATGGAGGTGC AAAAAAAGTC TTTTGAAGAG AAATATGAAG TCTTCATGGA    4680

TGTTTGCCAA AATTTTCAAC CAGTTTTCCG TTACTTCTGC ATGGAAAAAT TCTTGGATCC    4740

AGCTATTTGG TTTGAGAAGC GATTGGCTTA TACGCGCAGT GTAGCTACTT CTTCTATTGT    4800

TGGTTACATA CTTGGACTTG GTGATAGACA TGTACAGAAT ATCTTGATAA ATGAGCAGTC    4860

AGCAGAACTT GTACATATAG ATCTAGGTGT TGCTTTTGAA CAGGGCAAAA TCCTTCCTAC    4920

TCCTGAGACA GTTCCTTTTA GACTCACCAG AGATATTGTG GATGGCATGG GCATTACGGG    4980

TGTTGAAGGT GTCTTCAGAA GATGCTGTGA GAAAACCATG GAAGTGATGA GAAACTCTCA    5040

GGAAACTCTG TTAACCATTG TAGAGGTCCT TCTATATGAT CCACTCTTTG ACTGGACCAT    5100

GAATCCTTTG AAAGCTTTGT ATTTACAGCA GAGGCCGGAA GATGAAACTG AGCTTCACCC    5160

TACTCTGAAT GCAGATGACC AAGAATGCAA ACGAAATCTC AGTGATATTG ACCAGAGTTT    5220

CGACAAAGTA GCTGAACGTG TCTTAATGAG ACTACAAGAG AAACTGAAAG GAGTGGAAGA    5280

AGGCACTGTG CTCAGTGTTG GTGGACAGGT GAATTTGCTC ATACAGCAGG CCATAGACCC    5340

CAAAAATCTC AGCCGACTTT TCCCAGGATG GAAAGCTTGG GTGTGATCTT CAGTATATGA    5400

ATTACCCTTT CATTCAGCCT TTAGAAATTA TATTTTAGCC TTTATTTTTA ACCTGCCAAC    5460

ATACTTTAAG TAGGGATTAA TATTTAAGTG AACTATTGTG GGTTTTTTTG AATGTTGGTT    5520

TTAATACTTG ATTTAATCAC CACTCAAAAA TGTTTTGATG GTCTTAAGGA ACATCTCTGC    5580

TTTCACTCTT TAGAAATAAT GGTCATTCGG GCTGGGCGCA GCGGCTCACG CCTGTAATCC    5640

CAGCACTTTG GGAGGCCGAG GTGAGCGGAT CACAAGGTCA GGAGTTCGAG ACCAGCCTGG    5700

CCAAGAGACC AGCCTGGCCA GTATGGTGAA ACCCTGTCTC TACTAAAAAT ACAAAAATTA    5760

GCCGAGCATG GTGGCGGGCA CCTGTAGTCC CAGCTACTCG AGAGGCTGAG GCAGGAGAAT    5820

CTCTTGAACC TGGGAGGTGA AGGTTGCTGT GGGCCAAAAT CATGCCATTG CACTCCAGCC    5880

TGGGTGACAA GAGCGAAACT CCATCTCAAA AA                                  5912
```

(2) INFORMATION FOR SEQ ID NO:2:

(i) SEQUENCE CHARACTERISTICS:
        (A) LENGTH: 9171 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (viii) POSITION IN GENOME:
        (A) CHROMOSOME/SEGMENT: 11q22-23

(xi) SEQUENCE DESCRIPTION: SEQ ID NO:2:

```
ATGAGTCTAG TACTTAATGA TCTGCTTATC TGCTGCCGTC AACTAGAACA TGATAGAGCT      60
ACAGAACGAA AGAAAGAAGT TGAGAAATTT AAGCGCCTGA TTCGAGATCC TGAAACAATT     120
AAACATCTAG ATCGGCATTC AGATTCCAAA CAAGGAAAAT ATTTGAATTG GGATGCTGTT     180
TTTAGATTTT TACAGAAATA TATTCAGAAA GAAACAGAAT GTCTGAGAAT AGCAAAACCA     240
AATGTATCAG CCTCAACACA AGCCTCCAGG CAGAAAAAGA TGCAGGAAAT CAGTAGTTTG     300
GTCAAATACT TCATCAAATG TGCAAACAGA AGAGCACCTA GGCTAAAATG TCAAGAACTC     360
TTAAATTATA TCATGGATAC AGTGAAAGAT TCATCTAATG GTGCTATTTA CGGAGCTGAT     420
TGTAGCAACA TACTACTCAA AGACATTCTT TCTGTGAGAA ATACTGGTG TGAAATATCT      480
CAGCAACAGT GGTTAGAATT GTTCTCTGTG TACTTCAGGC TCTATCTGAA ACCTTCACAA     540
GATGTTCATA GAGTTTTAGT GGCTAGAATA ATTCATGCTG TTACCAAAGG ATGCTGTTCT     600
CAGACTGACG GATTAAATTC CAAATTTTTG GACTTTTTTT CCAAGGCTAT TCAGTGTGCG     660
AGACAAGAAA GAGCTCTTC AGGTCTAAAT CATATCTTAG CAGCTCTTAC TATCTTCCTC      720
AAGACTTTGG CTGTCAACTT TCGAATTCGA GTGTGTGAAT TAGGAGATGA AATTCTTCCC     780
ACTTTGCTTT ATATTTGGAC TCAACATAGG CTTAATGATT CTTTAAAAGA AGTCATTATT     840
GAATTATTTC AACTGCAAAT TTATATCCAT CATCCGAAAG GAGCCAAAAC CAAGAAAAA      900
GGTGCTTATG AATCAACAAA ATGGAGAAGT ATTTTATACA ACTTATATGA TCTGCTAGTG     960
AATGAGATAA GTCATATAGG AAGTAGAGGA AAGTATTCTT CAGGATTTCG TAATATTGCC    1020
GTCAAAGAAA ATTTGATTGA ATTGATGGCA GATATCTGTC ACCAGGTTTT TAATGAAGAT    1080
ACCAGATCCT TGGAGATTTC TCAATCTTAC ACTACTACAC AAAGAGAATC TAGTGATTAC    1140
AGTGTCCCTT GCAAAAGGAA GAAAATAGAA CTAGGCTGGG AAGTAATAAA AGATCACCTT    1200
CAGAAGTCAC AGAATGATTT TGATCTTGTG CCTTGGCTAC AGATTGCAAC CCAATTAATA    1260
TCAAAGTATC CTGCAAGTTT ACCTAACTGT GAGCTGTCTC CATTACTGAT GATACTATCT    1320
CAGCTTCTAC CCCAACAGCG ACATGGGGAA CGTACACCAT ATGTGTTACG ATGCCTTACG    1380
GAAGTTGCAT TGTGTCAAGA CAAGAGGTCA AACCTAGAAA GCTCACAAAA GTCAGATTTA    1440
TTAAAACTCT GGAATAAAAT TTGGTGTATT ACCTTTCGTG GTATAAGTTC TGAGCAAATA    1500
CAAGCTGAAA ACTTTGGCTT ACTTGGAGCC ATAATTCAGG GTAGTTTAGT TGAGGTTGAC    1560
AGAGAATTCT GGAAGTTATT TACTGGGTCA GCCTGCAGAC CTTCATGTCC TGCAGTATGC    1620
TGTTTGACTT TGGCACTGAC CACCAGTATA GTTCCAGGAA CGGTAAAAAT GGGAATAGAG    1680
CAAAATATGT GTGAAGTAAA TAGAAGCTTT TCTTTAAAGG AATCAATAAT GAAATGGCTC    1740
TTATTCTATC AGTTAGAGGG TGACTTAGAA AATAGCACAG AAGTGCCTCC AATTCTTCAC    1800
AGTAATTTTC CTCATCTTGT ACTGGAGAAA ATTCTTGTGA GTCTCACTAT GAAAAACTGT    1860
AAAGCTGCAA TGAATTTTTT CCAAAGCGTG CCAGAATGTG AACACCACCA AAAAGATAAA    1920
GAAGAACTTT CATTCTCAGA AGTAGAAGAA CTATTTCTTC AGCAACTTTT TGACAAGATG    1980
GACTTTTTAA CCATTGTGAG AGAATGTGGT ATAGAAAAGC ACCAGTCCAG TATTGGCTTC    2040
TCTGTCCACC AGAATCTCAA GGAATCACTG GATCGCTGTC TTCTGGGATT ATCAGAACAG    2100
CTTCTGAATA ATTACTCATC TGAGATTACA AATTCAGAAA CTCTTGTCCG GTGTTCACGT    2160
CTTTTGGTGG GTGTCCTTGG CTGCTACTGT TACATGGGTG TAATAGCTGA AGAGGAAGCA    2220
TATAAGTCAG AATTATTCCA GAAAGCCAAG TCTCTAATGC AATGTGCAGG AGAAAGTATC    2280
```

-continued

```
ACTCTGTTTA AAAATAAGAC AAATGAGGAA TTCAGAATTG GTTCCTTGAG AAATATGATG   2340

CAGCTATGTA CACGTTGCTT GAGCAACTGT ACCAAGAAGA GTCCAAATAA GATTGCATCT   2400

GGCTTTTTCC TGCGATTGTT AACATCAAAG CTAATGAATG ACATTGCAGA TATTTGTAAA   2460

AGTTTAGCAT CCTTCATCAA AAAGCCATTT GACCGTGGAG AAGTAGAATC AATGGAAGAT   2520

GATACTAATG GAAATCTAAT GGAGGTGGAG GATCAGTCAT CCATGAATCT ATTTAACGAT   2580

TACCCTGATA GTAGTGTTAG TGATGCAAAC GAACCTGGAG AGAGCCAAAG TACCATAGGT   2640

GCCATTAATC CTTTAGCTGA AGAATATCTG TCAAAGCAAG ATCTACTTTT CTTAGACATG   2700

CTCAAGTTCT TGTGTTTGTG TGTAACTACT GCTCAGACCA ATACTGTGTC CTTTAGGGCA   2760

GCTGATATTC GGAGGAAATT GTTAATGTTA ATTGATTCTA GCACGCTAGA ACCTACCAAA   2820

TCCCTCCACC TGCATATGTA TCTAATGCTT TTAAAGGAGC TTCCTGGAGA AGAGTACCCC   2880

TTGCCAATGG AAGATGTTCT TGAACTTCTG AAACCACTAT CCAATGTGTG TTCTTTGTAT   2940

CGTCGTGACC AAGATGTTTG TAAAACTATT TTAAACCATG TCCTTCATGT AGTGAAAAAC   3000

CTAGGTCAAA GCAATATGGA CTCTGAGAAC ACAAGGGATG CTCAAGGACA GTTTCTTACA   3060

GTAATTGGAG CATTTTGGCA TCTAACAAAG GAGAGGAAAT ATATATTCTC TGTAAGAATG   3120

GCCCTAGTAA ATTGCCTTAA AACTTTGCTT GAGGCTGATC CTTATTCAAA ATGGGCCATT   3180

CTTAATGTAA TGGGAAAAGA CTTTCCTGTA AATGAAGTAT TTACACAATT TCTTGCTGAC   3240

AATCATCACC AAGTTCGCAT GTTGGCTGCA GAGTCAATCA ATAGATTGTT CCAGGACACG   3300

AAGGGAGATT CTTCCAGGTT ACTGAAAGCA CTTCCTTTGA AGCTTCAGCA AACAGCTTTT   3360

GAAAATGCAT ACTTGAAAGC TCAGGAAGGA ATGAGAGAAA TGTCCCATAG TGCTGAGAAC   3420

CCTGAAACTT TGGATGAAAT TTATAATAGA AAATCTGTTT TACTGACGTT GATAGCTGTG   3480

GTTTTATCCT GTAGCCCTAT CTGCGAAAAA CAGGCTTTGT TTGCCCTGTG TAAATCTGTG   3540

AAAGAGAATG GATTAGAACC TCACCTTGTG AAAAAGGTTT TAGAGAAAGT TTCTGAAACT   3600

TTTGGATATA GACGTTTAGA AGACTTTATG GCATCTCATT TAGATTATCT GGTTTTGGAA   3660

TGGCTAAATC TTCAAGATAC TGAATACAAC TTATCTTCTT TTCCTTTTAT TTTATTAAAC   3720

TACACAAATA TTGAGGATTT CTATAGATCT TGTTATAAGG TTTTGATTCC ACATCTGGTG   3780

ATTAGAAGTC ATTTTGATGA GGTGAAGTCC ATTGCTAATC AGATTCAAGA GGACTGGAAA   3840

AGTCTTCTAA CAGACTGCTT TCCAAAGATT CTTGTAAATA TTCTTCCTTA TTTTGCCTAT   3900

GAGGGTACCA GAGACAGTGG GATGGCACAG CAAAGAGAGA CTGCTACCAA GGTCTATGAT   3960

ATGCTTAAAA GTGAAAACTT ATTGGGAAAA CAGATTGATC ACTTATTCAT TAGTAATTTA   4020

CCAGAGATTG TGGTGGAGTT ATTGATGACG TTACATGAGC CAGCAAATTC TAGTGCCAGT   4080

CAGAGCACTG ACCTCTGTGA CTTTTCAGGG GATTTGGATC CTGCTCCTAA TCCACCTCAT   4140

TTTCCATCGC ATGTGATTAA AGCAACATTT GCCTATATCA GCAATTGTCA TAAAACCAAG   4200

TTAAAAAGCA TTTTAGAAAT TCTTTCCAAA AGCCCTGATT CCTATCAGAA AATTCTTCTT   4260

GCCATATGTG AGCAAGCAGC TGAAACAAAT AATGTTTATA AGAAGCACAG AATTCTTAAA   4320

ATATATCACC TGTTTGTTAG TTTATTACTG AAAGATATAA AAAGTGGCTT AGGAGGAGCT   4380

TGGGCCTTTG TTCTTCGAGA CGTTATTTAT ACTTTGATTC ACTATATCAA CCAAAGGCCT   4440

TCTTGTATCA TGGATGTGTC ATTACGTAGC TTCTCCCTTT GTTGTGACTT ATTAAGTCAG   4500

GTTTGCCAGA CAGCCGTGAC TTACTGTAAG GATGCTCTAG AAAACCATCT TCATGTTATT   4560

GTTGGTACAC TTATACCCCT TGTGTATGAG CAGGTGGAGG TTCAGAAACA GGTATTGGAC   4620

TTGTTGAAAT ACTTAGTGAT AGATAACAAG GATAATGAAA ACCTCTATAT CACGATTAAG   4680
```

```
CTTTTAGATC CTTTTCCTGA CCATGTTGTT TTTAAGGATT TGCGTATTAC TCAGCAAAAA    4740

ATCAAATACA GTAGAGGACC CTTTTCACTC TTGGAGGAAA TTAACCATTT TCTCTCAGTA    4800

AGTGTTTATG ATGCACTTCC ATTGACAAGA CTTGAAGGAC TAAAGGATCT TCGAAGACAA    4860

CTGGAACTAC ATAAAGATCA GATGGTGGAC ATTATGAGAG CTTCTCAGGA TAATCCGCAA    4920

GATGGGATTA TGGTGAAACT AGTTGTCAAT TTGTTGCAGT TATCCAAGAT GGCAATAAAC    4980

CACACTGGTG AAAAGAAGT TCTAGAGGCT GTTGGAAGCT GCTTGGGAGA AGTGGGTCCT    5040

ATAGATTTCT CTACCATAGC TATACAACAT AGTAAAGATG CATCTTATAC CAAGGCCCTT    5100

AAGTTATTTG AAGATAAAGA ACTTCAGTGG ACCTTCATAA TGCTGACCTA CCTGAATAAC    5160

ACACTGGTAG AAGATTGTGT CAAAGTTCGA TCAGCAGCTG TTACCTGTTT GAAAAACATT    5220

TTAGCCACAA AGACTGGACA TAGTTTCTGG GAGATTTATA AGATGACAAC AGATCCAATG    5280

CTGGCCTATC TACAGCCTTT TAGAACATCA AGAAAAAAGT TTTTAGAAGT ACCCAGATTT    5340

GACAAAGAAA ACCCTTTTGA AGGCCTGGAT GATATAAATC TGTGGATTCC TCTAAGTGAA    5400

AATCATGACA TTTGGATAAA GACACTGACT TGTGCTTTTT TGGACAGTGG AGGCACAAAA    5460

TGTGAAATTC TTCAATTATT AAAGCCAATG TGTGAAGTGA AAACTGACTT TTGTCAGACT    5520

GTACTTCCAT ACTTGATTCA TGATATTTTA CTCCAAGATA CAAATGAATC ATGGAGAAAT    5580

CTGCTTTCTA CACATGTTCA GGGATTTTTC ACCAGCTGTC TTCGACACTT CTCGCAAACG    5640

AGCCGATCCA CAACCCCTGC AAACTTGGAT TCAGAGTCAG AGCACTTTTT CCGATGCTGT    5700

TTGGATAAAA AATCACAAAG AACAATGCTT GCTGTTGTGG ACTACATGAG AAGACAAAAG    5760

AGACCTTCTT CAGGAACAAT TTTTAATGAT GCTTTCTGGC TGGATTTAAA TTATCTAGAA    5820

GTTGCCAAGG TAGCTCAGTC TTGTGCTGCT CACTTTACAG CTTTACTCTA TGCAGAAATC    5880

TATGCAGATA AGAAAAGTAT GGATGATCAA GAGAAAAGAA GTCTTGCATT TGAAGAAGGA    5940

AGCCAGAGTA CAACTATTTC TAGCTTGAGT GAAAAAAGTA AGAAGAAAC TGGAATAAGT    6000

TTACAGGATC TTCTCTTAGA AATCTACAGA AGTATAGGGG AGCCAGATAG TTTGTATGGC    6060

TGTGGTGGAG GGAAGATGTT ACAACCCATT ACTAGACTAC GAACATATGA ACACGAAGCA    6120

ATGTGGGCA AAGCCCTAGT AACATATGAC CTCGAAACAG CAATCCCCTC ATCAACACGC    6180

CAGGCAGGAA TCATTCAGGC CTTGCAGAAT TTGGGACTCT GCCATATTCT TTCCGTCTAT    6240

TTAAAAGGAT TGGATTATGA AAATAAAGAC TGGTGTCCTG AACTAGAAGA ACTTCATTAC    6300

CAAGCAGCAT GGAGGAATAT GCAGTGGGAC CATTGCACTT CCGTCAGCAA AGAAGTAGAA    6360

GGAACCAGTT ACCATGAATC ATTGTACAAT GCTCTACAAT CTCTAAGAGA CAGAGAATTC    6420

TCTACATTTT ATGAAAGTCT CAAATATGCC AGAGTAAAAG AAGTGGAAGA GATGTGTAAG    6480

CGCAGCCTTG AGTCTGTGTA TTCGCTCTAT CCCACACTTA GCAGGTTGCA GGCCATTGGA    6540

GAGCTGGAAA GCATTGGGGA GCTTTTCTCA AGATCAGTCA CACATAGACA ACTCTCTGAA    6600

GTATATATTA AGTGGCAGAA ACACTCCCAG CTTCTCAAGG ACAGTGATTT TAGTTTTCAG    6660

GAGCCTATCA TGGCTCTACG CACAGTCATT TTGGAGATCC TGATGGAAAA GGAAATGGAC    6720

AACTCACAAA GAGAATGTAT TAAGGACATT CTCACCAAAC ACCTTGTAGA ACTCTCTATA    6780

CTGGCCAGAA CTTTCAAGAA CACTCAGCTC CCTGAAAGGG CAATATTTCA AATTAAACAG    6840

TACAATTCAG TTAGCTGTGG AGTCTCTGAG TGGCAGCTGG AAGAAGCACA AGTATTCTGG    6900

GCAAAAAAGG AGCAGAGTCT TGCCCTGAGT ATTCTCAAGC AAATGATCAA GAAGTTGGAT    6960

GCCAGCTGTG CAGCGAACAA TCCCAGCCTA AAACTTACAT ACACAGAATG TCTGAGGGTT    7020
```

```
TGTGGCAACT GGTTAGCAGA AACGTGCTTA GAAAATCCTG CGGTCATCAT GCAGACCTAT    7080

CTAGAAAAGG CAGTAGAAGT TGCTGGAAAT TATGATGGAG AAAGTAGTGA TGAGCTAAGA    7140

AATGGAAAAA TGAAGGCATT TCTCTCATTA GCCCGGTTTT CAGATACTCA ATACCAAAGA    7200

ATTGAAAACT ACATGAAATC ATCGGAATTT GAAAACAAGC AAGCTCTCCT GAAAAGAGCC    7260

AAAGAGGAAG TAGGTCTCCT TAGGGAACAT AAAATTCAGA CAAACAGATA CACAGTAAAG    7320

GTTCAGCGAG AGCTGGAGTT GGATGAATTA GCCCTGCGTG CACTGAAAGA GGATCGTAAA    7380

CGCTTCTTAT GTAAAGCAGT TGAAAATTAT ATCAACTGCT TATTAAGTGG AGAAGAACAT    7440

GATATGTGGG TATTCCGACT TTGTTCCCTC TGGCTTGAAA ATTCTGGAGT TTCTGAAGTC    7500

AATGGCATGA TGAAGAGAGA CGGAATGAAG ATTCCAACAT ATAAATTTTT GCCTCTTATG    7560

TACCAATTGG CTGCTAGAAT GGGGACCAAG ATGATGGGAG CCTAGGATT TCATGAAGTC     7620

CTCAATAATC TAATCTCTAG AATTTCAATG GATCACCCCC ATCACACTTT GTTTATTATA    7680

CTGGCCTTAG CAAATGCAAA CAGAGATGAA TTTCTGACTA AACCAGAGGT AGCCAGAAGA    7740

AGCAGAATAA CTAAAAATGT GCCTAAACAA AGCTCTCAGC TTGATGAGGA TCGAACAGAG    7800

GCTGCAAATA GAATAATATG TACTATCAGA AGTAGGAGAC CTCAGATGGT CAGAAGTGTT    7860

GAGGCACTTT GTGATGCTTA TATTATATTA GCAAACTTAG ATGCCACTCA GTGGAAGACT    7920

CAGAGAAAAG GCATAAATAT TCCAGCAGAC CAGCCAATTA CTAAACTTAA GAATTTAGAA    7980

GATGTTGTTG TCCCTACTAT GGAAATTAAG GTGGACCACA CAGGAGAATA TGGAAATCTG    8040

GTGACTATAC AGTCATTTAA AGCAGAATTT CGCTTAGCAG GAGGTGTAAA TTTACCAAAA    8100

ATAATAGATT GTGTAGGTTC CGATGGCAAG GAGAGGAGAC AGCTTGTTAA GGGCCGTGAT    8160

GACCTGAGAC AAGATGCTGT CATGCAACAG GTCTTCCAGA TGTGTAATAC ATTACTGCAG    8220

AGAAACACGG AAACTAGGAA GAGGAAATTA ACTATCTGTA CTTATAAGGT GGTTCCCCTC    8280

TCTCAGCGAA GTGGTGTTCT TGAATGGTGC ACAGGAACTG TCCCCATTGG TGAATTTCTT    8340

GTTAACAATG AAGATGGTGC TCATAAAAGA TACAGGCCAA ATGATTTCAG TGCCTTTCAG    8400

TGCCAAAAGA AAATGATGGA GGTGCAAAAA AAGTCTTTTG AAGAGAAATA TGAAGTCTTC    8460

ATGGATGTTT GCCAAAATTT TCAACCAGTT TTCCGTTACT TCTGCATGGA AAAATTCTTG    8520

GATCCAGCTA TTTGGTTTGA GAAGCGATTG GCTTATACGC GCAGTGTAGC TACTTCTTCT    8580

ATTGTTGGTT ACATACTTGG ACTTGGTGAT AGACATGTAC AGAATATCTT GATAAATGAG    8640

CAGTCAGCAG AACTTGTACA TATAGATCTA GGTGTTGCTT TTGAACAGGG CAAAATCCTT    8700

CCTACTCCTG AGACAGTTCC TTTTAGACTC ACCAGAGATA TTGTGGATGG CATGGGCATT    8760

ACGGGTGTTG AAGGTGTCTT CAGAAGATGC TGTGAGAAAA CCATGGAAGT GATGAGAAAC    8820

TCTCAGGAAA CTCTGTTAAC CATTGTAGAG GTCCTTCTAT ATGATCCACT CTTTGACTGG    8880

ACCATGAATC CTTTGAAAGC TTTGTATTTA CAGCAGAGGC CGGAAGATGA AACTGAGCTT    8940

CACCCTACTC TGAATGCAGA TGACCAAGAA TGCAAACGAA ATCTCAGTGA TATTGACCAG    9000

AGTTTCAACA AAGTAGCTGA ACGTGTCTTA ATGAGACTAC AAGAGAAACT GAAAGGAGTG    9060

GAAGAAGGCA CTGTGCTCAG TGTTGGTGGA CAAGTGAATT TGCTCATACA GCAGGCCATA    9120

GACCCCAAAA ATCTCAGCCG ACTTTTCCCA GGATGGAAAG CTTGGGTGTG A             9171
```

(2) INFORMATION FOR SEQ ID NO:3:

(i) SEQUENCE CHARACTERISTICS:
        (A) LENGTH: 3056 amino acids
        (B) TYPE: amino acid
        (C) STRANDEDNESS: single (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:3:

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Val Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys

```
                  370             375             380
Lys Arg Lys Lys Ile Glu Leu Gly Trp Glu Val Ile Lys Asp His Leu
385                 390             395                 400

Gln Lys Ser Gln Asn Asp Phe Asp Leu Val Pro Trp Leu Gln Ile Ala
                405             410              415

Thr Gln Leu Ile Ser Lys Tyr Pro Ala Ser Leu Pro Asn Cys Glu Leu
            420             425              430

Ser Pro Leu Leu Met Ile Leu Ser Gln Leu Leu Pro Gln Gln Arg His
            435             440             445

Gly Glu Arg Thr Pro Tyr Val Leu Arg Cys Leu Thr Glu Val Ala Leu
        450             455             460

Cys Gln Asp Lys Arg Ser Asn Leu Glu Ser Ser Gln Lys Ser Asp Leu
465             470             475                 480

Leu Lys Leu Trp Asn Lys Ile Trp Cys Ile Thr Phe Arg Gly Ile Ser
                485             490              495

Ser Glu Gln Lys Gln Ala Glu Asn Phe Gly Leu Leu Gly Ala Ile Ile
            500             505             510

Gln Gly Ser Leu Val Glu Val Asp Arg Glu Phe Trp Lys Leu Phe Thr
        515             520              525

Gly Ser Ala Cys Arg Pro Ser Cys Pro Ala Val Cys Cys Leu Thr Leu
530             535             540

Ala Leu Thr Thr Ser Ile Val Pro Gly Ala Val Lys Met Gly Ile Glu
545             550             555                  560

Gln Asn Met Cys Glu Val Asn Arg Ser Phe Ser Leu Lys Glu Ser Ile
            565             570              575

Met Lys Trp Leu Leu Phe Tyr Gln Leu Glu Gly Asp Leu Glu Asn Ser
            580             585              590

Thr Glu Val Pro Pro Ile Leu His Ser Asn Phe Pro His Leu Val Leu
        595             600              605

Glu Lys Ile Leu Val Ser Leu Thr Met Lys Asn Cys Lys Ala Ala Met
        610             615             620

Asn Phe Phe Gln Ser Val Pro Glu Cys Glu His His Lys Asp Lys
625             630             635                  640

Glu Glu Leu Ser Phe Ser Glu Val Glu Glu Leu Phe Leu Gln Thr Thr
            645             650              655

Phe Asp Lys Met Asp Phe Leu Thr Ile Val Arg Glu Cys Gly Ile Glu
            660             665             670

Lys His Gln Ser Ser Ile Gly Phe Ser Val His Gln Asn Leu Lys Glu
    675             680             685

Ser Leu Asp Arg Cys Leu Leu Gly Leu Ser Gln Leu Leu Asn Asn
            690             695             700

Tyr Ser Ser Glu Ile Thr Asn Ser Glu Thr Leu Val Arg Cys Ser Arg
705             710             715                  720

Leu Leu Val Gly Val Leu Gly Cys Tyr Cys Tyr Met Gly Val Ile Ala
                725             730             735

Glu Glu Glu Ala Tyr Lys Ser Glu Leu Phe Gln Lys Ala Asn Ser Leu
            740             745             750

Met Gln Cys Ala Gly Glu Ser Ile Thr Leu Phe Lys Asn Lys Thr Asn
            755             760             765

Glu Glu Phe Arg Ile Gly Ser Leu Arg Asn Met Met Gln Leu Cys Thr
        770             775             780

Arg Cys Leu Ser Asn Cys Thr Lys Lys Ser Pro Asn Lys Ile Ala Ser
785             790             795                  800
```

-continued

```
Gly Phe Phe Leu Arg Leu Leu Thr Ser Lys Leu Met Asn Asp Ile Ala
                805                 810                 815
Asp Ile Cys Lys Ser Leu Ala Ser Phe Ile Lys Lys Pro Phe Asp Arg
            820                 825                 830
Gly Glu Val Glu Ser Met Glu Asp Thr Asn Gly Asn Leu Met Glu
        835                 840                 845
Val Glu Asp Gln Ser Ser Met Asn Leu Phe Asn Asp Tyr Pro Asp Ser
850                 855                 860
Ser Val Ser Asp Ala Asn Glu Pro Gly Glu Ser Gln Ser Thr Ile Gly
865                 870                 875                 880
Ala Ile Asn Pro Leu Ala Glu Glu Tyr Leu Ser Lys Gln Asp Leu Leu
                885                 890                 895
Phe Leu Asp Met Leu Lys Phe Leu Cys Leu Cys Val Thr Thr Ala Gln
                900                 905                 910
Thr Asn Thr Val Ser Phe Arg Ala Ala Asp Ile Arg Arg Lys Leu Leu
            915                 920                 925
Met Leu Ile Asp Ser Ser Thr Leu Glu Pro Thr Lys Ser Leu His Leu
        930                 935                 940
His Met Tyr Leu Met Leu Leu Lys Glu Leu Pro Gly Glu Glu Tyr Pro
945                 950                 955                 960
Leu Pro Met Glu Asp Val Leu Glu Leu Leu Lys Pro Leu Ser Asn Val
                965                 970                 975
Cys Ser Leu Tyr Arg Arg Asp Gln Asp Val Cys Lys Thr Ile Leu Asn
                980                 985                 990
His Val Leu His Val Val Lys Asn Leu Gly Gln Ser Asn Met Asp Ser
            995                 1000                1005
Glu Asn Thr Arg Asp Ala Gln Gly Gln Phe Leu Thr Val Ile Gly Ala
        1010                1015                1020
Phe Trp His Leu Thr Lys Glu Arg Lys Tyr Ile Phe Ser Val Arg Met
1025                1030                1035                1040
Ala Leu Val Asn Cys Leu Lys Thr Leu Leu Glu Ala Asp Pro Tyr Ser
                1045                1050                1055
Lys Trp Ala Ile Leu Asn Val Met Gly Lys Asp Phe Pro Val Asn Glu
                1060                1065                1070
Val Phe Thr Gln Phe Leu Ala Asp Asn His His Gln Val Arg Met Leu
            1075                1080                1085
Ala Ala Glu Ser Ile Asn Arg Leu Phe Gln Asp Thr Lys Gly Asp Ser
        1090                1095                1100
Ser Arg Leu Leu Lys Ala Leu Pro Leu Lys Leu Gln Gln Thr Ala Phe
1105                1110                1115                1120
Glu Asn Ala Tyr Leu Lys Ala Gln Glu Gly Met Arg Glu Met Ser His
                1125                1130                1135
Ser Ala Glu Asn Pro Glu Thr Leu Asp Glu Ile Tyr Asn Arg Lys Ser
                1140                1145                1150
Val Leu Leu Thr Leu Ile Ala Val Val Leu Ser Cys Ser Pro Ile Cys
            1155                1160                1165
Glu Lys Gln Ala Leu Phe Ala Leu Cys Lys Ser Val Lys Glu Asn Gly
        1170                1175                1180
Leu Glu Pro His Leu Val Lys Lys Val Leu Glu Lys Val Ser Glu Thr
1185                1190                1195                1200
Phe Gly Tyr Arg Arg Leu Glu Asp Phe Met Ala Ser His Leu Asp Tyr
                1205                1210                1215
```

-continued

```
Leu Val Leu Glu Trp Leu Asn Leu Gln Asp Thr Glu Tyr Asn Leu Ser
        1220                1225                1230
Ser Phe Pro Phe Ile Leu Leu Asn Tyr Thr Asn Ile Glu Asp Phe Tyr
        1235                1240                1245
Arg Ser Cys Tyr Lys Val Leu Ile Pro His Leu Val Ile Arg Ser His
        1250                1255                1260
Phe Asp Glu Val Lys Ser Ile Ala Asn Gln Ile Gln Glu Asp Trp Lys
1265                1270                1275                1280
Ser Leu Leu Thr Asp Cys Phe Pro Lys Ile Leu Val Asn Ile Leu Pro
        1285                1290                1295
Tyr Phe Ala Tyr Glu Gly Thr Arg Asp Ser Gly Met Ala Gln Gln Arg
        1300                1305                1310
Glu Thr Ala Thr Lys Val Tyr Asp Met Leu Lys Ser Glu Asn Leu Leu
        1315                1320                1325
Gly Lys Gln Ile Asp His Leu Phe Ile Ser Asn Leu Pro Glu Ile Val
        1330                1335                1340
Val Glu Leu Leu Met Thr Leu His Glu Pro Ala Asn Ser Ser Ala Ser
1345                1350                1355                1360
Gln Ser Thr Asp Leu Cys Asp Phe Ser Gly Asp Leu Asp Pro Ala Pro
        1365                1370                1375
Asn Pro Pro His Phe Pro Ser His Val Ile Lys Ala Thr Phe Ala Tyr
        1380                1385                1390
Ile Ser Asn Cys His Lys Thr Lys Leu Lys Ser Ile Leu Glu Ile Leu
        1395                1400                1405
Ser Lys Ser Pro Asp Ser Tyr Gln Lys Ile Leu Leu Ala Ile Cys Glu
        1410                1415                1420
Gln Ala Ala Glu Thr Asn Asn Val Tyr Lys Lys His Arg Ile Leu Lys
1425                1430                1435                1440
Ile Tyr His Leu Phe Val Ser Leu Leu Leu Lys Asp Ile Lys Ser Gly
        1445                1450                1455
Leu Gly Gly Ala Trp Ala Phe Val Leu Arg Asp Val Ile Tyr Thr Leu
        1460                1465                1470
Ile His Tyr Ile Asn Gln Arg Pro Ser Cys Ile Met Asp Val Ser Leu
        1475                1480                1485
Arg Ser Phe Ser Leu Cys Cys Asp Leu Leu Ser Gln Val Cys Gln Thr
        1490                1495                1500
Ala Val Thr Tyr Cys Lys Asp Ala Leu Glu Asn His Leu His Val Ile
1505                1510                1515                1520
Val Gly Thr Leu Ile Pro Leu Val Tyr Glu Gln Val Glu Val Gln Lys
        1525                1530                1535
Gln Val Leu Asp Leu Leu Lys Tyr Leu Val Ile Asp Asn Lys Asp Asn
        1540                1545                1550
Glu Asn Leu Tyr Ile Thr Ile Lys Leu Leu Asp Pro Phe Pro Asp His
        1555                1560                1565
Val Val Phe Lys Asp Leu Arg Ile Thr Gln Gln Lys Ile Lys Tyr Ser
        1570                1575                1580
Arg Gly Pro Phe Ser Leu Leu Glu Glu Ile Asn His Phe Leu Ser Val
1585                1590                1595                1600
Ser Val Tyr Asp Ala Leu Pro Leu Thr Arg Leu Glu Gly Leu Lys Asp
        1605                1610                1615
Leu Arg Arg Gln Leu Glu Leu His Lys Asp Gln Met Val Asp Ile Met
        1620                1625                1630
Arg Ala Ser Gln Asp Asn Pro Gln Asp Gly Ile Met Val Lys Leu Val
```

-continued

```
              1635            1640            1645

Val Asn Leu Gln Leu Ser Lys Met Ala Ile Asn His Thr Gly Glu
1650            1655            1660

Lys Glu Val Leu Glu Ala Val Gly Ser Cys Leu Gly Glu Val Gly Pro
1665            1670            1675            1680

Ile Asp Phe Ser Thr Ile Ala Ile Gln His Ser Lys Asp Ala Ser Tyr
                1685            1690            1695

Thr Lys Ala Leu Lys Leu Phe Glu Asp Lys Glu Leu Gln Trp Thr Phe
            1700            1705            1710

Ile Met Leu Thr Tyr Leu Asn Asn Thr Leu Val Glu Asp Cys Val Lys
            1715            1720            1725

Val Arg Ser Ala Ala Val Thr Cys Leu Lys Asn Ile Leu Ala Thr Lys
            1730            1735            1740

Thr Gly His Ser Phe Trp Glu Ile Tyr Lys Met Thr Thr Asp Pro Met
1745            1750            1755            1760

Leu Ala Tyr Leu Gln Pro Phe Arg Thr Ser Arg Lys Lys Phe Leu Glu
                1765            1770            1775

Val Pro Arg Phe Asp Lys Glu Asn Pro Phe Glu Gly Leu Asp Asp Ile
            1780            1785            1790

Asn Leu Trp Ile Pro Leu Ser Glu Asn His Asp Ile Trp Ile Lys Thr
            1795            1800            1805

Leu Thr Cys Ala Phe Leu Asp Ser Gly Gly Thr Lys Cys Glu Ile Leu
            1810            1815            1820

Gln Leu Leu Lys Pro Met Cys Glu Val Lys Thr Asp Phe Cys Gln Thr
1825            1830            1835            1840

Val Leu Pro Tyr Leu Ile His Asp Ile Leu Leu Gln Asp Thr Asn Glu
                1845            1850            1855

Ser Trp Arg Asn Leu Leu Ser Thr His Val Gln Gly Phe Phe Thr Ser
            1860            1865            1870

Cys Leu Arg His Phe Ser Gln Thr Ser Arg Ser Thr Thr Pro Ala Asn
            1875            1880            1885

Leu Asp Ser Glu Ser Glu His Phe Phe Arg Cys Cys Leu Asp Lys Lys
            1890            1895            1900

Ser Gln Arg Thr Met Leu Ala Val Val Asp Tyr Met Arg Arg Gln Lys
1905            1910            1915            1920

Arg Pro Ser Ser Gly Thr Ile Phe Asn Asp Ala Phe Trp Leu Asp Leu
                1925            1930            1935

Asn Tyr Leu Glu Val Ala Lys Val Ala Gln Ser Cys Ala Ala His Phe
            1940            1945            1950

Thr Ala Leu Leu Tyr Ala Glu Ile Tyr Ala Asp Lys Lys Ser Met Asp
            1955            1960            1965

Asp Gln Glu Lys Arg Ser Leu Ala Phe Glu Glu Gly Ser Gln Ser Thr
            1970            1975            1980

Thr Ile Ser Ser Leu Ser Glu Lys Ser Lys Glu Glu Thr Gly Ile Ser
1985            1990            1995            2000

Leu Gln Asp Leu Leu Leu Glu Ile Tyr Arg Ser Ile Gly Glu Pro Asp
                2005            2010            2015

Ser Leu Tyr Gly Cys Gly Gly Lys Met Leu Gln Pro Ile Thr Arg
            2020            2025            2030

Leu Arg Thr Tyr Glu His Glu Ala Met Trp Gly Lys Ala Leu Val Thr
            2035            2040            2045

Tyr Asp Leu Glu Thr Ala Ile Pro Ser Ser Thr Arg Gln Ala Gly Ile
            2050            2055            2060
```

```
Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
            2085                2090                2095

Glu Leu His Tyr Gln Ala Ala Trp Arg Asn Met Gln Trp Asp His Cys
        2100                2105                2110

Thr Ser Val Ser Lys Glu Val Glu Gly Thr Ser Tyr His Glu Ser Leu
    2115                2120                2125

Tyr Asn Ala Leu Gln Ser Leu Arg Asp Arg Glu Phe Ser Thr Phe Tyr
2130                2135                2140

Glu Ser Leu Lys Tyr Ala Arg Val Lys Glu Val Glu Met Cys Lys
2145                2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
        2180                2185                2190

Val Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile Met
2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
        2260                2265                2270

Arg Ala Ile Phe Gln Ile Lys Gln Tyr Asn Ser Val Ser Cys Gly Val
    2275                2280                2285

Ser Glu Trp Gln Leu Glu Glu Ala Gln Val Phe Trp Ala Lys Lys Glu
        2290                2295                2300

Gln Ser Leu Ala Leu Ser Ile Leu Lys Gln Met Ile Lys Lys Leu Asp
2305                2310                2315                2320

Ala Ser Cys Ala Ala Asn Asn Pro Ser Leu Lys Leu Thr Tyr Thr Glu
            2325                2330                2335

Cys Leu Arg Val Cys Gly Asn Trp Leu Ala Glu Thr Cys Leu Glu Asn
        2340                2345                2350

Pro Ala Val Ile Met Gln Thr Tyr Leu Glu Lys Ala Val Glu Val Ala
    2355                2360                2365

Gly Asn Tyr Asp Gly Glu Ser Ser Asp Glu Leu Arg Asn Gly Lys Met
    2370                2375                2380

Lys Ala Phe Leu Ser Leu Ala Arg Phe Ser Asp Thr Gln Tyr Gln Arg
2385                2390                2395                2400

Ile Glu Asn Tyr Met Lys Ser Ser Glu Phe Glu Asn Lys Gln Ala Leu
            2405                2410                2415

Leu Lys Arg Ala Lys Glu Glu Val Gly Leu Leu Arg Glu His Lys Ile
        2420                2425                2430

Gln Thr Asn Arg Tyr Thr Val Lys Val Gln Arg Glu Leu Glu Leu Asp
    2435                2440                2445

Glu Leu Ala Leu Arg Ala Leu Lys Glu Asp Arg Lys Arg Phe Leu Cys
2450                2455                2460

Lys Ala Val Glu Asn Tyr Ile Asn Cys Leu Leu Ser Gly Glu Glu His
2465                2470                2475                2480
```

-continued

```
Asp Met Trp Val Phe Arg Leu Cys Ser Leu Trp Leu Glu Asn Ser Gly
            2485                2490                2495

Val Ser Glu Val Asn Gly Met Met Lys Arg Asp Gly Met Lys Ile Pro
        2500                2505                2510

Thr Tyr Lys Phe Leu Pro Leu Met Tyr Gln Leu Ala Ala Arg Met Gly
        2515                2520                2525

Thr Lys Met Met Gly Gly Leu Gly Phe His Val Leu Asn Asn Leu
    2530                2535                2540

Ile Ser Arg Ile Ser Met Asp His Pro His Thr Leu Phe Ile Ile
2545                2550                2555                2560

Leu Ala Leu Ala Asn Ala Asn Arg Asp Glu Phe Leu Thr Lys Pro Glu
            2565                2570                2575

Val Ala Arg Arg Ser Arg Ile Thr Lys Asn Val Pro Lys Gln Ser Ser
            2580                2585                2590

Gln Leu Asp Glu Asp Arg Thr Glu Ala Ala Asn Arg Ile Ile Cys Thr
            2595                2600                2605

Ile Arg Ser Arg Arg Pro Gln Met Val Arg Ser Val Glu Ala Leu Cys
    2610                2615                2620

Asp Ala Tyr Ile Ile Leu Ala Asn Leu Asp Ala Thr Gln Trp Lys Thr
2625                2630                2635                2640

Gln Arg Lys Gly Ile Asn Ile Pro Ala Asp Gln Pro Ile Thr Lys Leu
            2645                2650                2655

Lys Asn Leu Glu Asp Val Val Pro Thr Met Glu Ile Lys Val Asp
            2660                2665                2670

His Thr Gly Glu Tyr Gly Asn Leu Val Thr Ile Gln Ser Phe Lys Ala
            2675                2680                2685

Glu Phe Arg Leu Ala Gly Gly Val Asn Leu Pro Lys Ile Ile Asp Cys
        2690                2695                2700

Val Gly Ser Asp Gly Lys Glu Arg Arg Gln Leu Val Lys Gly Arg Asp
2705                2710                2715                2720

Asp Leu Arg Gln Asp Ala Val Met Gln Gln Val Phe Gln Met Cys Asn
            2725                2730                2735

Thr Leu Leu Gln Arg Asn Thr Glu Thr Arg Lys Arg Lys Leu Thr Ile
            2740                2745                2750

Cys Thr Tyr Lys Val Val Pro Leu Ser Gln Arg Ser Gly Val Leu Glu
        2755                2760                2765

Trp Cys Thr Gly Thr Val Pro Ile Gly Glu Phe Leu Val Asn Asn Glu
    2770                2775                2780

Asp Gly Ala His Lys Arg Tyr Arg Pro Asn Asp Phe Ser Ala Phe Gln
2785                2790                2795                2800

Cys Gln Lys Lys Met Met Glu Val Gln Lys Lys Ser Phe Glu Glu Lys
            2805                2810                2815

Tyr Glu Val Phe Met Asp Val Cys Gln Asn Phe Gln Pro Val Phe Arg
        2820                2825                2830

Tyr Phe Cys Met Glu Lys Phe Leu Asp Pro Ala Ile Trp Phe Glu Lys
            2835                2840                2845

Arg Leu Ala Tyr Thr Arg Ser Val Ala Thr Ser Ser Ile Val Gly Tyr
        2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
            2885                2890                2895

Gly Lys Ile Leu Pro Thr Pro Glu Thr Val Pro Phe Arg Leu Thr Arg
```

-continued

```
                2900                2905                2910
Asp Ile Val Asp Gly Met Gly Ile Thr Gly Val Glu Gly Val Phe Arg
            2915                2920                2925
Arg Cys Cys Glu Lys Thr Met Glu Val Met Arg Asn Ser Gln Glu Thr
        2930                2935                2940
Leu Leu Thr Ile Val Glu Val Leu Leu Tyr Asp Pro Leu Phe Asp Trp
2945                2950                2955                2960
Thr Met Asn Pro Leu Lys Ala Leu Tyr Leu Gln Gln Arg Pro Glu Asp
                2965                2970                2975
Glu Thr Glu Leu His Pro Thr Leu Asn Ala Asp Asp Gln Glu Cys Lys
            2980                2985                2990
Arg Asn Leu Ser Asp Ile Asp Gln Ser Phe Asp Lys Val Ala Glu Arg
        2995                3000                3005
Val Leu Met Arg Leu Gln Glu Lys Leu Lys Gly Val Glu Glu Gly Thr
    3010                3015                3020
Val Leu Ser Val Gly Gly Gln Val Asn Leu Leu Ile Gln Gln Ala Ile
3025                3030                3035                3040
Asp Pro Lys Asn Leu Ser Arg Leu Phe Pro Gly Trp Lys Ala Trp Val
                3045                3050                3055
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
His Glu Pro Ala Asn Ser Ser Ala Ser Gln Ser Thr Asp Leu Cys
1               5                   10                  15
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Cys Lys Arg Asn Leu Ser Asp Ile Asp Gln Ser Phe Asp Lys Val
1               5                   10                  15
```

(2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Pro Glu Asp Glu Thr Glu Leu His Pro Thr Leu Asn Ala Asp Asp Gln
1               5                   10                  15
Glu Cys
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Cys Lys Ser Leu Ala Ser Phe Ile Lys Lys Pro Phe Asp Arg Gly Glu
1               5                   10                  15

Val Glu Ser Met Glu Asp Asp Thr Asn Gly
            20                  25
```

(2) INFORMATION FOR SEQ ID NO:8:

(i) SEQUENCE CHARACTERISTICS:
        (A) LENGTH: 3607 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 3'UTR
        (B) LOCATION: 1..3607

(xi) SEQUENCE DESCRIPTION: SEQ ID NO:8:

```
TCTTCAGTAT ATGAATTACC CTTTCATTCA GCCTTTAGAA ATTATATTTT AGCCTTTATT        60

TTTAACCTGC CAACATACTT TAAGTAGGGA TTAATATTTA AGTGAACTAT TGTGGGTTTT       120

TTTGAATGTT GGTTTTAATA CTTGATTTAA TCACCACTCA AAAATGTTTT GATGGTCTTA       180

AGGAACATCT CTGCTTTCAC TCTTTAGAAA TAATGGTCAT TCGGGCTGGG CGCAGCGGCT       240

CACGCCTGTA ATCCCAGCAC TTTGGGAGGC CGAGGTGAGC GGATCACAAG GTCAGGAGTT       300

CGAGACCAGC CTGGCCAAGA GACCAGCCTG GCCAGTATGG TGAAACCCTG TCTCTACTAA       360

AAATACAAAA ATTAGCCGAG CATGGTGGCG GGCACCTGTA ATCCCAGCTA CTCGAGAGGC       420

TGAGGCAGGA GAATCTCTTG AACCTGGGAG GTGAAGGTTG CTGTGGGCCA AAATCATGCC       480

ATTGCACTCC AGCCTGGGTG ACAAGAGCGA AACTCCATCT CAAAAAAAAA AAAAAAAAAC       540

AGAAACTTAT TTGGATTTTT CCTAGTAAGA TCACTCAGTG TTACTAAATA ATGAAGTTGT       600

TATGGAGAAC AAATTTCAAA GACACAGTTA GTGTAGTTAC TATTTTTTA AGTGTGTATT       660

AAAACTTCTC ATTCTATTCT CTTTATCTTT TAAGCCCTTC TGTACTGTCC ATGTATGTTA       720

TCTTTCTGTG ATAACTTCAT AGATTGCCTT CTAGTTCATG AATTCTCTTG TCAGATGTAT       780

ATAATCTCTT TTACCCTATC CATTGGGCTT CTTCTTTCAG AAATTGTTTT TCATTTCTAA       840

TTATGCATCA TTTTTCAGAT CTCTGTTTCT TGATGTCATT TTTAATGTTT TTTTAATGTT       900

TTTTATGTCA CTAATTATTT TAAATGTCTG TACCTGATAG ACACTGTAAT AGTTCTATTA       960

AATTTAGTTC CTGCTGTTTA TATCTGTTGA TTTTTGTATT TGATAGGCTG TTCATCCAGT      1020

TTTGTCTTTT TGAAAAGTGA GTTTATTTTC AGCAAGGCTT TATCTATGGG AATCTTGAGT      1080

GTCTGTTTAT GTCATATTCC CAGGGCTGTT GCTGCACACA AGCCCATTCT TATTTTAATT      1140

TCTTGGCTTT AGGGTTTCCA TACCTGAAGT GTAGCATAAA TACTGATAGG AGATTTCCCA      1200
```

```
GGCCAAGGCA AACACACTTC CTCCTCATCT CCTTGTGCTA GTGGGCAGAA TATTTGATTG    1260

ATGCCTTTTT CACTGAGAGT ATAAGCTTCC ATGTGTCCCA CCTTTATGGC AGGGGTGGAA    1320

GGAGGTACAT TTAATTCCCA CTGCCTGCCT TTGGCAAGCC CTGGGTTCTT TGCTCCCCAT    1380

ATAGATGTCT AAGCTAAAAG CCGTGGGTTA ATGAGACTGG CAAATTGTTC CAGGACAGCT    1440

ACAGCATCAG CTCACATATT CACCTCTCTG GTTTTTCATT CCCCTCATTT TTTTCTGAGA    1500

CAGAGTCTTG CTCTGTCACC CAGGCTGGAG TGCAGTGGCA TGATCTCAGC TCACTGAAAC    1560

CTCTGCCTCC TGGGTTCAAG CAATTCTCCT GCCTCAGCCT CCCGAGTAGC TGGGACTACA    1620

GGCGTGTGCC AACACGCCCG GCTAATTTTT TGTATTTTTA TTAGAGACGG AGTTTCACCG    1680

TGTTAGCCAG GATGGTCTCG ATCGCTTGAC CTCGTGATCC ACCCTCCTCG GCCTCCCAAA    1740

GTGCTGGGAT TACAGGTGTG AGCCACCGCG CCCGGCCTCA TTCCCCTCAT TTTTGACCGT    1800

AAGGATTTCC CCTTTCTTGT AAGTTCTGCT ATGTATTTAA AGAATGTTT TCTACATTTT     1860

ATCCAGCATT TCTCTGTGTT CTGTTGGAAG GGAAGGGCTT AGGTATCTAG TTTGATACAT    1920

AGGTAGAAGT GGAACATTTC TCTGTCCCCC AGCTGTCATC ATATAAGATA AACATCAGAT    1980

AAAAAGCCAC CTGAAAGTAA AACTACTGAC TCGTGTATTA GTGAGTATAA TCTCTTCTCC    2040

ATCCTTAGGA AAATGTTCAT CCCAGCTGCG GAGATTAACA AATGGGTGAT TGAGCTTTCT    2100

CCTCGTATTT GGACCTTGAA GGTTATATAA ATTTTTTTCT TATGAAGAGT TGGCATTTCT    2160

TTTTATTGCC AATGGCAGGC ACTCATTCAT ATTTGATCTC CTCACCTTCC CCTCCCCTAA    2220

AACCAATCTC CAGAACTTTT TGGACTATAA ATTTCTTGGT TTGACTTCTG GAGAACTGTT    2280

CAGAATATTA CTTTGCATTT CAAATTACAA ACTTACCTTG GTGTATCTTT TTCTTACAAG    2340

CTGCCTAAAT GAATATTTGG TATATATTGG TAGTTTTATT ACTATAGTAA ATCAAGGAAA    2400

TGCAGTAAAC TTAAAATGTC TTTAAGAAAG CCCTGAAATC TTCATGGGTG AAATTAGAAA    2460

TTATCAACTA GATAATAGTA TAGATAAATG AATTTGTAGC TAATTCTTGC TAGTTGTTGC    2520

ATCCAGAGAG CTTTGAATAA CATCATTAAT CTACTCTTTA GCCTTGCATG GTATGCTATG    2580

AGGCTCCTGT TCTGTTCAAG TATTCTAATC AATGGCTTTG AAAAGTTTAT CAAATTTACA    2640

TACAGATCAC AAGCCTAGGA GAAATAACTA ATTCACAGAT GACAGAATTA AGATTATAAA    2700

AGATTTTTTT TTGGTAATTT TAGTAGAGAC AGGGTTGCCA TTGTATTCCA GCCTTGGCGA    2760

CAGAGCAAGA CTCTGCCTCA AAAAAAAAAA AAAAAAGGTT TTGCCAAGCT GGAACTCTTT    2820

CTGCAAATGA CTAAGATAGA AAACTGCCAA GGACAAATGA GGAGTAGTTA GATTTTGAAA    2880

ATATTAATCA TAGAATAGTT GTTGTATGCT AAGTCACTGA CCCATATTAT GTACAGCATT    2940

TCTGATCTTT ACTTTGCAAG ATTAGTGATA CTATGCCAAT ACACTGCTGG AGAAATCAGA    3000

ATTTGGAGAA ATAAGTTGTC CAAGGCAAGA AGATAGTAAA TTATAAGTAC AAGTGTAATA    3060

TGGACAGTAT CTAACTTGAA AAGATTTCAG GCGAAAAGAA TCTGGGGTTT GCCAGTCAGT    3120

TGCTCAAAAG GTCAATGAAA ACCAAATAGT GAAGCTATCA GAGAAGCTAA TAAATTATAG    3180

ACTGCTTGAA CAGTTGTGTC CAGATTAAGG GAGATAAATG CTTTCCCACC CTACTTTGTG    3240

CAGGTCATAC CTCCCCAAAG TGTTTACCTA ATCAGTAGGT TCACAAACTC TTGGTCATTA    3300

TAGTATATGC CTAAAATGTA TGCACTTAGG AATGCTAAAA ATTTAAATAT GGTCTAAAGC    3360

AAATAAAAGC AAAGAGGAAA AACTTTGGAC ATCGTAAAGA CTAGAATAGT CTTTTAAAAA    3420

GAAAGCCAGT ATATTGGTTT GAAATATAGA GATGTGTCCC AATTTCAAGT ATTTTAATTG    3480

CACCTTAATG AAATTATCTA TTTTCTATAG ATTTTAGTAC TATTGAATGT ATTACTTTAC    3540

TGTTACCTGA ATTTATTATA AAGTGTTTTT GAATAAATAA TTCTAAAAGC AAAAAAAAAA    3600
```

AAAAAAA                                                                   3607

(2) INFORMATION FOR SEQ ID NO:9:

(i) SEQUENCE CHARACTERISTICS:
        (A) LENGTH: 884 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: 5'UTR
        (B) LOCATION: 1..884

(xi) SEQUENCE DESCRIPTION: SEQ ID NO:9:

```
TCCTCCTTTT AAACGCCCTG AATTGAACCC TGCCTCCTGC GCATCCTCTT TTTGTGTCAC     60

CTTAGGGTTC AGATTTAACT ACGCGACTTG ACTAGTCATC TTTTGATCTC TCTCTCGTAT    120

TTAGTACTTT TAGTCAGCGA GCATTTATTG ATATTTCAAC TTCAGCCTCG CGGTTAAGAG    180

CTTGGGCTCT GGAATCATAC GGCTGGAATT GGAATTCTGT CAGTCGTGTG GCCGCTCTCT    240

ACTGTCTTGT GAAGATAAGT GAGATAATCT TGACCTGTGG TGAGCACTCG TGAGCGTTAG    300

CTGCTGTATT TACCAGGTAC AGATAAGACA ACTACAGTGG ATGATAATGT ATGTGGTGAT    360

AGGGGAGTAC TCTGATGGTA GAGGAGTGAC TTTGGTTCTC TGCAAACTCA GCCTGAGACT    420

ATCAATTCAG TTTGTGGTGA GACCTCGCAG TGTTACCTTG GCAGATGGTA GAAGCCTTCC    480

AGATGGAAGG AAAAATGCGT GTAAAGGCAC AAAGTGTAGA AGGACCCTGA AGCTCCAGCG    540

TGAGGCCTGG CATTGAATGA AATATATTTT GTGGGTTTTC AGCTGCTGAA GTCATAGGAA    600

TGGATGAGAC CAAGAAAACA AAGCTGTTTT TGAGGTATGA GCGGAAGAAG AGATATCAGG    660

AGACTTTCGA AACAGTCATA ACGGAAGTTA ATATGATCAT TGCTAACATT TGCTGTGTTT    720

CAGGCACTGT AAGCATGTAT ATGGGTCCTT AAAGGGACTC ATAGAGAGGC ATACATCACA    780

ATTTGGAATT ATGCATTGGT TTATCAATTT ACTTGTTTAT TGTCACCCTG CTGCCCAGAT    840

ATGACTTCAT GAGGACAGTG ATGTGTGTTC TGAAATTGTG AACC                     884
```

(2) INFORMATION FOR SEQ ID NO:10:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
AGGTAGCTGC GTGGCTAACG GAGAAAAGAA GCCGTGGCCA CGGGAGGAGG CGAGAGGAGT     60

CGGGATCTGC GCTGCAGCCA CCGCCGCGGT TGATACTACT TTGACCTTCC GAGTGCAGTG    120
```

(2) INFORMATION FOR SEQ ID NO:11:

(i) SEQUENCE CHARACTERISTICS:
        (A) LENGTH: 9620 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Mus musculus (viii) POSITION IN GENOME:
    (A) CHROMOSOME/SEGMENT: Chromosome 9, Band 9C (xi) SEQUENCE DESCRIPTION: SEQ ID NO:11:

| | | | | | |
|---|---|---|---|---|---|
| AGAATGCAGC | GGTGAGGATG | CATGTTCTGA | AATCTTAAAC | CATGAGTCTA | GCACTCAATG | 60 |
| ATCTGCTCAT | TTGCTGCCGG | CAGTTAGAGC | ATGACAGAGC | TACAGAAAGA | AGGAAAGAAG | 120 |
| TGGATAAATT | TAAGCGCCTG | ATTCAGGATC | CTGAAACAGT | TCAACATTTA | GATAGGCATT | 180 |
| CTGATTCCAA | ACAAGGAAAA | TATCTGAATT | GGGATGCTGT | TTTCAGGTTT | TTACAGAAGT | 240 |
| ACATTCAAAA | AGAAATGGAA | AGTCTGAGAA | CAGCAAAATC | AAATGTATCA | GCCACCACAC | 300 |
| AGAGCTCCAG | ACAGAAGAAG | ATGCAAGAGA | TCAGCAGTTT | GGTCAGATAC | TTCATCAAAT | 360 |
| GTGCAAACAA | AAGAGCACCC | AGGCTAAAAT | GTCAAGACCT | CTTGAATTAT | GTCATGGATA | 420 |
| CAGTGAAAGA | CTCATCTAAT | GGTCTAACGT | ATGGAGCTGA | CTGTAGCAAC | ATACTACTCA | 480 |
| AAGACATTCT | TTCTGTGAGA | AAATACTGGT | GTGAAGTATC | TCAGCAACAG | TGGCTAGAAT | 540 |
| TGTTTTCACT | GTACTTCAGG | CTGTATCTCA | AGCCATCACA | GGACATTAAT | AGAGTTTTAG | 600 |
| TGGCTAGAAT | AATTCATGCT | GTCACCAGAG | GATGCTGTTC | ACAGACTGAT | GGATTACCTT | 660 |
| CAAAGTTTTT | AGATCTTTTT | TCCAAGGCTA | TTCAGTATGC | CAGACAAGAA | AAGAGCTCTC | 720 |
| CTGGCTTAAG | TCACATCTTA | GCAGCCCTTA | ACATTTTCCT | CAAGTCTCTG | GCTGTCAACT | 780 |
| TCCGAAAACG | GGTGTGTGAA | GCAGGAGATG | AAATTCTTCC | TACCTTACTA | TATATTTGGA | 840 |
| CTCAACATAG | ACTTAATGAT | TCTTTAAAAG | AAGTAATTAT | TGAACTAATT | CAACTGCAGA | 900 |
| TTTATATCCA | TCATCCACAA | GGAGCCAGAG | CTCCTGAAGA | AGGTGCTTAT | GAATCCATGA | 960 |
| AATGGAAAAG | TATCTTGTAC | AACTTATATG | ACTTGCTAGT | GAATGAGATA | AGTCATATAG | 1020 |
| GAAGCCGAGG | GAAATATTCC | TCAGGATCTC | GTAATATTGC | TGTCAAGGAA | AATCTGATTG | 1080 |
| ACCTGATGGC | AGATATCTGT | TACCAGCTTT | TTGATGCAGA | TACCAGATCC | GTGGAGATTT | 1140 |
| CTCAATCTTA | TGTGACACAA | AGGGAATCCA | CTGATTACAG | TGTACCTTGC | AAAAGAAGGA | 1200 |
| AAATAGACGT | AGGCTGGGAA | GTGATAAAAG | ATTATCTTCA | GAAGTCACAG | AGTGATTTTG | 1260 |
| ATCTCGTGCC | TTGGCTACAG | ATTACAACCC | GATTAATATC | AAAATATCCT | TCCAGTTTAC | 1320 |
| CTAACTGTGA | GCTGTCTCCA | TTAATACTGA | TACTGTACCA | GCTTCTGCCT | CAACAGCGAC | 1380 |
| GTGGAGAACG | CATCCCATAT | GTGTTACGAT | GCCTTAAGGA | AGTTGCCTTA | TGTCAAGGCA | 1440 |
| AGAAATCAAA | CCTGGAAAGC | TCTCAGAAGT | CAGATTTATT | GAAACTATGG | ATCAAAATTT | 1500 |
| GGTCTATTAC | CTTTCGTGGT | ATAAGTTCTG | GACAAACACA | AACTGAAAAC | TTTGGTTTAC | 1560 |
| TTGAGGCCAT | CATTCAAGGT | AGTTTAGTTG | AACTTGACAG | AGAATTCTGG | AAGTTATTTA | 1620 |
| CTGGCTCAGC | CTGTAAACCT | TCTAGTCCTT | CAGTATGCTG | CTTGACTTTG | GCACTTAGCA | 1680 |
| TCTGTGTAGT | TCCAGATGCA | ATAAAAATGG | AACAGAACA | AAGTGTGTGT | GAAGCAAATA | 1740 |
| GAAGTTTTTC | TGTAAAGGAG | TCAATAATGA | GGTGGCTCTT | ATTCTACCAG | TTAGAGGATG | 1800 |
| ACTTAGAAGA | CAGCACAGAG | CTGCCTCCAA | TTCTTCAGCG | TAATTTTCCT | CATCTTGTAG | 1860 |
| TCGAAAAAAT | TCTTGTAAGT | CTCACTATGA | AAAACTCAAA | AGCTGCAATG | AAGTTTTTTC | 1920 |
| AAAGTGTGCC | AGAATGTGAA | CAACACTGCG | AAGATAAAGA | AGAGCCTTCA | TTTTCAGAAG | 1980 |
| TAGAAGAACT | GTTTCTTCAG | ACTACTTTTG | ACAAGATGGA | TTTTTTAACT | ACTGTCAAAG | 2040 |
| AGTATGCTGT | AGAAAAATTT | CAGTCTAGTG | TTGGCTTCTC | TGTCCAGCAA | AATCTCAAGG | 2100 |

```
AATCATTGGA TCACTATCTT CTGGGATTAT CAGAACAGCT TTTAAGTAAT TACTCTTCTG    2160

AGATTACAAG TTCTGAAACC CTTGTCCGGT GTTCAAGTCT TTTGGTGGGT GTTCTTGGCT    2220

GCTATTGTTA CATGGGTATA ATAACTGAAG ACGAAGCCCA TAAATCAGAA TTATTCCAGA    2280

AAGCCAAGTC TCTGATGCAA TGTGCAGGAG AAAGTATCTC TCTGTTTAAA AATAAAACAA    2340

ATGAGGAATC AAGAATTGGT TCATTGAGAA ATGTGATGCA TCTGTGTACA AGTTGCTTGT    2400

GTATACATAC CAAGCATACG CCAAACAAGA TTGCCTCTGG CTTTTTCCTA CGATTATTAA    2460

CATCAAAGCT TATGAATGAC ATTGCAGATA TTTGTAAAAG TTTAGCATCC TGTACGAAAA    2520

AGCCATTGGA TCACGGAGTA CATCCAGGGG AAGATGATGA AGATGGTGGT GGTTGTGACA    2580

GTCTGATGGA GGCAGAGGGT CCATCGTCCA CTGGTCTTTC TACTGCTTAC CCCGCTAGTT    2640

CTGTGAGCGA TGCAAATGAT TATGGAGAGA ACCAGAATGC TGTTGGTGCC ATGAGTCCTT    2700

TAGCTGCCGA CTACCTGTCC AAACAAGATC ATCTTCTCTT AGACATGCTC AGGTTCTTAG    2760

GCCGATCTGT AACTGCATCT CAGAGCCATA CTGTGTCGTT TAGAGGAGCT GACATTAGAA    2820

GAAAATTGTT ACTGTTGCTT GATTCTAGCA TACTCGATCT CATGAAGCCC CTCCACCTGC    2880

ATATGTACTT AGTGCTCCTG AAGGATCTCC CTGGAAACGA GCACTCATTG CCAATGGAAG    2940

ATGTTGTTGA ACTTCTGCAA CCATTATCCC TTGTGTGTTC TCTGCACCGA CGTGACCAAG    3000

ATGTCTGTAA AACGATTCTA AGCAATGTCC TTCATATAGT GACAAACCTA GGCCAGGGCA    3060

GTGTGGACAT GGAGAGCACA CGGATTGCTC AAGGACACTT CCTGACAGTG ATGGGAGCAT    3120

TTTGGCATTT GACAAAGGAA AAGAAATGTG TATTCTCTGT AAGAATGGCA TTAGTAAAGT    3180

GTCTTCAAAC ATTGCTTGAG GCTGATCCAT ATTCCGAATG GGCAATTCTT AATGTAAAAG    3240

GACAAGACTT TCCTGTAAAT GAAGCTTTTT CACAATTTCT TGCTGACGAT CATCATCAAG    3300

TTCGGATGTT GGCTGCAGGG TCAGTCAACA GATTATTTCA GGATATGAGA CAAGGCGATT    3360

TCTCCAGAAG CTTGAAAGCA CTCCCTCTGA AGTTTCAGCA GACATCTTTT AACAATGCAT    3420

ACACGACAGC AGAGGCGGGG ATCAGAGGAC TGTTATGTGA TTCTCAGAAC CCTGATCTGC    3480

TGGATGAGAT CTATAACAGA AAATCTGTAC TACTGATGAT GATAGCTGTG GTCTTGCACT    3540

GTAGCCCAGT CTGTGAAAAG CAGGCTTTGT TTGCTTTATG CAAGTCTGTG AAGGAAAACA    3600

GACTAGAACC TCATCTTGTG AAAAAGGTTT TAGAGAAAGT CTCCGAATCG TTTGGATGTA    3660

GAAGTTTAGA AGACTTCATG ATTTCTCACC TAGACTACCT GGTTTTGGAA TGGCTGAACC    3720

TTCAAGATAC TGAATATAGC TTATCTTCTT TTCCTTTTAT GTTATTAAAC TACACAAGCA    3780

TTGAGGATTT CTATCGGTCT TGTTACAAGA TTTTGATCCC ACATTGGTA ATCAGAAGCC     3840

ATTTTGATGA GGTGAAGTCC ATTGCTAATC AGATTCAAAA GTGCTGGAAA AGCCTGTTGG    3900

TAGATTGCTT TCCGAAGATT CTTGTGCACA TCCTTCCTTA CTTTGCCTAC GAGGGCACGA    3960

GAGACAGCTA CGTGTCACAG AAAAGAGAGA CTGCTACCAA GGTCTACGAT ACTCTTAAAG    4020

GGAAGACTT  CCTAGGAAAA CAGATTGACC AAGTATTCAT TAGTAATTTG CCAGAGATTG    4080

TGGTGGAGTT GCTGATGACA TTGCATGAGA CAGCTGACTC GGCTGACTCG GACGCCAGTC    4140

AAAGCGCCAC CGCCTTGTGT GATTTTTCAG GGGATTTGGA TCCTGCCCCC AACCCGCCAT    4200

ATTTCCCCTC ACATGTCATT CAGGCAACGT TTGCTTACAT CAGCAACTGT CATAAAACCA    4260

AGTTTAAAAG CATTCTAGAA ATTCTTTCTA AAATCCCCGA TTCCTATCAG AAAATACTTC    4320

TGGCCATTTG TGAACAAGCA GCTGAGACAA ATAATGTCTT TAAAAAGCAC AGAATTCTTA    4380

AAATATATCA CCTGTTTGTT AGTTTATTAC TGAAAGATAT ACAGAGTGGC CTGGGAGGGG    4440
```

```
                                              -continued

CTTGGGCCTT TGTCCTTCGC GATGTTATTT ATACTCTGAT TCACTACATC AACAAAAGGT   4500

CTTCTCATTT CACAGATGTG TCGTTGCGTA GCTTTTCCCT TTGCTGTGAC CTATTAAGTC   4560

GAGTTTGTCA TACAGCTGTA ACTCAATGTA AGGATGCTCT AGAAAGCCAT CTTCACGTTA   4620

TCGTTGGCAC ACTTATTCCC CTTGTGGATT ATCAGGAAGT TCAAGAACAG GTATTGGACC   4680

TGTTGAAGTA CTTAGTGATA GATAACAAAG ACAATAAAAA CCTCTCTGTC ACAATTAAGC   4740

TTTTGGATCC CTTTCCTGAC CATGTTATTT TTAAGGACTT GCGTCTTACT CAACAGAAAA   4800

TCAAATATAG TGGAGGACCT TTTTCACTCT TAGAGGAAAT AAACCATTTT CTCTCAGTAA   4860

GTGCTTACAA TCCACTTCCG CTGACCAGGC TTGAAGGACT GAAGGATCTT CGAAGACAAC   4920

TGGAGCAACA TAAAGATCAG ATGCTAGATC TTCTGAGAGC GTCTCAAGAT AACCCACAAG   4980

ATGGCATTGT GGTGAAGCTA GTTGTCAGCT TGTTGCAGTT ATCCAAGATG GCAGTGAACC   5040

AGACTGGTGA AAGAGAAGTT TTAGAGGCTG TCGGAAGGTG TTTGGGAGAA ATAGGTCCTC   5100

TGGATTTCTC CACCATAGCT GTCCAGCATA ACAAAGATGT GTCCTATACC AAAGCCTACG   5160

GGTTACCTGA AGACAGAGAA CTTCAGTGGA CCTTGATAAT GCTGACTGCC CTCAACAATA   5220

CCCTGGTAGA GGACAGTGTC AAAATTCGAT CTGCTGCTGC TACCTGTTTG AAAAACATTT   5280

TGGCTACAAA GATTGGACAT ATTTTCTGGG AGAATTATAA GACATCAGCG GATCCAATGC   5340

TGACCTATCT ACAACCTTTT AGAACATCGA GGAAAAAGTT TTTAGAAGTG CCCCGATCTG   5400

TTAAAGAAGA TGTTTTAGAA GGCCTGGATG CTGTGAATCT GTGGGTTCCT CAAAGTGAAA   5460

GTCATGACAT TTGGATAAAG ACACTGACGT GTGCCTTTCT GGACAGTGGA GGCATAAACA   5520

GTGAAATTCT CCAGTTATTA AAGCCAATGT GTGAAGTGAA AACCGACTTC TGTCAGATGT   5580

TGCTGCCATA CTTGATCCAT GATGTTTTAC TGCAAGATAC ACATGAATCG TGGAGAACTC   5640

TGCTGTCTGC GCACGTCCGA GGATTTTTCA CTAGTTGTTT TAAGCATTCC TCCCAAGCAA   5700

GCCGCTCAGC AACTCCTGCA AATTCGGATT CAGAGTCAGA GAACTTTCTC CGATGCTGTT   5760

TGGATAAAAA GTCACAAAGA ACCATGCTTG CTGTTGTCGA CTATCTGAGA AGGCAAAAGA   5820

GACCTTCCTC GGGAACAGCT TTTGATGACG CTTTCTGGCT GGATTTGAAT TATCTTGAGG   5880

TTGCGAAGGT GGCTCAGTCC TGCTCTGCTC ACTTCACGGC CTTGCTCTAC GCAGAGATCT   5940

ATTCAGATAA GAAAAGCACA GACGAGCAAG AGAAAGAAG TCCAACATTT GAAGAAGGAA   6000

GTCAAGGAAC AACTATTTCT AGTTTGAGTG AAAAAAGTAA AGAAGAAACT GGAATAAGCT   6060

TACAGGATCT TCTCTTAGAG ATCTACAGAA GTATAGGAGA GCCGGACAGC CTGTATGGCT   6120

GTGGAGGAGG GAAAATGTTA CAACCCCTTA CTAGAATACG GACATATGAA CATGAAGCTA   6180

CGTGGGAGAA AGCCTTAGTA ACTTACGACC TGGAGACCAG CATCTCCTCC TCCACCCGCC   6240

AGTCAGGAAT CATCCAGGCC CTGCAGAATT TGGGGCTCTC CCATATCCTG TCTGTCTATC   6300

TGAAAGGATT AGACTATGAA AGACGAGAGT GGTGCGCTGA GCTGCAGGAG CTGCGTTACC   6360

AGGCGGCGTG GAGGAACATG CAGTGGGCC TCTGCGCTTC TGCCGGCCAA GAAGTAGAAG   6420

GAACCAGTTA CCATGAATCG TTGTATAATG CTCTGCAGTG TCTAAGAAAC AGAGAATTCT   6480

CCACATTTTA TGAAAGTCTC CGATATGCCA GTCTTTTCAG GGTGAAAGAA GTTGAAGAGT   6540

TGAGTAAGGG CAGCCTTGAG TCTGTATATT CGCTGTATCC CACACTTAGT AGATTGCAGG   6600

CAATTGGAGA ACTGGAAAAC AGTGGCGAGC TTTTCTCAAG GTCAGTCACA GACAGAGAGC   6660

GCTCTGAAGC ATACTGGAAG TGGCAGAAGC ACTCCCAGCT TCTGAAAGAC AGCGACTTCA   6720

GCTTTCAGGA GCCTCTCATG GCTCTGCGCA CAGTCATTCT GGAGACCCTG GTACAGAAGG   6780

AAATGGAGCG CTCTCAAGGA GCATGCTCTA AGGACATTCT CACCAAACAC CTCGTTGAAT   6840
```

-continued

```
TCTCTGTTCT GGCTCGAACC TTCAAGAACA CACAGCTCCC TGAAAGAGCA ATATTCAAAA     6900

TTAAGCAATA TAATTCAGCT ATTTGTGGAA TTTCTGAGTG GCATTTGGAA GAAGCACAAG     6960

TATTCTGGGC AAAAAAGGAG CAGAGTCTTG CTCTGAGTAT TCTCAAGCAG ATGATCAAGA     7020

AGTTGGACTC CAGCTTTAAA GATAAAGAGA ATGATGCAGG TCTCAAAGTC ATATACGCAG     7080

AGTGTCTGAG GGTTTGTGGC AGCTGGCTGG CAGAAACTTG CTTAGAAAAC CCTGCAGTCA     7140

TCATGCAGAC CTATCTAGAA AAGGCGGTGA AGGTTGCTGG AAGTTACGAT GGCAACAGCA     7200

GAGAGCTCAG AAATGGACAG ATGAAGGCCT TTCTCTCGTT GGCAAGGTTC TCTGATACTC     7260

AGTACCAGAG AATTGAAAAC TACATGAAGT CATCAGAATT TGAAAACAAG CAAACTCTCT     7320

TAAAAAGAGC CAAAGAGGAA GTGGGCCTTC TAAGGGAACA TAAAATTCAG ACCAACAGAT     7380

ACACAGTAAA GGTTCAGCGA GAACTGGAGC TGGACGAATG TGCTCTCCGT GCACTGAGAG     7440

AGGATCGCAA GCGCTTCCTG TGTAAAGCAG TGGAGAACTA CATCAACTGC TTACTAAGCG     7500

GGGAAGAACA TGATCTGTGG GTGTTCCGGC TTTGCTCCCT CTGGCTTGAA AATTCTGGAG     7560

TTTCTGAAGT CAATGGCATG ATGAAGAAAG ATGGAATGAA GATTTCATCC TATAAGTTTT     7620

TGCCTCTCAT GTATCAATTG GCTGCTCGAA TGGGGACCAA AATGACGGGA GGCCTAGGAT     7680

TTCACGAAGT CCTCAATAAT CTAATCTCTA GGATTTCACT GGATCACCCC CATCATACTT     7740

TGTTCATTAT ACTGGCCTTA GCAAATGCGA ACAAAGATGA ATTTTGAGC AAACCAGAGA     7800

CAACAAGAAG GAGTCGAATA ACCAAAAGTA CATCTAAAGA AAACTCTCAC CTTGATGAGG     7860

ATCGAACAGA GGCTGCAACC AGAATCATCC ACTCCATCAG AAGTAAGCGA TGTAAGATGG     7920

TGAAGGACAT GGAGGCGCTC TGCGATGCCT ACATCATCTT GGCAAACATG GACGCCTCTC     7980

AGTGGAGGGC TCAGAGAAAA GGCATCAATA TTCCAGCCAA CCAGCCAATC ACTAAACTGA     8040

AGAATTTAGA AGATGTTGTT GTTCCCACTA TGGAAATTAA GGTTGATCCC ACAGGAGAGT     8100

ATGAAAATCT GGTGACTATA AAATCATTTA AAACAGAATT TCGCTTAGCT GGAGGCTTAA     8160

ATTTACCCAA AATAATAGAT TGTGTGGGTT CTGATGGCAA GGAAAGGAGA CAGCTTGTGA     8220

AGGGCCGTGA TGACCTGAGG CAAGATGCTG TCATGCAGCA GGTCTTCCAG ATGTGCAATA     8280

CACTACTGCA GAGAAACACT GAGACTAGAA AGAGGAAACT GACTATCTGC ACATACAAGG     8340

TGGTTCCCCT TTCTCAGCGA AGCGGTGTTC TCGAGTGGTG CACAGGAACC GTTCCTATTG     8400

GTGAATATCT TGTTAACAGC GAAGACGGTG CACATAGAAG ATACAGGCCA AATGATTTCA     8460

GTGCCAATCA GTGCCAAAAG AAAATGATGG AAGTGCAGAA GAAGTCTTTT GAAGAGAAAT     8520

ATGATACCTT CATGACGATT TGCCAAAACT TTGAACCAGT TTTCCGTTAC TTCTGCATGG     8580

AAAAATTCTT GGACCCAGCT GTTTGGTTTG AGAAACGATT GGCATATACA CGCAGTGTGG     8640

CCACATCTTC TATCGTCGGT TACATCCTTG GACTTGGCGA CAGGCACGTA CAGAATATCT     8700

TGATAAACGA GCAGTCGGCA GAGCTTGTGC ACATAGACCT GGGAGTGGCT TTTGAACAGG     8760

GGAAGATCCT TCCCACTCCA GAAACAGTTC CTTTTAGACT CAGCAGAGAT ATTGTGGACG     8820

GGATGGGCAT CACCGGTGTG GAAGGTGTCT TCAGAAGGTG CTGTGAAAAA ACGATGGAAG     8880

TTATGCGGAG TTCTCAGGAA ACCCTGCTGA CCATTGTAGA GGTTCTTTTG TACGATCCAC     8940

TCTTTGATTG GACTATGAAT CCTTTAAAAG CTCTGTATCT ACAGCAGAGA CCAGAAGATG     9000

AGTCCGACCT CCATTCCACC CCCAATGCAG ATGATCAAGA ATGCAAACAA AGTCTTAGTG     9060

ATACTGACCA GAGTTTCAAC AAAGTAGCTG AGCGTGTCTT GATGAGACTG CAAGAGAAAC     9120

TGAAAGGCGT GGAGGAAGGC ACTGTGCTCA GTGTGGGTGG ACAGGTGAAC TTGCTTATCC     9180
```

```
AGCAGGCCAT GGATCCCAAA AATCTCAGCC GACTCTTCCC AGGATGGAAA GCTTGGGTGT    9240

GACCTTCACC CTTAAACTCG AACTTCAGAA ATGACATCTC ACCCACCATA TTTGGACAGG    9300

AATTACTTAA GTGAATAACT GCTTTTGATC CAATTTTCTA CTTGACTGAT CACCACCTAA    9360

ATATTAGTAT TTCTACTCTC TTCTGTTAGA GGTAATGGTC ACTCAAGATC CATTCGTAGG    9420

ATACGTGCTG ACTCTTAGGT CATGCTTGTG CTACTGCAGC AAGACCGCCG CATACACACT    9480

GAACTGCAAA TGGTGGGGGC AGCAGAGTGA GCTTTACTGC TGGTGTACAT GAAGACAAGT    9540

TCGTAACTTC TGCTCTAAAA CAACCTTTAA TTAAAGCATG TTTTCCAGAC TGTGTGTGTG    9600

TGTGTGTGTG TGTGTGTGTG                                                9620
```

(2) INFORMATION FOR SEQ ID NO:12:

(i) SEQUENCE CHARACTERISTICS:
        (A) LENGTH: 3066 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Mus musculus (xi) SEQUENCE DESCRIPTION: SEQ ID NO:12:

```
Met Ser Leu Ala Leu Asn Asp Leu Leu Ile Cys Cys Arg Gln Leu Glu
1               5                   10                  15

His Asp Arg Ala Thr Glu Arg Arg Lys Glu Val Asp Lys Phe Lys Arg
            20                  25                  30

Leu Ile Gln Asp Pro Glu Thr Val Gln His Leu Asp Arg His Ser Asp
        35                  40                  45

Ser Lys Gln Gly Lys Tyr Leu Asn Trp Asp Ala Val Phe Arg Phe Leu
50                  55                  60

Gln Lys Tyr Ile Gln Lys Glu Met Glu Ser Leu Arg Thr Ala Lys Ser
65                  70                  75                  80

Asn Val Ser Ala Thr Thr Gln Ser Ser Arg Gln Lys Lys Met Gln Glu
                85                  90                  95

Ile Ser Ser Leu Val Arg Tyr Phe Ile Lys Cys Ala Asn Lys Arg Ala
            100                 105                 110

Pro Arg Leu Lys Cys Gln Asp Leu Leu Asn Tyr Val Met Asp Thr Val
        115                 120                 125

Lys Asp Ser Ser Asn Gly Leu Thr Tyr Gly Ala Asp Cys Ser Asn Ile
130                 135                 140

Leu Leu Lys Asp Ile Leu Ser Val Arg Lys Tyr Trp Cys Glu Val Ser
145                 150                 155                 160

Gln Gln Gln Trp Leu Glu Leu Phe Ser Leu Tyr Phe Arg Leu Tyr Leu
                165                 170                 175

Lys Pro Ser Gln Asp Ile Asn Arg Val Leu Val Ala Arg Ile Ile His
            180                 185                 190

Ala Val Thr Arg Gly Cys Cys Ser Gln Thr Asp Gly Leu Pro Ser Lys
        195                 200                 205

Phe Leu Asp Leu Phe Ser Lys Ala Ile Gln Tyr Ala Arg Gln Glu Lys
210                 215                 220

Ser Ser Pro Gly Leu Ser His Ile Leu Ala Ala Leu Asn Ile Phe Leu
225                 230                 235                 240

Lys Ser Leu Ala Val Asn Phe Arg Lys Arg Val Cys Glu Ala Gly Asp
                245                 250                 255
```

-continued

```
Glu Ile Leu Pro Thr Leu Leu Tyr Ile Trp Thr Gln His Arg Leu Asn
            260                 265                 270

Asp Ser Leu Lys Glu Val Ile Ile Glu Leu Ile Gln Leu Gln Ile Tyr
        275                 280                 285

Ile His His Pro Gln Gly Ala Arg Ala Pro Glu Glu Gly Ala Tyr Glu
    290                 295                 300

Ser Met Lys Trp Lys Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Ser
                325                 330                 335

Arg Asn Ile Ala Val Lys Glu Asn Leu Ile Asp Leu Met Ala Asp Ile
            340                 345                 350

Cys Tyr Gln Leu Phe Asp Ala Asp Thr Arg Ser Val Glu Ile Ser Gln
        355                 360                 365

Ser Tyr Val Thr Gln Arg Glu Ser Thr Asp Tyr Ser Val Pro Cys Lys
    370                 375                 380

Arg Arg Lys Ile Asp Val Gly Trp Glu Val Ile Lys Asp Tyr Leu Gln
385                 390                 395                 400

Lys Ser Gln Ser Asp Phe Asp Leu Val Pro Trp Leu Gln Ile Thr Thr
                405                 410                 415

Arg Leu Ile Ser Lys Tyr Pro Ser Ser Leu Pro Asn Cys Glu Leu Ser
            420                 425                 430

Pro Leu Ile Leu Ile Leu Tyr Gln Leu Leu Pro Gln Gln Arg Arg Gly
        435                 440                 445

Glu Arg Ile Pro Tyr Val Leu Arg Cys Leu Lys Glu Val Ala Leu Cys
    450                 455                 460

Gln Gly Lys Lys Ser Asn Leu Glu Ser Ser Gln Lys Ser Asp Leu Leu
465                 470                 475                 480

Lys Leu Trp Ile Lys Ile Trp Ser Ile Thr Phe Arg Gly Ile Ser Ser
                485                 490                 495

Gly Gln Thr Gln Thr Glu Asn Phe Gly Leu Leu Glu Ala Ile Ile Gln
            500                 505                 510

Gly Ser Leu Val Glu Leu Asp Arg Glu Phe Trp Lys Leu Phe Thr Gly
        515                 520                 525

Ser Ala Cys Lys Pro Ser Ser Pro Ser Val Cys Cys Leu Thr Leu Ala
    530                 535                 540

Leu Ser Ile Cys Val Val Pro Asp Ala Ile Lys Met Gly Thr Glu Gln
545                 550                 555                 560

Ser Val Cys Glu Ala Asn Arg Ser Phe Ser Val Lys Glu Ser Ile Met
                565                 570                 575

Arg Trp Leu Leu Phe Tyr Gln Leu Glu Asp Asp Leu Glu Asp Ser Thr
            580                 585                 590

Glu Leu Pro Pro Ile Leu Gln Arg Asn Phe Pro His Leu Val Val Glu
        595                 600                 605

Lys Ile Leu Val Ser Leu Thr Met Lys Asn Ser Lys Ala Ala Met Lys
    610                 615                 620

Phe Phe Gln Ser Val Pro Glu Cys Glu Gln His Cys Glu Asp Lys Glu
625                 630                 635                 640

Glu Pro Ser Phe Ser Glu Val Glu Glu Leu Phe Leu Gln Thr Thr Phe
                645                 650                 655

Asp Lys Met Asp Phe Leu Thr Thr Val Lys Glu Tyr Ala Val Glu Lys
            660                 665                 670
```

-continued

```
Phe Gln Ser Ser Val Gly Phe Ser Val Gln Gln Asn Leu Lys Glu Ser
            675                 680                 685

Leu Asp His Tyr Leu Leu Gly Leu Ser Glu Gln Leu Leu Ser Asn Tyr
        690                 695                 700

Ser Ser Glu Ile Thr Ser Ser Glu Thr Leu Val Arg Cys Ser Ser Leu
705                 710                 715                 720

Leu Val Gly Val Leu Gly Cys Tyr Cys Tyr Met Gly Ile Ile Thr Glu
                725                 730                 735

Asp Glu Ala His Lys Ser Glu Leu Phe Gln Lys Ala Lys Ser Leu Met
            740                 745                 750

Gln Cys Ala Gly Glu Ser Ile Ser Leu Phe Lys Asn Lys Thr Asn Glu
        755                 760                 765

Glu Ser Arg Ile Gly Ser Leu Arg Asn Val Met His Leu Cys Thr Ser
770                 775                 780

Cys Leu Cys Ile His Thr Lys His Thr Pro Asn Lys Ile Ala Ser Gly
785                 790                 795                 800

Phe Phe Leu Arg Leu Leu Thr Ser Lys Leu Met Asn Asp Ile Ala Asp
                805                 810                 815

Ile Cys Lys Ser Leu Ala Ser Cys Thr Lys Lys Pro Leu Asp His Gly
            820                 825                 830

Val His Pro Gly Glu Asp Asp Glu Asp Gly Gly Cys Asp Ser Leu
        835                 840                 845

Met Glu Ala Glu Gly Pro Ser Ser Thr Gly Leu Ser Thr Ala Tyr Pro
850                 855                 860

Ala Ser Ser Val Ser Asp Ala Asn Asp Tyr Gly Glu Asn Gln Asn Ala
865                 870                 875                 880

Val Gly Ala Met Ser Pro Leu Ala Ala Asp Tyr Leu Ser Lys Gln Asp
                885                 890                 895

His Leu Leu Leu Asp Met Leu Arg Phe Leu Gly Arg Ser Val Thr Ala
            900                 905                 910

Ser Gln Ser His Thr Val Ser Phe Arg Gly Ala Asp Ile Arg Arg Lys
        915                 920                 925

Leu Leu Leu Leu Leu Asp Ser Ser Ile Leu Asp Leu Met Lys Pro Leu
930                 935                 940

His Leu His Met Tyr Leu Val Leu Leu Lys Asp Leu Pro Gly Asn Glu
945                 950                 955                 960

His Ser Leu Pro Met Glu Asp Val Val Glu Leu Leu Gln Pro Leu Ser
                965                 970                 975

Leu Val Cys Ser Leu His Arg Arg Asp Gln Asp Val Cys Lys Thr Ile
            980                 985                 990

Leu Ser Asn Val Leu His Ile Val Thr Asn Leu Gly Gln Gly Ser Val
        995                 1000                1005

Asp Met Glu Ser Thr Arg Ile Ala Gln Gly His Phe Leu Thr Val Met
    1010                1015                1020

Gly Ala Phe Trp His Leu Thr Lys Glu Lys Cys Val Phe Ser Val
1025                1030                1035                1040

Arg Met Ala Leu Val Lys Cys Leu Gln Thr Leu Leu Glu Ala Asp Pro
                1045                1050                1055

Tyr Ser Glu Trp Ala Ile Leu Asn Val Lys Gly Gln Asp Phe Pro Val
            1060                1065                1070

Asn Glu Ala Phe Ser Gln Phe Leu Ala Asp Asp His Gln Val Arg
        1075                1080                1085

Met Leu Ala Ala Gly Ser Val Asn Arg Leu Phe Gln Asp Met Arg Gln
```

-continued

```
         1090                1095                1100
Gly Asp Phe Ser Arg Ser Leu Lys Ala Leu Pro Leu Lys Phe Gln Gln
1105                1110                1115                1120

Thr Ser Phe Asn Asn Ala Tyr Thr Thr Ala Glu Ala Gly Ile Arg Gly
                1125                1130                1135

Leu Leu Cys Asp Ser Gln Asn Pro Asp Leu Leu Asp Glu Ile Tyr Asn
            1140                1145                1150

Arg Lys Ser Val Leu Leu Met Met Ile Ala Val Val Leu His Cys Ser
        1155                1160                1165

Pro Val Cys Glu Lys Gln Ala Leu Phe Ala Leu Cys Lys Ser Val Lys
    1170                1175                1180

Glu Asn Arg Leu Glu Pro His Leu Val Lys Lys Val Leu Glu Lys Val
1185                1190                1195                1200

Ser Glu Ser Phe Gly Cys Arg Ser Leu Glu Asp Phe Met Ile Ser His
                1205                1210                1215

Leu Asp Tyr Leu Val Leu Glu Trp Leu Asn Leu Gln Asp Thr Glu Tyr
            1220                1225                1230

Ser Leu Ser Ser Phe Pro Phe Met Leu Leu Asn Tyr Thr Ser Ile Glu
        1235                1240                1245

Asp Phe Tyr Arg Ser Cys Tyr Lys Ile Leu Ile Pro His Leu Val Ile
    1250                1255                1260

Arg Ser His Phe Asp Glu Val Lys Ser Ile Ala Asn Gln Ile Gln Lys
1265                1270                1275                1280

Cys Trp Lys Ser Leu Leu Val Asp Cys Phe Pro Lys Ile Leu Val His
                1285                1290                1295

Ile Leu Pro Tyr Phe Ala Tyr Glu Gly Thr Arg Asp Ser Tyr Val Ser
            1300                1305                1310

Gln Lys Arg Glu Thr Ala Thr Lys Val Tyr Asp Thr Leu Lys Gly Glu
        1315                1320                1325

Asp Phe Leu Gly Lys Gln Ile Asp Gln Val Phe Ile Ser Asn Leu Pro
    1330                1335                1340

Glu Ile Val Val Glu Leu Leu Met Thr Leu His Glu Thr Ala Asp Ser
1345                1350                1355                1360

Ala Asp Ser Asp Ala Ser Gln Ser Ala Thr Ala Leu Cys Asp Phe Ser
                1365                1370                1375

Gly Asp Leu Asp Pro Ala Pro Asn Pro Pro Tyr Phe Pro Ser His Val
            1380                1385                1390

Ile Gln Ala Thr Phe Ala Tyr Ile Ser Asn Cys His Lys Thr Lys Phe
        1395                1400                1405

Lys Ser Ile Leu Glu Ile Leu Ser Lys Ile Pro Asp Ser Tyr Gln Lys
    1410                1415                1420

Ile Leu Leu Ala Ile Cys Glu Gln Ala Ala Glu Thr Asn Asn Val Phe
1425                1430                1435                1440

Lys Lys His Arg Ile Leu Lys Ile Tyr His Leu Phe Val Ser Leu Leu
                1445                1450                1455

Leu Lys Asp Ile Gln Ser Gly Leu Gly Gly Ala Trp Ala Phe Val Leu
            1460                1465                1470

Arg Asp Val Ile Tyr Thr Leu Ile His Tyr Ile Asn Lys Arg Ser Ser
        1475                1480                1485

His Phe Thr Asp Val Ser Leu Arg Ser Phe Ser Leu Cys Cys Asp Leu
    1490                1495                1500

Leu Ser Arg Val Cys His Thr Ala Val Thr Gln Cys Lys Asp Ala Leu
1505                1510                1515                1520
```

-continued

```
Glu Ser His Leu His Val Ile Val Gly Thr Leu Ile Pro Leu Val Asp
                1525                1530                1535

Tyr Gln Glu Val Gln Glu Gln Val Leu Asp Leu Leu Lys Tyr Leu Val
            1540                1545                1550

Ile Asp Asn Lys Asp Asn Lys Asn Leu Ser Val Thr Ile Lys Leu Leu
            1555                1560                1565

Asp Pro Phe Pro Asp His Val Ile Phe Lys Asp Leu Arg Leu Thr Gln
            1570                1575                1580

Gln Lys Ile Lys Tyr Ser Gly Pro Phe Ser Leu Leu Glu Glu Ile
1585                1590                1595                1600

Asn His Phe Leu Ser Val Ser Ala Tyr Asn Pro Leu Pro Leu Thr Arg
            1605                1610                1615

Leu Glu Gly Leu Lys Asp Leu Arg Arg Gln Leu Glu Gln His Lys Asp
            1620                1625                1630

Gln Met Leu Asp Leu Leu Arg Ala Ser Gln Asp Asn Pro Gln Asp Gly
            1635                1640                1645

Ile Val Val Lys Leu Val Val Ser Leu Leu Gln Leu Ser Lys Met Ala
            1650                1655                1660

Val Asn Gln Thr Gly Glu Arg Glu Val Leu Glu Ala Val Gly Arg Cys
1665                1670                1675                1680

Leu Gly Glu Ile Gly Pro Leu Asp Phe Ser Thr Ile Ala Val Gln His
            1685                1690                1695

Asn Lys Asp Val Ser Tyr Thr Lys Ala Tyr Gly Leu Pro Glu Asp Arg
            1700                1705                1710

Glu Leu Gln Trp Thr Leu Ile Met Leu Thr Ala Leu Asn Asn Thr Leu
            1715                1720                1725

Val Glu Asp Ser Val Lys Ile Arg Ser Ala Ala Ala Thr Cys Leu Lys
            1730                1735                1740

Asn Ile Leu Ala Thr Lys Ile Gly His Ile Phe Trp Glu Asn Tyr Lys
1745                1750                1755                1760

Thr Ser Ala Asp Pro Met Leu Thr Tyr Leu Gln Pro Phe Arg Thr Ser
            1765                1770                1775

Arg Lys Lys Phe Leu Glu Val Pro Arg Ser Val Lys Glu Asp Val Leu
            1780                1785                1790

Glu Gly Leu Asp Ala Val Asn Leu Trp Val Pro Gln Ser Glu Ser His
            1795                1800                1805

Asp Ile Trp Ile Lys Thr Leu Thr Cys Ala Phe Leu Asp Ser Gly Gly
            1810                1815                1820

Ile Asn Ser Glu Ile Leu Gln Leu Leu Lys Pro Met Cys Glu Val Lys
1825                1830                1835                1840

Thr Asp Phe Cys Gln Met Leu Leu Pro Tyr Leu Ile His Asp Val Leu
            1845                1850                1855

Leu Gln Asp Thr His Glu Ser Trp Arg Thr Leu Leu Ser Ala His Val
            1860                1865                1870

Arg Gly Phe Phe Thr Ser Cys Phe Lys His Ser Ser Gln Ala Ser Arg
            1875                1880                1885

Ser Ala Thr Pro Ala Asn Ser Asp Ser Glu Ser Glu Asn Phe Leu Arg
            1890                1895                1900

Cys Cys Leu Asp Lys Lys Ser Gln Arg Thr Met Leu Ala Val Val Asp
1905                1910                1915                1920

Tyr Leu Arg Arg Gln Lys Arg Pro Ser Ser Gly Thr Ala Phe Asp Asp
            1925                1930                1935
```

-continued

```
Ala Phe Trp Leu Asp Leu Asn Tyr Leu Glu Val Ala Lys Val Ala Gln
            1940                1945                1950

Ser Cys Ser Ala His Phe Thr Ala Leu Leu Tyr Ala Glu Ile Tyr Ser
            1955                1960                1965

Asp Lys Lys Ser Thr Asp Glu Gln Glu Lys Arg Ser Pro Thr Phe Glu
            1970                1975                1980

Glu Gly Ser Gln Gly Thr Thr Ile Ser Ser Leu Ser Glu Lys Ser Lys
1985                1990                1995                2000

Glu Glu Thr Gly Ile Ser Leu Gln Asp Leu Leu Leu Glu Ile Tyr Arg
                2005                2010                2015

Ser Ile Gly Glu Pro Asp Ser Leu Tyr Gly Cys Gly Gly Lys Met
            2020                2025                2030

Leu Gln Pro Leu Thr Arg Ile Arg Thr Tyr Glu His Glu Ala Thr Trp
            2035                2040                2045

Glu Lys Ala Leu Val Thr Tyr Asp Leu Glu Thr Ser Ile Ser Ser Ser
            2050                2055                2060

Thr Arg Gln Ser Gly Ile Ile Gln Ala Leu Gln Asn Leu Gly Leu Ser
2065                2070                2075                2080

His Ile Leu Ser Val Tyr Leu Lys Gly Leu Asp Tyr Glu Arg Arg Glu
                2085                2090                2095

Trp Cys Ala Glu Leu Gln Glu Leu Arg Tyr Gln Ala Ala Trp Arg Asn
            2100                2105                2110

Met Gln Trp Gly Leu Cys Ala Ser Ala Gly Gln Glu Val Glu Gly Thr
            2115                2120                2125

Ser Tyr His Glu Ser Leu Tyr Asn Ala Leu Gln Cys Leu Arg Asn Arg
            2130                2135                2140

Glu Phe Ser Thr Phe Tyr Glu Ser Leu Arg Tyr Ala Ser Leu Phe Arg
2145                2150                2155                2160

Val Lys Glu Val Glu Glu Leu Ser Lys Gly Ser Leu Glu Ser Val Tyr
            2165                2170                2175

Ser Leu Tyr Pro Thr Leu Ser Arg Leu Gln Ala Ile Gly Glu Leu Glu
            2180                2185                2190

Asn Ser Gly Glu Leu Phe Ser Arg Ser Val Thr Asp Arg Glu Arg Ser
            2195                2200                2205

Glu Ala Tyr Trp Lys Trp Gln Lys His Ser Gln Leu Leu Lys Asp Ser
            2210                2215                2220

Asp Phe Ser Phe Gln Glu Pro Leu Met Ala Leu Arg Thr Val Ile Leu
2225                2230                2235                2240

Glu Thr Leu Val Gln Lys Glu Met Glu Arg Ser Gln Gly Ala Cys Ser
                2245                2250                2255

Lys Asp Ile Leu Thr Lys His Leu Val Glu Phe Ser Val Leu Ala Arg
            2260                2265                2270

Thr Phe Lys Asn Thr Gln Leu Pro Glu Arg Ala Ile Phe Lys Ile Lys
            2275                2280                2285

Gln Tyr Asn Ser Ala Ile Cys Gly Ile Ser Glu Trp His Leu Glu Glu
            2290                2295                2300

Ala Gln Val Phe Trp Ala Lys Lys Glu Gln Ser Leu Ala Leu Ser Ile
2305                2310                2315                2320

Leu Lys Gln Met Ile Lys Lys Leu Asp Ser Ser Phe Lys Asp Lys Glu
                2325                2330                2335

Asn Asp Ala Gly Leu Lys Val Ile Tyr Ala Glu Cys Leu Arg Val Cys
            2340                2345                2350

Gly Ser Trp Leu Ala Glu Thr Cys Leu Glu Asn Pro Ala Val Ile Met
```

-continued

```
          2355                2360                2365
Gln Thr Tyr Leu Glu Lys Ala Val Lys Val Ala Gly Ser Tyr Asp Gly
        2370                2375                2380

Asn Ser Arg Glu Leu Arg Asn Gly Gln Met Lys Ala Phe Leu Ser Leu
2385                2390                2395                2400

Ala Arg Phe Ser Asp Thr Gln Tyr Gln Arg Ile Glu Asn Tyr Met Lys
            2405                2410                2415

Ser Ser Glu Phe Glu Asn Lys Gln Thr Leu Leu Lys Arg Ala Lys Glu
        2420                2425                2430

Glu Val Gly Leu Leu Arg Glu His Lys Ile Gln Thr Asn Arg Tyr Thr
            2435                2440                2445

Val Lys Val Gln Arg Glu Leu Glu Leu Asp Glu Cys Ala Leu Arg Ala
    2450                2455                2460

Leu Arg Glu Asp Arg Lys Arg Phe Leu Cys Lys Ala Val Glu Asn Tyr
2465                2470                2475                2480

Ile Asn Cys Leu Leu Ser Gly Glu Glu His Asp Leu Trp Val Phe Arg
            2485                2490                2495

Leu Cys Ser Leu Trp Leu Glu Asn Ser Gly Val Ser Glu Val Asn Gly
        2500                2505                2510

Met Met Lys Lys Asp Gly Met Lys Ile Ser Ser Tyr Lys Phe Leu Pro
        2515                2520                2525

Leu Met Tyr Gln Leu Ala Ala Arg Met Gly Thr Lys Met Thr Gly Gly
    2530                2535                2540

Leu Gly Phe His Glu Val Leu Asn Asn Leu Ile Ser Arg Ile Ser Leu
2545                2550                2555                2560

Asp His Pro His His Thr Leu Phe Ile Ile Leu Ala Leu Ala Asn Ala
            2565                2570                2575

Asn Lys Asp Glu Phe Leu Ser Lys Pro Glu Thr Thr Arg Arg Ser Arg
        2580                2585                2590

Ile Thr Lys Ser Thr Ser Lys Glu Asn Ser His Leu Asp Glu Asp Arg
            2595                2600                2605

Thr Glu Ala Ala Thr Arg Ile Ile His Ser Ile Arg Ser Lys Arg Cys
    2610                2615                2620

Lys Met Val Lys Asp Met Glu Ala Leu Cys Asp Ala Tyr Ile Ile Leu
2625                2630                2635                2640

Ala Asn Met Asp Ala Ser Gln Trp Arg Ala Gln Arg Lys Gly Ile Asn
            2645                2650                2655

Ile Pro Ala Asn Gln Pro Ile Thr Lys Leu Lys Asn Leu Glu Asp Val
        2660                2665                2670

Val Val Pro Thr Met Glu Ile Lys Val Asp Pro Thr Gly Glu Tyr Glu
        2675                2680                2685

Asn Leu Val Thr Ile Lys Ser Phe Lys Thr Glu Phe Arg Leu Ala Gly
    2690                2695                2700

Gly Leu Asn Leu Pro Lys Ile Ile Asp Cys Val Gly Ser Asp Gly Lys
2705                2710                2715                2720

Glu Arg Arg Gln Leu Val Lys Gly Arg Asp Asp Leu Arg Gln Asp Ala
            2725                2730                2735

Val Met Gln Gln Val Phe Gln Met Cys Asn Thr Leu Leu Gln Arg Asn
            2740                2745                2750

Thr Glu Thr Arg Lys Arg Lys Leu Thr Ile Cys Thr Tyr Lys Val Val
        2755                2760                2765

Pro Leu Ser Gln Arg Ser Gly Val Leu Glu Trp Cys Thr Gly Thr Val
    2770                2775                2780
```

```
Pro Ile Gly Glu Tyr Leu Val Asn Ser Glu Asp Gly Ala His Arg Arg
2785                2790                2795                2800

Tyr Arg Pro Asn Asp Phe Ser Ala Asn Gln Cys Gln Lys Lys Met Met
            2805                2810                2815

Glu Val Gln Lys Lys Ser Phe Glu Lys Tyr Asp Thr Phe Met Thr
        2820                2825                2830

Ile Cys Gln Asn Phe Glu Pro Val Phe Arg Tyr Phe Cys Met Glu Lys
        2835                2840                2845

Phe Leu Asp Pro Ala Val Trp Phe Glu Lys Arg Leu Ala Tyr Thr Arg
    2850                2855                2860

Ser Val Ala Thr Ser Ser Ile Val Gly Tyr Ile Leu Gly Leu Gly Asp
2865                2870                2875                2880

Arg His Val Gln Asn Ile Leu Ile Asn Glu Gln Ser Ala Glu Leu Val
            2885                2890                2895

His Ile Asp Leu Gly Val Ala Phe Glu Gln Gly Lys Ile Leu Pro Thr
        2900                2905                2910

Pro Glu Thr Val Pro Phe Arg Leu Ser Arg Asp Ile Val Asp Gly Met
        2915                2920                2925

Gly Ile Thr Gly Val Glu Gly Val Phe Arg Arg Cys Cys Glu Lys Thr
2930                2935                2940

Met Glu Val Met Arg Ser Ser Gln Glu Thr Leu Leu Thr Ile Val Glu
2945                2950                2955                2960

Val Leu Leu Tyr Asp Pro Leu Phe Asp Trp Thr Met Asn Pro Leu Lys
            2965                2970                2975

Ala Leu Tyr Leu Gln Gln Arg Pro Glu Asp Glu Ser Asp Leu His Ser
        2980                2985                2990

Thr Pro Asn Ala Asp Asp Gln Glu Cys Lys Gln Ser Leu Ser Asp Thr
    2995                3000                3005

Asp Gln Ser Phe Asn Lys Val Ala Glu Arg Val Leu Met Arg Leu Gln
        3010                3015                3020

Glu Lys Leu Lys Gly Val Glu Glu Gly Thr Val Leu Ser Val Gly Gly
3025                3030                3035                3040

Gln Val Asn Leu Leu Ile Gln Gln Ala Met Asp Pro Lys Asn Leu Ser
            3045                3050                3055

Arg Leu Phe Pro Gly Trp Lys Ala Trp Val
            3060                3065

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Cys Arg Gln Leu Glu His Asp Arg Ala Thr Glu Arg Arg Lys Lys Glu
1               5                   10                  15

Val Glu Lys Phe Lys
            20

(2) INFORMATION FOR SEQ ID NO:14:

(i) SEQUENCE CHARACTERISTICS:
        (A) LENGTH: 20 amino acids
```

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Cys Leu Arg Ile Ala Lys Pro Asn Val Ser Ala Ser Thr Gln Ala Ser
1               5                   10                  15

Arg Gln Lys Lys
            20

(2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Cys Ala Arg Gln Glu Lys Ser Ser Ser Gly Leu Asn His Ile Leu Ala
1               5                   10                  15

Ala (2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Cys Arg Gln Leu Glu His Asp Arg Ala Thr Glu Arg Lys Lys Glu Val
1               5                   10                  15

Asp Lys Phe (2) INFORMATION FOR SEQ ID NO:17:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Cys Phe Lys His Ser Ser Gln Ala Ser Arg Ser Ala Thr Pro Ala Asn
1               5                   10                  15

Ser Asp (2) INFORMATION FOR SEQ ID NO:18:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide
```

(xi) SEQUENCE DESCRIPTION: SEQ ID NO:18:

Arg Pro Glu Asp Glu Ser Asp Leu His Ser Thr Pro Asn Ala Asp Asp
1               5                   10                  15

Gln Glu Cys (2) INFORMATION FOR SEQ ID NO:19:

(i) SEQUENCE CHARACTERISTICS:
        (A) LENGTH: 249 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
                20                  25                  30

Leu Ile Arg Asp Pro Glu Thr Ile Lys His Leu Asp Arg His Ser Asp
            35                  40                  45

Ser Lys Gln Gly Lys Tyr Leu Asn Trp Asp Ala Val Phe Arg Phe Leu
        50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Phe Tyr Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Ile Ile His His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile
                245

(2) INFORMATION FOR SEQ ID NO:20:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:20:

```
Gly Phe Ser Val His Gln Asn Leu Lys Glu Ser Leu Asp Arg Cys Leu
1               5                   10                  15

Leu Gly Leu Ser Glu Gln Leu Leu Asn Asn Tyr Ser Ser Glu Ile Thr
            20                  25                  30

Asn Ser Glu Thr Leu Val Arg Cys Ser Arg Leu Leu Val Gly Val Leu
        35                  40                  45

Gly Cys Tyr Cys Tyr Met Gly Val Ile Ala Glu Glu Ala Tyr Lys
    50                  55                  60

Ser Glu Leu Phe Gln Lys Ala Asn Ser Leu Met Gln Cys Ala Gly Glu
65                  70                  75                  80

Ser Ile Thr Leu Phe Lys Asn Lys Thr Asn Glu Glu Phe Arg Ile Gly
                85                  90                  95

Ser Leu Arg Asn Met Met Gln Leu Cys Thr Arg Cys Leu Ser Asn Cys
                100                 105                 110

Thr Lys Lys Ser Pro Asn Lys Ile Ala Ser Gly Phe Phe Leu Arg Leu
            115                 120                 125

Leu Thr Ser Lys Leu Met Asn Asp Ile Ala Asp Ile Cys Lys Ser Leu
    130                 135                 140

Ala Ser Phe Ile Lys Lys Pro Phe Asp Arg Gly Glu Val Glu Ser Met
145                 150                 155                 160

Glu Asp Asp Thr Asn Gly Asn Leu Met Glu Val Glu Asp Gln Ser Ser
                165                 170                 175

Met Asn Leu Phe Asn Asp Tyr Pro Asp Ser Ser Val Ser Asp Ala Asn
            180                 185                 190

Glu Pro Gly Glu Ser Gln Ser Thr Ile Gly Ala Ile Asn Pro Leu Ala
        195                 200                 205

Glu Glu
    210
```

(2) INFORMATION FOR SEQ ID NO:21:

(i) SEQUENCE CHARACTERISTICS:
        (A) LENGTH: 448 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Gly Phe Ser Val His Gln Asn Leu Lys Glu Ser Leu Asp Arg Cys Leu
1               5                   10                  15

Leu Gly Leu Ser Glu Gln Leu Leu Asn Asn Tyr Ser Ser Glu Ile Thr
            20                  25                  30

Asn Ser Glu Thr Leu Val Arg Cys Ser Arg Leu Leu Val Gly Val Leu
        35                  40                  45

Gly Cys Tyr Cys Tyr Met Gly Val Ile Ala Glu Glu Ala Tyr Lys
    50                  55                  60

Ser Glu Leu Phe Gln Lys Ala Asn Ser Leu Met Gln Cys Ala Gly Glu
65                  70                  75                  80

Ser Ile Thr Leu Phe Lys Asn Lys Thr Asn Glu Glu Phe Arg Ile Gly
                85                  90                  95

Ser Leu Arg Asn Met Met Gln Leu Cys Thr Arg Cys Leu Ser Asn Cys
                100                 105                 110

Thr Lys Lys Ser Pro Asn Lys Ile Ala Ser Gly Phe Phe Leu Arg Leu
```

```
            115                 120                 125
Leu Thr Ser Lys Leu Met Asn Asp Ile Ala Asp Ile Cys Lys Ser Leu
            130                 135                 140

Ala Ser Phe Ile Lys Lys Pro Phe Asp Arg Gly Glu Val Glu Ser Met
145                 150                 155                 160

Glu Asp Asp Thr Asn Gly Asn Leu Met Glu Val Glu Asp Gln Ser Ser
                    165                 170                 175

Met Asn Leu Phe Asn Asp Tyr Pro Asp Ser Ser Val Ser Asp Ala Asn
                180                 185                 190

Glu Pro Gly Glu Ser Gln Ser Thr Ile Gly Ala Ile Asn Pro Leu Ala
            195                 200                 205

Glu Glu Tyr Leu Ser Lys Gln Asp Leu Leu Phe Leu Asp Met Leu Lys
210                 215                 220

Phe Leu Cys Leu Cys Val Thr Thr Ala Gln Thr Asn Thr Val Ser Phe
225                 230                 235                 240

Arg Ala Ala Asp Ile Arg Arg Lys Leu Leu Met Leu Ile Asp Ser Ser
                245                 250                 255

Thr Leu Glu Pro Thr Lys Ser Leu His Leu His Met Tyr Leu Met Leu
            260                 265                 270

Leu Lys Glu Leu Pro Gly Glu Glu Tyr Pro Leu Pro Met Glu Asp Val
            275                 280                 285

Leu Glu Leu Leu Lys Pro Leu Ser Asn Val Cys Ser Leu Tyr Arg Arg
290                 295                 300

Asp Gln Asp Val Cys Lys Thr Ile Leu Asn His Val Leu His Val Val
305                 310                 315                 320

Lys Asn Leu Gly Gln Ser Asn Met Asp Ser Glu Asn Thr Arg Asp Ala
                325                 330                 335

Gln Gly Gln Phe Leu Thr Val Ile Gly Ala Phe Trp His Leu Thr Lys
                340                 345                 350

Glu Arg Lys Tyr Ile Phe Ser Val Arg Met Ala Leu Val Asn Cys Leu
            355                 360                 365

Lys Thr Leu Leu Glu Ala Asp Pro Tyr Ser Lys Trp Ala Ile Leu Asn
            370                 375                 380

Val Met Gly Lys Asp Phe Pro Val Asn Glu Val Phe Thr Gln Phe Leu
385                 390                 395                 400

Ala Asp Asn His His Gln Val Arg Met Leu Ala Ala Glu Ser Ile Asn
                405                 410                 415

Arg Leu Phe Gln Asp Thr Lys Gly Asp Ser Ser Arg Leu Leu Lys Ala
                420                 425                 430

Leu Pro Leu Lys Leu Gln Gln Thr Ala Phe Glu Asn Ala Tyr Leu Lys
            435                 440                 445

(2) INFORMATION FOR SEQ ID NO:22:

(i) SEQUENCE CHARACTERISTICS:
        (A) LENGTH: 216 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Leu Gln Asp Thr Glu Tyr Asn Leu Ser Ser Phe Pro Phe Ile Leu Leu
1               5                   10                  15

Asn Tyr Thr Asn Ile Glu Asp Phe Tyr Arg Ser Cys Tyr Lys Val Leu
```

```
                  20                  25                  30
Ile Pro His Leu Val Ile Arg Ser His Phe Asp Glu Val Lys Ser Ile
            35                  40                  45
Ala Asn Gln Ile Gln Glu Asp Trp Lys Ser Leu Leu Thr Asp Cys Phe
    50                  55                  60
Pro Lys Ile Leu Val Asn Ile Leu Pro Tyr Phe Ala Tyr Glu Gly Thr
65                  70                  75                  80
Arg Asp Ser Gly Met Ala Gln Gln Arg Glu Thr Ala Thr Lys Val Tyr
                85                  90                  95
Asp Met Leu Lys Ser Glu Asn Leu Leu Gly Lys Gln Ile Asp His Leu
            100                 105                 110
Phe Ile Ser Asn Leu Pro Glu Ile Val Val Glu Leu Leu Met Thr Leu
        115                 120                 125
His Glu Pro Ala Asn Ser Ser Ala Ser Gln Ser Thr Asp Leu Cys Asp
    130                 135                 140
Phe Ser Gly Asp Leu Asp Pro Ala Pro Asn Pro Pro His Phe Pro Ser
145                 150                 155                 160
His Val Ile Lys Ala Thr Phe Ala Tyr Ile Ser Asn Cys His Lys Thr
                165                 170                 175
Lys Leu Lys Ser Ile Leu Glu Ile Leu Ser Lys Ser Pro Asp Ser Tyr
            180                 185                 190
Gln Lys Ile Leu Leu Ala Ile Cys Glu Gln Ala Ala Glu Thr Asn Asn
        195                 200                 205
Val Tyr Lys Lys His Arg Ile Leu
    210                 215

(2) INFORMATION FOR SEQ ID NO:23:

(i) SEQUENCE CHARACTERISTICS:
        (A) LENGTH: 286 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Gly Val Ser Glu Trp Gln Leu Glu Glu Ala Gln Val Phe Trp Ala Lys
1               5                   10                  15
Lys Glu Gln Ser Leu Ala Leu Ser Ile Leu Lys Gln Met Ile Lys Lys
            20                  25                  30
Leu Asp Ala Ser Cys Ala Ala Asn Asn Pro Ser Leu Lys Leu Thr Tyr
        35                  40                  45
Thr Glu Cys Leu Arg Val Cys Gly Asn Trp Leu Ala Glu Thr Cys Leu
    50                  55                  60
Glu Asn Pro Ala Val Ile Met Gln Thr Tyr Leu Glu Lys Ala Val Glu
65                  70                  75                  80
Val Ala Gly Asn Tyr Asp Gly Glu Ser Ser Asp Glu Leu Arg Asn Gly
                85                  90                  95
Lys Met Lys Ala Phe Leu Ser Leu Ala Arg Phe Ser Asp Thr Gln Tyr
            100                 105                 110
Gln Arg Ile Glu Asn Tyr Met Lys Ser Ser Glu Phe Glu Asn Lys Gln
        115                 120                 125
Ala Leu Leu Lys Arg Ala Lys Glu Glu Val Gly Leu Leu Arg Glu His
    130                 135                 140
Lys Ile Gln Thr Asn Arg Tyr Thr Val Lys Val Gln Arg Glu Leu Glu
```

```
145                 150                 155                 160
Leu Asp Glu Leu Ala Arg Leu Ala Leu Lys Glu Asp Arg Lys Arg Phe
                165                 170                 175

Leu Cys Lys Ala Val Glu Asn Tyr Ile Asn Cys Leu Leu Ser Gly Glu
                180                 185                 190

Glu His Asp Met Trp Val Phe Arg Leu Cys Ser Leu Trp Leu Glu Asn
                195                 200                 205

Ser Gly Val Ser Glu Val Asn Gly Met Met Lys Arg Asp Gly Met Lys
            210                 215                 220

Ile Pro Thr Tyr Lys Phe Leu Pro Leu Met Tyr Gln Leu Ala Ala Arg
225                 230                 235                 240

Met Gly Thr Lys Met Met Gly Gly Leu Gly Phe His Glu Val Leu Asn
                245                 250                 255

Asn Leu Ile Ser Arg Ile Ser Met Asp His Pro His His Thr Leu Phe
                260                 265                 270

Ile Ile Leu Ala Leu Ala Asn Ala Asn Arg Asp Glu Phe Leu
                275                 280                 285
```

(2) INFORMATION FOR SEQ ID NO:24:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (xi) SEQUENCE DESCRIPTION: SEQ ID NO:24:

```
TGCTTTTTTG GACAGTGGAG GCACAAAATG TGAAATTCTT CAATTATTAA AGCCAATGTG      60
TGAAGTGAAA ACTGACTTTT GTCAGACTGT ACTTCCATAC TTGATTCATG ATATTTTACT     120
CCAAGATACA AATGAATCAT GGAGAAATCT GCTTTCTACA CATGTTCAGG AATTTTTCAC     180
CAGCTGTCTT CGACACTTCT CGCAAACGAG CCGATCCACA ACCCCTGCAA ACTTGG         236
```

ATAXIA-TELANGIECTASIA GENE

CROSS REFERENCE

This application is a National Phase Application of International Application No. PCT/US96/07040, filed May 16, 1996, which is a continuation-in-part of U.S. Ser. No. 08/508,836, filed Jul. 28, 1995, now U.S. Pat. No. 5,777,093, which is a continuation-in-part of U.S. Ser. No. 08/493,092, filed Jun. 21, 1995, now U.S. Pat. No. 5,728,807 which is a continuation-in-part of U.S. Ser. No. 08/441,822, filed May 16, 1995, now U.S. Pat. No. 5,756,288.

TECHNICAL FIELD

The present invention relates to the determination of the gene sequence, mutations of which cause ataxia-telangiectasia (A-T), designated ATM, and the use of the gene and gene products in detection of carriers of the A-T gene, and preparing native and transgenic organisms in which the gene products encoded by the ATM gene or its homolog in other species are artificially produced, or the expression of the native ATM gene is modified.

BACKGROUND OF THE INVENTION

Ataxia-telangiectasia (A-T) is a progressive genetic disorder affecting the central nervous and immune systems, and involving chromosomal instability, cancer predisposition, radiation sensitivity, and cell cycle abnormalities. Studies of the cellular phenotype of A-T have pointed to a defect in a putative system that processes a specific type of DNA damage and initiates a signal transduction pathway controlling cell cycle progression and repair. For a general review of Ataxia-telangiectasia, reference is hereby made to the review *Ataxia-Telangiectasis: Closer to Unraveling the Mystery*, Eur. J. Hum. Genet. (Shiloh, 1995) which, along with its cited references, is hereby incorporated by reference as well as to the reviews by Harnden (1994) and Taylor et al (1994).

Despite extensive investigation over the last two decades, A-T has remained a clinical and molecular enigma. A-T is a multi-system disease inherited in an autosomal recessive manner, with an average worldwide frequency of 1:40,000–1:100,000 live births and an estimated carrier frequency of 1% in the American population. Notable concentrations of A-T patients outside the United States are in Turkey, Italy and Israel. Israeli A-T patients are Moroccan Jews, Palestinian Arabs, Bedouins and Druzes.

Cerebellar ataxia that gradually develops into general motor dysfunction is the first clinical hallmark and results from progressive loss of Purkinje cells in the cerebellum. Oculocutaneous telangiectasia (dilation of blood vessels) develops in the bulbar conjunctiva and facial skin, and is later accompanied by graying of the hair and atrophic changes in the skin. The co-occurrence of cerebellar ataxia and telangiectases in the conjunctivae and occasionally on the facial skin—the second early hallmark of the disease—usually establishes the differential diagnosis of A-T from other cerebellar ataxias. Somatic growth is retarded in most patients, and ovarian dysgenesis is typical for female patients. Among occasional endocrine abnormalities, insulin-resistant diabetes is predominant, and serum levels of alpha-fetoprotein and carcinoembryonic antigen are elevated. The thymus is either absent or vestigial, and other immunological defects include reduced levels of serum IgA, IgE or IgG2, peripheral lymphopenia, and reduced responses to viral antigens and allogeneic cells, that cause many patients to suffer from recurrent sinopulmonary infections.

Cancer predisposition in A-T is striking: 38% of patients develop malignancies, mainly lymphoreticular neoplasms and leukemias. But, A-T patients manifest acute radiosensitivity and must be treated with reduced radiation doses, and not with radiomimetic chemotherapy. The most common cause of death in A-T, typically during the second or third decade of life, is sinopulmonary infections with or without malignancy.

The complexity of the disease is reflected also in the cellular phenotype. Chromosomal instability is expressed as increased chromosomal breakage and the appearance in lymphocytes of clonal translocations specifically involving the loci of the immune system genes. Such clones may later become predominant when a lymphoreticular malignancy appears. Primary fibroblast lines from A-T patients show accelerated senescence, increased demand for certain growth factors, and defective cytoskeletal structure. Most notable is the abnormal response of A-T cells to ionizing radiation and certain radiomimetic chemicals. While hypersensitive to the cytotoxic and clastogenic effects of these agents, DNA synthesis is inhibited by these agents to a lesser extent than in normal cells. The concomitant lack of radiation-induced cell cycle delay and reduction of radiation-induced elevation of p53 protein are evidence of defective checkpoints at the G1, S and G2 phases of the cell cycle. The G1 and G2 checkpoint defects are evident as reduced delay in cell cycle progression following treatment with ionizing radiation or radiomimetic chemicals, while the rise in the p53 protein level usually associated in normal cells with radiation-induced G1 arrest is delayed in A-T cells. The defective checkpoint at the S phase is readily observed as radioresistant DNA synthesis (RDS). Increased intrachromosomal recombination in A-T cells was also noted recently. Cellular sensitivity to DNA damaging agents and RDS are usually considered an integral part of the A-T phenotype.

Although these clinical and cellular features are considered common to all "classical" A-T patients, variations have been noted. Milder forms of the disease with later onset, slower clinical progression, reduced radiosensitivity and occasional absence of RDS have been described in several ethnic groups (Fiorilli, 1985; Taylor et al., 1987; Ziv et al., 1989; Chessa et al., 1992). Additional phenotypic variability possibly related to A-T is suggested by several disorders that show "partial A-T phenotype" with varying combinations of ataxia, immunodeficiency and chromosomal instability without telangiectases (12-16) (Ying & Decoteau, 1983; Byrne et al., 1984; Aicardi et al., 1988; Maserati et a;., 1988; Friedman & Weitberg, 1993). Still, other disorders display the A-T phenotype and additional features; most notable is the Nijmegen breakage syndrome that combines A-T features with microcephaly, sometimes with mental retardation, but without telangiectases (Weemaes et al., 1994).

Prenatal diagnoses of A-T using cytogenetic analysis or measurements of DNA synthesis have been reported, but these tests are laborious and subject to background fluctuations and, therefore, not widely used.

A-T homozygotes have two defective copies of the A-T gene and are affected with the disease. A-T heterozygotes (carriers) have one normal copy of the gene and one defective copy of the gene and are generally healthy. When two carriers have children, there is a 25% risk in every pregnancy of giving birth to an A-T affected child.

A-T heterozygotes show a significant excess of various malignancies, with a 3- to 4-fold increased risk for all cancers between the ages of 20 and 80, and a 5-fold increased risk of breast cancer in women. These observations turn A-T into a public health problem and add an important dimension to A-T research, particularly to heterozygote identification. Cultured cells from A-T heterozygotes indeed show an intermediate degree of X-ray sensitivity, but the difference from normal cells is not always large enough to warrant using this criterion as a laboratory assay for carrier detection. The main reason for the unreliability of this assay is the various degrees of overlap between A-T heterozygotes and non-heterozygotes with respect to radiosensitivity. Cytogenetic assays for carriers have the same problems as for prenatal diagnosis, they are labor intensive and not always consistent.

The nature of the protein missing in A-T is unknown. Cell fusion studies have established four complementation groups in A-T, designated A, C, D and E, suggesting the probable involvement of at least four genes or four types of mutations in one gene, with inter-allelic complementation. These four groups are clinically indistinguishable and were found to account for 55%, 28%, 14% and 3% of some 80 patients typed to date. In Israel, several Moroccan Jewish patients were assigned to group C, while Palestinian Arab patients were assigned to group A.

The general chromosomal localization of the putative A-T gene(s) has been determined, but not the sequence. An A-T locus containing the A-T(A) mutations was localized by Gatti et al. (1988) to chromosome 11, region q22-23, using linkage analysis. The A-T(C) locus was localized by applicant to the same region of chromosome 11, region q22-23, by linkage analysis of an extended Jewish Moroccan A-T family (Ziv et al., 1991). Further studies, conducted by an international consortium in which applicant participated (McConville et al., 1990; Foroud et al., 1991; Ziv et al., 1992), reconfirmed this localization in a series of studies and gradually narrowed the A-T locus to an interval estimated at 4 centimorgan, which probably contains also the A-T(E) mutations.

A proposed gene for complementation group D is disclosed in U.S. Pat. No. 5,395,767 to Murnane et al., issued Mar. 7, 1995. This sequence was found not to be mutated in any complementation group of A-T. Further, the gene sequence was mapped physically distant from the presumptive A-T locus.

Therefore, in order to better understand the nature and effects of A-T, as well as to more accurately and consistently determine those individuals who may carry the defective gene for A-T, it would be advantageous to isolate and determine the gene sequence, mutations of which are responsible for causing A-T, and utilize this sequence as a basis for detecting carriers of A-T and thereby be able to more beneficially manage the underlying conditions and predispositions of those carriers of the defective gene.

SUMMARY OF THE INVENTION AND ADVANTAGES

According to the present invention, a gene designated ATM and mutations of this gene which cause ataxia-telangiectasia (A-T), has been purified, isolated and determined as well as mutations of the gene.

The present invention further includes the method for identifying carriers of the defective A-T gene in a population and defective A-T gene products.

Further, the present invention provides transgenic and knockout nonhuman animal and cellular models.

The role of the ATM gene in cancer predisposition makes this gene an important target for screening. The detection of A-T mutation carriers is particularly significant in light of their radiation-sensitivity so that carrier exposure to radiation can be properly monitored and avoided.

BRIEF DESCRIPTION OF THE DRAWINGS

Other advantages of the present invention will be readily appreciated as the same becomes better understood by reference to the following detailed description when considered in connection with the accompanying drawings wherein:

FIGS. 1A–E illustrate the positional cloning steps to identify the A-T gene(s) wherein FIG. 1A is a high-density marker map of the A-T region on chromosome 11q22-23 (Vanagaite et al., 1995), constructed by generating microsatellite markers within genomic contigs spanning the region and by physical mapping of available markers using the same contigs, the prefix "D11" has been omitted from the marker designations, FDX: the adrenal ferredoxin gene, ACAT: the acetoacetyl-coenzyme A thiolase gene, the stippled box denotes the A-T interval, defined recently by individual recombinants between the markers S1818 and S1819 in a consortium linkage study (Lange et al., 1995), the solid box indicates the two-lod confidence interval for A-T obtained in that study, between S1294 and S384;

FIG. 1B illustrates a part of a YAC contig constructed across this region (Rotman et al., 1994c);

FIG. 1C illustrates part of a cosmid contig spanning the S384–S1818 interval, generated by screening a chromosome 11 specific cosmid library with YAC clones Y16 and Y67, and subsequent contig assembly of the cosmid clones by physical mapping (Shiloh, 1995);

FIG. 1D illustrates products of gene hunting experiments wherein solid boxes denote cDNA fragments obtained by using cosmid and YAC clones for hybrid selection of cDNAs (Lovett et al. 1991; Tagle et al., 1993) from a variety of tissues, open boxes denote putative exons isolated from these cosmids by exon trapping (Church et al., 1993), these sequences hybridized back to specific cosmids (broken lines), which allowed their physical localization to specific subregions of the contig (dotted frames); and FIG. 1E illustrates a 5.9 kb cDNA clone, designated 7-9 (SEQ ID No:1), identified in a fibroblast cDNA library using the cDNA fragments and exons in ID as a probe wherein the open box denotes an open reading frame of 5124 nucleotides, solid lines denote untranslated regions, striped arrowheads denote two Alu elements at the 3' end, and wherein dotted lines drawn between cDNA fragments and exons the cDNA indicate colinearity of sequences;

FIG. 4 is a diagram of the comparison of amino acid sequences of the human ATM and mouse Atm proteins wherein the alignment of amino acid sequences spanning the carboxy terminal portions that contain the PI 3-kinase domains of the two proteins are depicted with identical amino acids aligned by vertical bars, and similar amino acids by one or two dots.

DETAILED DESCRIPTION OF THE PREFERRED EMBODIMENT

Figure 1:
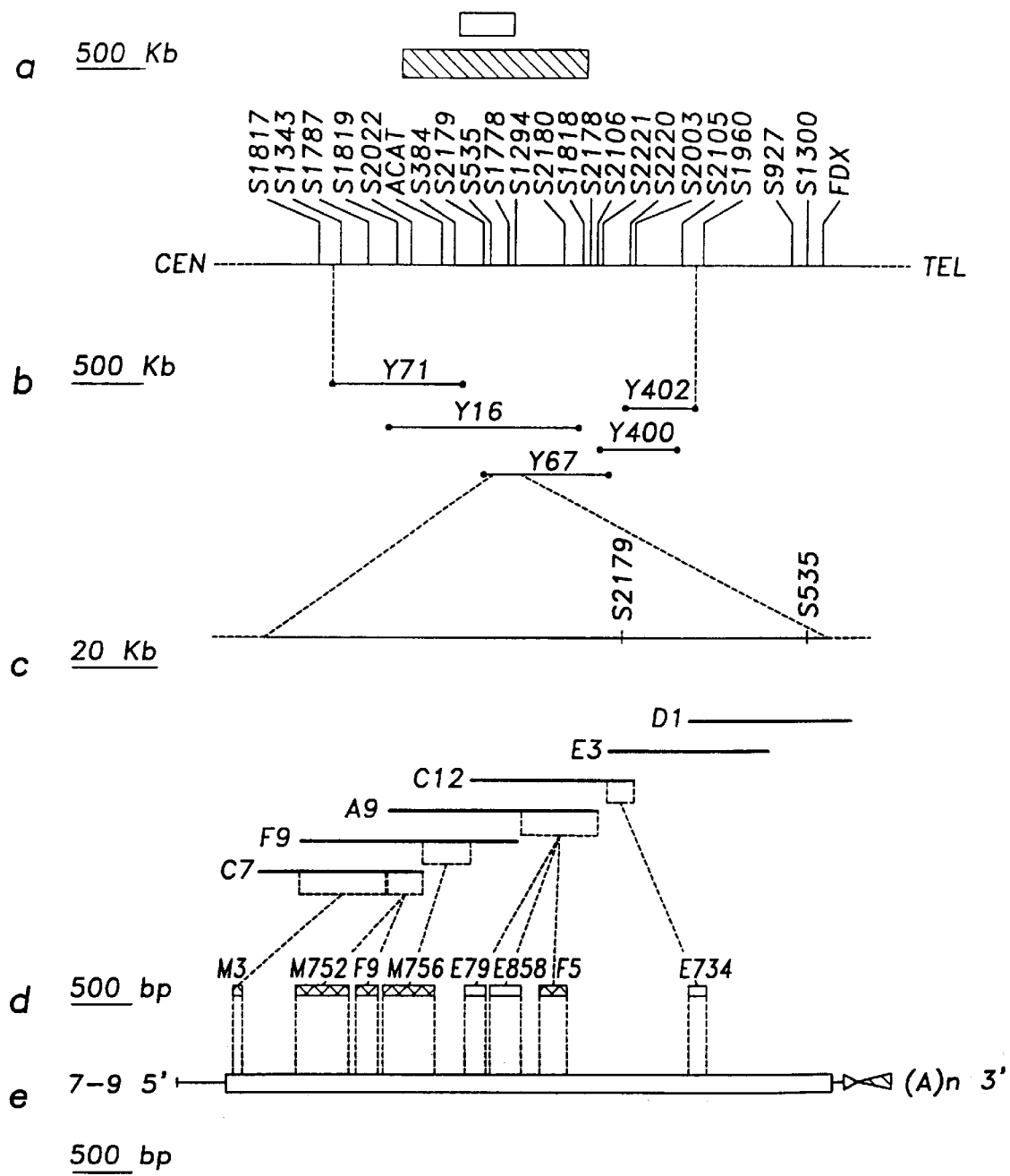

The present invention consists of a purified, isolated and cloned nucleic acid sequence encoding a gene, designated ATM, mutations in which cause ataxia-telangiectasia and genetic polymorphisms thereof. The nucleic acid can be genomic DNA, cDNA or mRNA.

The complete coding sequence of the ATM gene is set forth in SEQ ID No:2 and was submitted to the GenBank database under accession number U33841. There is extensive alternate splicing at the 5' untranslated region (5'UTR) of the ATM transcript giving rise to twelve different 5' UTRs. The sequence of the longest 5'UTR is set forth in SEQ ID No:9. The first exon in this sequence is designated 1b. There is an alternative leader exon, designated 1a (SEQ ID No:10). The sequence of the complete 3'UTR is set forth in SEQ ID No:8. Together these sequences contain the complete sequence of the ATM transcript.

Polymorphisms are variants in the sequence generally found between different ethnic and geographic locations which, while having a different sequence, produce functionally equivalent gene products.

Current mutation data (as shown in Tables 1 and 2) indicate that A-T is a disease characterized by considerable allelic heterogeneity. Mutations imparting defects into the A-T gene can be point mutations, deletions, insertions or rearrangements. The mutations can be present within the nucleotide sequence of either/or both alleles of the ATM gene such that the resulting amino acid sequence of the ATM protein product is altered in one or both copies of the gene product; when present in both copies imparting ataxia-telangiectasia. Alternatively, a mutation event selected from the group consisting of point mutations, deletions, insertions and rearrangements could have occurred within the flanking sequences and/or regulatory sequences of ATM such that regulation of ATM is altered imparting ataxia-telangiectasia.

Table 1 illustrates several mutations in the ATM gene found in A-T patients. Mutations in the ATM gene were found in all of the complementation groups suggesting that ATM is the sole gene responsible for all A-T cases.

Table 2 illustrates the 44 mutations identified to date in applicant's patient cohort and include 34 new ones and 10 previously listed in Table 1. These mutations were found amongst 55 A-T families: many are unique to a single family, while others are shared by several families, most notably the 4 nt deletion, 7517del4, which is common to 6 A-T families from South-Central Italy. The nature and location of A-T mutations, as set forth in Table 2, provide insight into the function of the ATM protein and the molecular basis of this pleiotropic disease.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. Of the 44 A-T mutations identified, 39 (89%) are expected to inactivate the ATM protein by truncating it, by abolishing correct initiation or termination of translation, or by deleting large segments. Additional mutations are four smaller in-frame deletions and insertions, and one substitution of a highly conserved amino acid at the PI 3-kinase domain. The emerging profile of mutations causing A-T is thus dominated by those expected to completely inactivate the ATM protein. ATM mutations with milder effects appear to result in phenotypes related, but not identical, to A-T. In view of the pleiotropic nature of the ATM gene, the range of phenotypes associated with various ATM genotypes may be even broader, and include mild progressive conditions not always defined as clear clinical entities as discussed herein below in Example 3. Screening for mutations in this gene in such cases will reveal wider boundaries for the molecular pathology associated with the ATM gene. The present invention therefore allows the identification of these mutations in subjects with related phenotypes to A-T.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

In cloning the gene for A-T (Example 2), the strategy used was a standard strategy in identifying a disease gene with an unknown protein product known as positional cloning, as is well known in the art. In positional cloning, the target gene is localized to a specific chromosomal region by establishing linkage between the disease and random genetic markers defined by DNA polymorphisms. Definition of the smallest search interval for the gene by genetic analysis is followed by long-range genomic cloning and identification of transcribed sequences within the interval. The disease gene is then identified among these sequences, mainly by searching for mutations in patients.

Several important and long sought disease genes were isolated recently in this way (Collins, 1992; Attree et al., 1992; Berger et al., 1992; Chelly et al., 1993; Vetrie et al., 1993; Trofatter et al., 1993; The Huntington's Disease Collaborative Research Group, 1993; The European Polycystic Kidney Disease Consortium, 1994; Miki et al., 1994).

Two complementary methods were used for the identification of transcribed sequences (gene hunting): hybrid selection based on direct hybridization of genomic DNA with cDNAs from various sources (Parimoo et al., 1991; Lovett et al., 1991); and exon trapping (also called exon amplification), which identifies putative exons in genomic DNA by virtue of their splicing capacity (Church et al., 1993). In hybrid selection experiments, cosmid and YAC clones served to capture cross-hybridizing sequences in cDNA collections from placenta, thymus and fetal brain, using the magnetic bead capture protocol (Morgan et al., 1992; Tagle et al., 1993). In parallel experiments, YAC clones were bound to a solid matrix and used to select cDNA fragments from a heterogeneous cDNA collection representing several human tissues (Parimoo et al., 1993). The cosmids were also used for exon trapping with the pSPL3 vector (Church et al., 1994). The captured cDNA fragments and trapped exons were mapped back to the A-T region by hybridization to several radiation hybrids containing various portions of the 11q22-23 region (Richard et al., 1993; James et al., 1994), and to high-density grids containing all the YACs and cosmids spanning this interval. An extensive transcriptional map of the A-T region was thus constructed (Shiloh et al., 1994).

Pools of adjacent cDNA fragments and exons, expected to converge into the same transcriptional units, were used to screen cDNA libraries. A cluster of 5 cDNA fragments and 3 exons mapped in close proximity to the marker D11S535, where the location score for A-T had peaked (Lange et al., 1995). All these sequences hybridized to the same 5.9 kb of the cDNA clone, 7-9, (SEQ ID No:1) obtained from a fibroblast cDNA library.

Hybridization of the 7-9 cDNA clone to the radiation hybrid panel indicated that the entire transcript was derived from the chromosome 11 locus. The full sequence of this clone (SEQ ID No:1) was obtained using a shotgun strategy, and found to contain 5921 bp which includes an open reading frame (ORF) of 5124 nucleotides, a 538 bp 3' untranslated region (3' UTR), and a 259 bp 5' non-coding sequence containing stop codons in all reading frames. (Genbank Accession No. U26455). Two Alu repetitive elements were observed at the 3' end of this clone and in nine smaller clones representing this gene from the same cDNA library. Since no polyadenylation signal was identified in these cDNA clones, their poly(A) tracts were assumed to be associated with the Alu element rather than being authentic poly(A) tails of these transcripts. This assumption was later supported when applicants identified a cDNA clone derived from the same gene in a leukocyte cDNA library, with an alternative 3' UTR containing a typical polyadenylation signal. Alignment of the cDNA with the genomic physical map showed that the corresponding gene is transcribed from centromere to telomere.

Hybridization of a probe containing the entire ORF of clone 7-9 to northern blots from various tissues and cell lines revealed a major transcript of 12 kb, later shown to be 13 kb, in all tissues and cell types examined, and minor species of various sizes in several tissues, possibly representing alternatively spliced transcripts of the corresponding gene or other homologous sequences. Genomic sequencing later identified the 5' non-coding region of clone 7-9 as sequences of the unspliced adjacent intron. Two other cDNA clones from a leukocyte cDNA library were found to contain this intronic sequence in their 5' ends. These clones may represent splicing intermediates.

Figure 2:
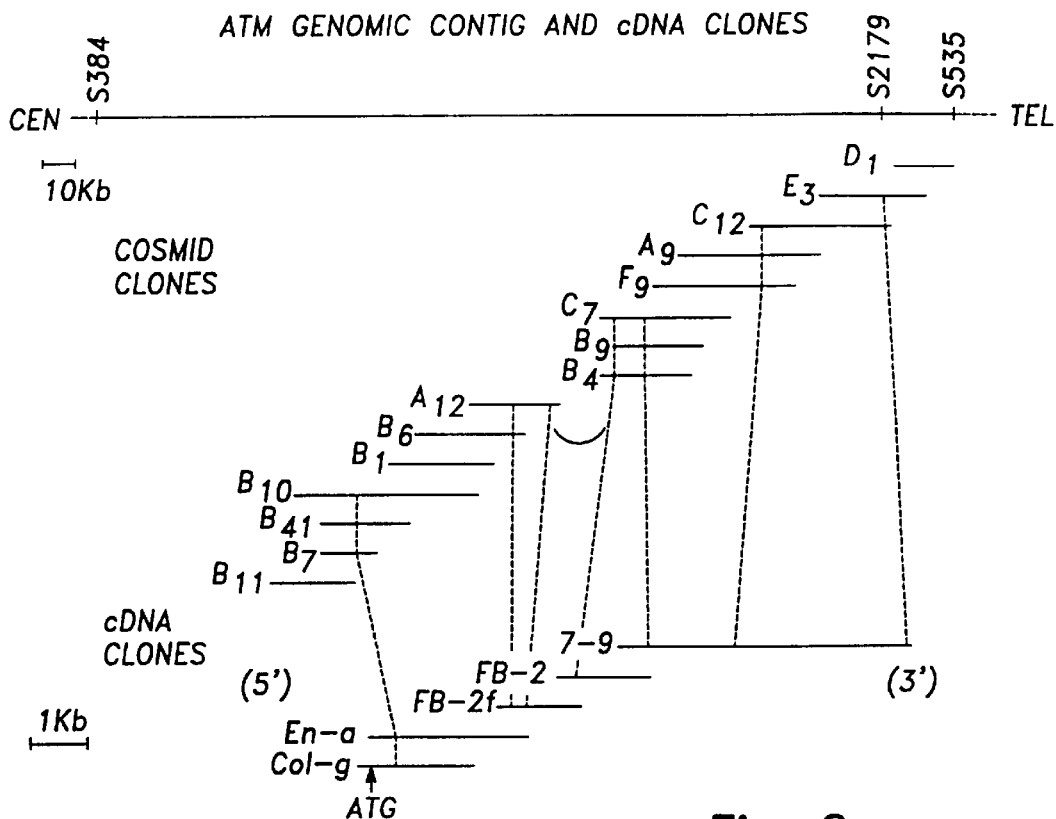
FIG. 2 is a diagram of the physical map of the ATM region and relationship to the cDNA wherein the top line represents a linear map of the region containing known genetic markers (the prefix D11 has been omitted from marker designations) and shown below the linear map is a portion of a cosmid contig spanning the region with the arch between ends of cosmids A12 and B4 represents a genomic PCR product, a contig of cDNA clones which span the ATM ORF is shown at the bottom of the figure, broken lines denote the position of specific cDNA sequences with the cosmid contig.

The 7-9 cDNA clone represents only part of the ATM gene transcript. Successive screening of randomly-primed cDNA libraries identified a series of partly overlapping cDNA clones and enabled the construction of a cDNA contig of about 10 Kb (FIG. 2). The gene coding for this transcript spans about 150 Kb of genomic DNA.

The composite cDNA of 9860 bp (GenBank Accession No. U33841; SEQ ID No:2) includes an open reading frame of 9168 nucleotides, a 538 bp 3' untranslated region (UTR), and a 164 bp 5' UTR containing stop codons in all reading frames. The sequence surrounding the first in-frame initiation codon (ACC<u>ATG</u>A) resembles the consensus sequence proposed by Kozak for optimal initiation of translation, (A/G)CC<u>ATG</u>G (ref. 20 in Savitsky et al, 1995b). No polyadenylation signal was found at the 3' UTR. The same poly(A) tail was found in all cDNA clones and 3' RACE products isolated to date in applicant's laboratory, however, this poly(A) tail most likely belongs to the Alu element contained in the 3' UTR.

Sequencing and PCR analysis of 32 partial ATM cDNA clones, obtained from 11 cDNA libraries representing 8 different tissues, did not show coding sequences in addition to those presented herein.

The invention further provides a purified protein as encoded by the ATM gene (SEQ ID No:2) and analogs thereof. A consensus complete sequence is set forth in SEQ ID No:3. The present invention further provides for mutations in SEQ ID No:2 and SEQ ID No:3 which cause ataxia-telangiectasia, for example, as set forth in Tables 1 and 2.

This product (SEQ ID No:3) of the ATM Open Reading Frame (SEQ ID No:2) is a large protein of 3056 amino acids, with an expected molecular weight of 350.6 kDa. The ATM gene product (SEQ ID No:3) contains a PI-3 kinase signature at codons 2855–2875, and a potential leucine zipper at codons 1217–1238. The presence of this leucine zipper may suggest possible dimerization of the ATM protein or interaction with additional proteins. No nuclear localization signal, transmembrane domains or other motifs were observed in this protein sequence.

The ATM gene product is a member of a family of large proteins that share a highly conserved carboxy-terminal region of about 300 amino acids showing high sequence homology to the catalytic domain of PI-3 kinases. Among these proteins are Tel1p and Mec1p in budding yeast, rad3p in fission yeast, the TOR proteins in yeast and their mammalian counterpart, FRAP (RAFT1), MEI-41 in *Drosophila melanogaster*, and the catalytic subunit of DNA-dependent protein kinase (DNA-PKcs) in mammals. All of these proteins are implicated in cell cycle control and some of them, like Mec1p, rad3p and DNA-PKcs are involved in response to DNA damage (Table 3). The central core of the PI-3 kinase-like domain contains two subdomains with highly conserved residues present in nearly all kinases, including protein and PI-3 kinases. The residues Asp and Asn (at positions 2870 and 2875 in ATM), and the triplet Asp-Phe-Gly (at positions 2889–2891), which represents the most highly conserved short stretch in the protein kinase catalytic domain, have been implicated in the binding of ATP and phosphotransferase activity. Mutations in the genes encoding these proteins result in a variety of phenotypes that share features with A-T, such as radiosensitivity, chromosomal instability, telomere shortening, and defective cell cycle checkpoints (reviewed by Savitsky et al., 1995a and b; Zakian, 1995).

A possible working model for the ATM protein's function is DNA-PK, a serine/threonine protein kinase that is activated in vitro by DNA double-strand breaks and responds by phosphorylating several regulatory proteins (Gottlieb and Jackson, 1994). The ATM protein may be responsible for conveying a signal evoked by a specific DNA damage to various checkpoint systems, possibly via lipid or protein phosphorylation.

The present invention further includes a recombinant protein encoded by SEQ ID No:3. This recombinant protein is isolated and purified by techniques known to those skilled in the art.

An analog will be generally at least 70% homologous over any portion that is functionally relevant. In more preferred embodiments, the homology will be at least 80% and can approach 95% homology to the ATM protein. The amino acid sequence of an analog may differ from that of the ATM protein when at least one residue is deleted, inserted or substituted but the protein remains functional and does not cause A-T. Differences in glycosylation can provide analogs.

The present invention provides an antibody, either polyclonal or monoclonal, which specifically binds to a polypeptide/protein encoded by the ATM gene and/or mutant epitopes on the protein. Examples of such antibodies are set forth in Example 5. In preparing the antibody, the protein (with and without mutations) encoded by the ATM gene and polymorphisms thereof is used as a source of the immunogen. Peptide amino acid sequences isolated from the amino acid sequence as set forth in SEQ ID No:3 or mutant peptide sequences can also be used as an immunogen.

The antibodies may be either monoclonal or polyclonal. Conveniently, the antibodies may be prepared against a synthetic peptide based on the sequence, or prepared recombinantly by cloning techniques or the natural gene product and/or portions thereof may be isolated and used as the immunogen. Such proteins or peptides can be used to produce antibodies by standard antibody production technology well known to those skilled in the art as described generally in Harlow and Lane, *Antibodies: A Laboratory Manual,* Cold Spring Harbor Laboratory Press, Cold Spring Harbor, N.Y., 1988.

For producing polyclonal antibodies a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

The antibody can be bound to a solid support substrate or conjugated with a detectable moiety or be both bound and conjugated as is well known in the art. (For a general discussion of conjugation of fluorescent or enzymatic moieties see Johnstone and Thorpe, *Immunochemistry in Practice,* Blackwell Scientific Publications, Oxford, 1982.) The binding of antibodies to a solid support substrate is also well known in the art. (see for a general discussion Harlow and Lane *Antibodies: A Laboratory Manual,* Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

The present invention provides vectors comprising an expression control sequence operatively linked to the nucleic acid sequence of the ATM gene, SEQ ID No:2 and portions thereof as well as mutant sequences which lead to the expression of A-T. The present invention further provides host cells, selected from suitable eucaryotic and procaryotic cells, which are transformed with these vectors.

Using the present invention, it is possible to transform host cells, including *E. coli*, using the appropriate vectors so that they carry recombinant DNA sequences derived from the ATM transcript or containing the entire ATM transcript in its normal form or a mutated sequence containing point mutations, deletions, insertions, or rearrangements of DNA which lead to the expression of A-T. Such transformed cells allow the study of the function and the regulation of the A-T gene. Use of recombinantly transformed host cells allows for the study of the mechanisms of A-T and, in particular it will allow for the study of gene function interrupted by the mutations in the A-T gene region.

Vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1992), in Ausubel et al., *Current Protocols in Molecular Biology,* John Wiley and Sons, Baltimore, Md. (1989), Chang et al., *Somatic Gene Therapy,* CRC Press, Ann Arbor, Mich. (1995), Vega et al., *Gene Targeting,* CRC Press, Ann Arbor, Mich. (1995) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. See also U.S. Pat. Nos. 5,487,992 and 5,464,764. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the sense, antisense or triplex inhibition of a target nucleic acid. For example, vectors containing antisense nucleic acids can be employed to express protein or antisense message to reduce the expression of the target nucleic acid and therefore its activity.

A specific example of DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted. For example, if breast cancer is to be treated, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention includes the construction of transgenic and knockout organisms that exhibit the phenotypic manifestations of A-T. The present invention provides for transgenic ATM gene and mutant ATM gene animal and cellular (cell lines) models as well as for knockout ATM models. The transgenic models include those carrying the sequence set forth SEQ ID Nos:2,8,9 (or 10). These models are constructed using standard methods known in the art and as set forth in U.S. Pat. Nos. 5,487,992, 5,464,764, 5,387, 742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information. See also in general Hogan et al "Manipulating the Mouse Embryo" Cold Spring Harbor Laboratory Press, 2nd Edition (1994).

Further, the mouse homolog of the A-T gene, designated Atm, has been identified as set forth in detail in Example 4, hereinbelow. The coding sequence of Atm (SEQ ID No:11), the mouse homolog of the human gene ATM defective in A-T, was cloned and found to contain an open reading frame encoding a protein of 3,066 amino acids (SEQ ID No:12) with 84% overall identity and 91% similarity to the human ATM protein (SEQ ID No:3). Variable levels of expression of Atm were observed in different tissues. Fluorescence in situ hybridization and linkage analysis located the Atm gene on mouse chromosome 9, band 9C, in a region homologous to the ATM region on human chromosome 11q22-23. The present invention includes the -construction of mice in which the mouse homolog of the A-T gene has been knocked out.

According to the present invention, there is provided a method for diagnosing and detecting carriers of the defective gene responsible for causing A-T. The present invention further provides methods for detecting normal copies of the ATM gene and its gene product. Carrier detection is especially important since A-T mutations underlie certain cases of cancer predisposition in the general population. Identifying the carriers either by their defective gene or by their missing or defective protein(s) encoded thereby, leads to earlier and more consistent diagnosis of A-T gene carriers. Thus, since carriers of the disease are more likely to be cancer-prone and/or sensitive to therapeutic applications of radiation, better surveillance and treatment protocols can be initiated for them. Conversely, exclusion of A-T heterozygotes from patients undergoing radiotherapy can allow for establishing routinely higher dose schedules for other cancer patients thereby improving the efficacy of their treatment.

Briefly, the methods comprise the steps of obtaining a sample from a test subject, isolating the appropriate test material from the sample and assaying for the target nucleic acid sequence or gene product. The sample can be tissue or bodily fluids from which genetic material and/or proteins are isolated using methods standard in the art. For example, DNA can be isolated from lymphocytes, cells in amniotic fluid and chorionic villi (Llerena et al., 1989).

More specifically, the method of carrier detection is carried out by first obtaining a sample of either cells or bodily fluid from a subject. Convenient methods for obtaining a cellular sample can include collection of either mouth wash fluids or hair roots. A cell sample could be amniotic or placental cells or tissue in the case of a prenatal diagnosis. A crude DNA could be made from the cells (or alternatively proteins isolated) by techniques well known in the art. This isolated target DNA is then used for PCR analysis (or alternatively, Western blot analysis for proteins from a cell line established from the subject) with appropriate primers derived from the gene sequence by techniques well known in the art. The PCR product would then be tested for the presence of appropriate sequence variations in order to assess genotypic A-T status of the subject.

The specimen can be assayed for polypeptides/proteins by immunohistochemical and immunocytochemical staining (see generally Stites and Terr, *Basic and Clinical Immunology*, Appleton and Lange, 1994), ELISA, RIA, immunoblots, Western blotting, immunoprecipitation, functional assays and protein truncation test. In preferred embodiments, Western blotting, functional assays and protein truncation test (Hogervorst et al., 1995) will be used. mRNA complementary to the target nucleic acid sequence can be assayed by in situ hybridization, Northern blotting and reverse transcriptase-polymerase chain reaction. Nucleic acid sequences can be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994)

ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Current mutation data (as shown in Tables 1 and 2) indicate that A-T is a disease characterized by considerable allelic heterogenicity. It is not surprising that there are hundreds (or even thousands) of ATM mutations (as is the case for cystic fibrosis and BRCAI) as shown in Table 2. Thus, it will be important for a successful mutation screen to be able to detect all possible nucleotide alterations in the ATM gene, rather than being focused on a limited subset. Methods including direct sequencing of PCR amplified DNA or RNA or DNA chip hybridization (Fodor et al., 1993; Pease et al., 1994) can be applied along with other suitable methods known to those skilled in the art.

In order to use the method of the present invention for diagnostic applications, it is advantageous to include a mechanism for identifying the presence or absence of target polynucleotide sequence (or alternatively proteins). In many hybridization based diagnostic or experimental procedures, a label or tag is used to detect or visualize for the presence or absence of a particular polynucleotide sequence. Typically, oligomer probes are labelled with radioisotopes such as $^{32}P$ or $^{35}S$ (Sambrook, 1992) which can be detected by methods well known in the art such as autoradiography. Oligomer probes can also be labelled by non-radioactive methods such as chemiluminescent materials which can be detected by autoradiography (Sambrook, 1992). Also, enzyme-substrate based labelling and detection methods can be used. Labelling can be accomplished by mechanisms well known in the art such as end labelling (Sambrook, 1992), chemical labelling, or by hybridization with another labelled oligonucleotide. These methods of labelling and detection are provided merely as examples and are not meant to provide a complete and exhaustive list of all the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers is applied.

Functional assays can be used for detection of A-T carriers or affected individuals. For example, if the ATM protein product is shown to have PI 3-kinase biochemical activity which can be assayed in an accessible biological material, such as serum, peripheral leukocytes, etc., then homozygous normal individuals would have approximately normal biological activity and serve as the positive control. A-T carriers would have substantially less than normal biological activity, and affected (i.e. homozygous) individuals would have even less biological activity and serve as a negative control. Such a biochemical assay currently serves as the basis for Tay-Sachs carrier detection.

The present invention also provides a kit for diagnosis and detection of the defective A-T gene in populations. The kit includes a molecular probe complementary to genetic sequences of the defective gene which causes ataxia-telangiectasia (A-T) and suitable labels for detecting hybridization of the molecular probe and the defective gene thereby indicating the presence of the defective gene. The molecular probe has a DNA sequence complementary to mutant sequences in the population. Alternatively, the kit can contain reagents and antibodies for detection of mutant proteins.

The above discussion provides a factual basis for the use and identification of the ataxia-telangiectasia gene and gene products and identification of carriers as well as construction of transgenic organisms. The methods used in the present invention can be shown by the following non-limiting example and accompanying figures.

EXAMPLES

Materials and Methods

General methods in molecular biology:

Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989) and methodology as set forth in U.S. Pat. Nos. 4,666,828; 4,683,202; 4,801,531; 5,192,659 and 5,272,057. Polymerase chain reaction (PCR) was carried out generally as in *PCR Protocols: A Guide To Methods And Applications*, Academic Press, San Diego, Calif. (1990). Protein analysis techniques were as described in Coligan et al., *Current Protocols in Immunology*, John Wiley and Sons, Baltimore, Md. (1992, 1994).

Patient and family resources:

A cell line repository was established containing 230 patient cell lines and 143 cell lines from healthy members of Moroccan Jewish, Palestinian Arab and Druze families. Some of these pedigrees are highly inbred and unusually large (Ziv et al., 1991; Ziv, 1992). In view of the large number of meiotic events required for high-resolution linkage analysis, applicants collaborated with Dr. Carmel McConville (University of Birmingham, UK) and Dr. Richard Gatti (UCLA, Los Angeles, Calif.), who have also established extensive repositories of A-T families. Linkage analysis was conducted on a pool of 176 families.

EXAMPLE 1

Definition of the A-T Interval by Genetic Analysis

Studies based only on analysis of Israeli A-T families enabled localization of the A-T(C) gene at 11q22-23 (Ziv, 1991), and confirmed the localization of A-T(A) mutation in Palestinians to the same region (Ziv et al., 1992). Studies with the Birmingham group further narrowed the major A-T interval to 4 centimorgans, between D11S611 and D11S1897 (McConville et al., 1993), and subsequently to 3 centimorgans, between GRIA4 and D11S1897 (Ambrose et al., 1994; McConville et al., 1994; Shiloh, 1995, and FIG. 1).

All these studies were conducted with biallelic markers, whose power is limited by their low polymorphic information content (PIC). The recently discovered microsatellite markers based on variable numbers of tandem simple repeats (Litt and Luty, 1989; Weber and May, 1989) are much more powerful due to their high degree of polymorphism. Microsatellite markers were used to saturate the A-T region using two approaches. The first, was based on physical mapping of microsatellite markers generated by others which were loosely linked to chromosome 11q.

Mapping experiments were conducted using YAC and cosmid contigs which allowed precise, high-resolution localization of DNA sequences in this region of chromosome 11. Twelve microsatellites were localized at the A-T region (Vanagaite et al., 1994a; Vanagaite et al., 1995).

The second approach was based on generating new microsatellites within the YAC contig. A rapid method for the identification of polymorphic CA-repeats in YAC clones was set up (Rotman, 1995) resulting in the generation of twelve new markers within the A-T locus (Vanagaite et al., 1995; Rotman et al., 1995; Rotman et al., 1994b). Hence, the high-density microsatellite map constructed in this manner contained a total of 24 new microsatellite markers and spans the A-T locus and flanking sequences, over a total of six megabases (Vanagaite et al., 1995).

Repeated linkage analysis on the entire cohort of A-T families indicated that the A-T(A) locus was definitely located within a 1.5 megabase region between D11S1819 and D11S1818 (Gatti et al., 1994) as shown in FIG. 1 and in Shiloh (1995), with a clear peak of the cumulative lod score under D11S535 (Lange et al., 1994).

Concomitant with these studies, linkage disequilibrium (LD) analysis of Moroccan-Jewish A-T patients was conducted. LD refers to the non-random association between alleles at two or more polymorphic loci (Chakravarti et al., 1984). LD between disease loci and linked markers is a useful tool for the fine localization of disease genes (Chakravarti et al., 1984; Kerem et al. 1989; Ozelius et al., 1992; Sirugo et al., 1992; Hastbacka et al., 1992; Mitchison et al., 1993). LD is particularly powerful in isolated ethnic groups, where the number of different mutations at a disease locus is likely to be low (Hastbacka et al., 1992; Lehesjoki et al., 1993; Aksentijevitch et al., 1993). Early on, applicants observed very significant LD (p<0.02–p<0.001) between A-T and markers along the D11S1817–D11S927 region in the patients of the sixteen Moroccan-Jewish A-T families identified in Israel (Oskato et al., 1993). Further analysis with the new markers narrowed the peak of linkage disequilibrium to the D11S384–D11S1818 region as shown in FIG. 1.

Haplotype analysis indicated that all of the mutant chromosomes carry the same D11S384–D11S1818 haplotype, suggesting a founder effect for A-T in this community, with one mutation predominating.

EXAMPLE 2

SEQUENCING THE ATM GENE

Cloning the disease locus in a contig (set of overlapping clones) was essential in isolating the. A-T disease gene. The entire A-T locus and flanking region in a contig of yeast artificial chromosomes (YACs) was cloned by methods well known in the art (Rotman et al. 1994c; Rotman et al., 1994d). This contig was instrumental in the construction of the microsatellite map of the region (Vanagaite et al., 1995) and subsequently enabled construction of cosmid contigs extending over most of the interval D11S384–D11S1818. Cosmids corresponding to the YAC clones were identified in a chromosome 11-specific cosmid library supplied by Dr. L. Deaven (Los Alamos National Laboratory) and were ordered into contigs by identifying overlaps as shown in FIG. 1.

Isolation of the A-T gene:

Transcribed sequences were systematically identified based on two complementary methods:

1. Use of an improved direct selection method based on magnetic bead capture (MBC) of cDNAs corresponding to genomic clones (Morgan et al., 1992; Tagle et al., 1993). In several, large-scale experiments YAC or cosmid DNA was biotinylated and hybridized to PCR-amplified cDNA from thymus, brain and placenta. Genomic DNA-cDNA complexes were captured using streptavidin-coated magnetic beads which was followed with subsequent elution, amplification, and cloning of captured cDNAs. The cDNA inserts were excised from a gel, self-ligated to form concatamers and sonicated to obtain random fragments. These fragments were size fractionated by gel electrophoresis, and the 1.0–1.5 Kb fraction was extracted from the gel and subcloned in a plasmid vector. The end portions of individual clones were sequenced using vector-specific primers, in an automated sequencer (Model 373A, Applied Biosystems), and the sequences were aligned using the AutoAssembler program (Applied Biosystems Division, Perkin-Elmer Corporation). In the final sequence each nucleotide position represents at least 3 independent overlapping readings.

YACs were also used and were no less efficient than cosmids as starting material for MBC, with more than 50% of the products mapping back to the genomic clones. However, when a small panel of radiation hybrids spanning the A-T region was used to test the cDNA fragments, it was found that some clones that hybridized back to the YACs and cosmids were not derived from this region. This pitfall probably stems from limited homology between certain portions of different genes, and points up the necessity to use radiation hybrid mapping when testing the authenticity of the captured sequences, and not to rely solely on cloned DNA for this purpose.

Homology searches in sequence databases showed that only one of the first 105 cDNA fragments mapped to the A-T region was homologous to a sequence previously deposited in one of the databases, as an expressed sequence tag (EST).

2. Exon amplification, also termed "exon trapping" (Duyk et al., 1990; Buckler et al., 1991), is based on cloning genomic fragments into a vector in which exon splice sites are flagged by splicing to their counterpart sites in the vector. This method of gene identification was expected to complement the MBC strategy, since it does not depend on the constitution of cDNA libraries or on the relative abundance of transcripts, and is not affected by the presence of repetitive sequences in the genomic clones. An improved version of this system (Church et al., 1993) that eliminated problems identified in an earlier version, including a high percentage of false positives and the effect of cryptic splice sites was utilized. Each experiment ran a pool of three to five cosmids with an average of two to five exons identified per cosmid. A total of forty five exons were identified.

Sequence analysis and physical mapping indicated that MBC and exon amplification were complementary in identifying transcribed sequences.

The availability of a deep cosmid contig enabled rapid and precise physical localization of the cDNA fragments and captured exons, leading to a detailed transcriptional map of the A-T region.

Both MBC and exon amplification yielded short (100–1000 bp) transcribed sequences. Those sequences were used as anchor points in isolating full-length clones from twenty eight cDNA libraries currently at applicants disposal and which represented a variety of tissues and cell lines.

Initial screening of the cDNA libraries by polymerase chain reaction (PCR) using primer sets derived from individual cDNA fragments or exons aided in the identification of the libraries most likely to yield corresponding cDNA clones.

Large scale screening experiments were carried out in which most of the cDNA fragments and exons were used in large pools. In addition to the mass screening by hybridization, PCR-based screening methods and RACE (rapid amplification of cDNA ends) (Frohman et al., 1988; Frohman et al., 1994) was employed to identify full-length cDNAs.

The above experiments resulted in the initial identification and isolation of a cDNA clone designated 7-9 (Savitsky et al, 1995a), the complete sequence of which is set forth in SEQ ID No:1 and which is derived from a gene located under the peak of cumulative location score obtained by linkage analysis as shown in FIG. 1. The gene extends over some 300 kilobases (kb) of genomic DNA and codes for two major mRNA species of 12 kb and 10.5 kb in length. The 7-9 clone is 5.9 kb in length and, therefore, is not a full length clone.

An open reading frame of 5124 bp within this cDNA encodes a protein with signature motifs typical of a group of signal transduction proteins known as phosphatidylinositol 3-kinases (PI 3-kinases). PI 3-kinases take part in the complex system responsible for transmitting signals from the outer environment of a cell into the cell. It is not clear yet whether the protein product of the corresponding gene encodes a lipid kinase or a protein kinase.

The gene encoding the 7-9 cDNA clone was considered a strong A-T candidate and mutations were sought in patients. Southern blotting analysis revealed a homozygous deletion in this gene in affected members of Family N., an extended Palestinian Arab A-T family which has not been assigned to a specific complementation group. All the patients in this family are expected to be homozygous by descent for a single A-T mutation. The deletion includes almost the entire genomic region spanned by transcript 7-9, and was found to segregate in the family together with the disease. This finding led to a systematic search for mutations in the 7-9 transcript in additional patients, especially those previously assigned to specific complementation groups.

The restriction endonuclease fingerprinting (REF) method (Liu and Sommer 1995) was applied to reverse-transcribed and PCR-amplified RNA (RT-PCR) from A-T cell lines. Observation of abnormal REF patterns was followed by direct sequencing of the relevant portion of the transcript and repeated analysis of another independent RT product. In compound heterozygotes, the two alleles were separated by subcloning of RT-PCR products and individually sequenced. Genomic sequencing was conducted in some cases to confirm the sequence alteration at the genomic level. Additional family members were studied when available.

Ten sequence alterations (Table 1) were identified in the 7-9 transcript in 13 A-T patients including two sibling pairs. Most of these sequence changes are expected to lead to premature truncation of the protein product, while the rest are expected to create in-frame deletions of 1-3 amino acid residues in this protein. While the consequences of the in-frame deletions remain to be investigated, it is reasonable to assume that they result in impairment of protein function. In one patient, AT3NG, the loss of a serine residue at position 1512 occurs within the PI3-kinase signature sequence. This well conserved domain is distantly related to the catalytic site of protein kinases, hence this mutation is likely to functionally affect the 7-9 protein.

In view of the strong evidence that mutations in this gene are responsible for A-T, it was designated ATM (A-T, Mutated). Since these patients represent all complementation groups of the disease and considerable ethnic variability, these results indicate that the ATM gene alone is responsible for all A-T cases.

In order to complete the cloning of the entire ATM open reading frame, fetal brain and colon random-primed libraries obtained from Stratagene (San Diego, Calif.) and an endothelial cell random-primed library (a gift of Dr. David Ginsburg, University of Michigan) were screened. A total of $1\times10^6$ pfu were screened at a density of 40,000 pfu per 140 mm plate, and replicas were made on Qiabrane filters (Qiagen), as recommended by the manufacturer. Filters were prehybridized in a solution containing 6×SSC, 5×Denhardt's, 1% N-laurylsarcosyl, 10% dextran sulfate and 100 µg/ml salmon sperm DNA for 2 hours at 65° C. Hybridization was performed for 16 hrs under the same conditions with $1\times10^6$ cpm/ml of $^{32}$P-labelled probe, followed by final washes of 30 minutes in 0.25×SSC, 0.1%SDS at 60° C. Positive clones were plaque-purified using standard techniques and sequenced. DNA sequencing was performed using an automated DNA sequencer (Applied Biosystems, model 373A), and the sequence was assembled using the AutoAssembler program (Applied Biosystems Division, Perkin-Elmer Corporation). In the final sequence, each nucleotide represents at least four independent readings in both directions.

Database searches for sequence similarities were performed using the BLAST network service. Alignment of protein sequences and pairwise comparisons were done using the MACAW program, and the PILEUP and BESTFIT programs in the sequence analysis software package developed by the Genetics Computer Group at the University of Wisconsin.

EXAMPLE 3

DETECTION OF MUTATIONS

Determination of mutations:

The recently discovered ATM gene is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

MATERIALS AND METHODS

RT-PCR:

Total RNA was extracted from cultured fibroblast or lymphoblast cells using the Tri-Reagent system (Molecular research Center, Cincinnati, Ohio). Reverse transcription was performed on 2.5 ug of total RNA in a final volume of 10 ul, using the Superscript II Reverse Transcriptase (Gibco BRL, Gaithersburg, Md.) in the buffer recommended by the supplier, and in the presence of 125 U/ml of RNAsin (Promega) and 1 mM dNTPs (Pharmacia). Primers were either oligo(dT) (Pharmacia) or a specifically designed primer. The reaction products were used as templates for PCR performed with specific primers. These reactions were carried out in 50 $\mu$l containing 2 units of Taq DNA Polymerase (Boehringer Mannheim, Mannheim, Germany), 200 $\mu$M dNTPs, 0.5 $\mu$M of each primer, and one tenth of the RT-PCR products. The products were purified using the QIA-quick spin system (Qiagen, Hilden, Germany).

Restriction endonuclease fingerprinting:

The protocol of Liu and Sommer (1995) was followed with slight modifications. RT-PCR was performed as described above, using primers defining PCR products of 1.0–1.6 kb. One hundred ng of amplified DNA was digested separately with 5 or 6 restriction endonucleases in the presence of 0.2 units of shrimp alkaline phosphatase (United States Biochemicals, Cleveland, Ohio). Following heat inactivation at 65° C. for 10 minutes, the digestion products corresponding to the same PCR product were pooled, denatured at 96° C. for 5 minutes and immediately chilled on ice. Ten ng of this fragment mixture was labeled in the presence of 6 $\mu$Ci of [$\gamma$-$^{33}$P]ATP and 1 unit of T4 polynucleotide kinase (New England Biolabs, Beverly, Mass.) at 37° C. for 45 minutes. Twenty $\mu$l of stop solution containing 95% formamide, 20 mM EDTA, 0.05% bromophenol blue, 0.05% xylene cyanol, and 10 mM NaOH were added, and the samples were boiled for 3 minutes and quick-chilled on ice. Electrophoresis was performed in 5.6% polyacrylamide gels in 50 mM Tris-borate, pH 8.3, 1 mM EDTA at constant power of 12 W for 3 hours at room temperature, with a fan directed to the glass plates, keeping them at 22–24° C. The gels were dried and subjected to autoradiography.

Direct sequencing of PCR products:

Five hundred ng of PCR products was dried under vacuum, resuspended in reaction buffer containing the sequencing primer, and the mixture was boiled and snap-frozen in liquid nitrogen. The Sequenase II system (Unites States Biochemicals) was used to carry out the sequencing reaction in the presence of 0.5 $\mu$g of single-strand binding protein (T4 gene 32 protein, United States Biochemicals). The reaction products were treated with 0.1 $\mu$g of proteinase K at 65° C. for 15 minutes, separated on a 6% polyacrylamide gel, and visualized by autoradiography.

Using the methods described herein above the ATM transcript was scanned for mutations in fibroblast and lymphoblast cell lines derived from an extended series of A-T patients from 13 countries, all of whom were characterized by the classical A-T phenotype. The analysis was based on RT-PCR followed by restriction endonuclease fingerprinting (REF). REF is a modification of the single-strand conformation polymorphism (SSCP) method, and enables efficient detection of sequence alterations in DNA fragments up to 2 kb in length (Liu and Sommer, 1995).

Briefly, after PCR amplification of the target region, multiple restriction endonuclease digestions are performed prior to SSCP analysis, in order to increase the sensitivity of the method and enable precise localization of a sequence alteration within the analyzed fragment. The coding sequence of the ATM transcript, which spans 9168 nucleotides (SEQ ID No:2) (Savitsky et al., 1995b), was thus divided into 8 partly overlapping portions of 1.0–1.6 Kb, and each one was analyzed separately. Sequence alterations causing. abnormal REF patterns were located and disclosed by direct sequencing. Mutations identified in this way were reconfirmed by repeating the RT-PCR and sequencing, or by testing the presence of the same mutations in genomic DNA.

In compound heterozygotes, the two alleles were separated by subcloning and individually sequenced. In some cases, agarose gel electrophoresis showed large deletions in the ATM transcript manifested as RT-PCR products of reduced sizes. The breakpoints of such deletions were delineated by direct sequencing of these products.

The 44 mutations identified to date in our patient cohort (Table 2) include 34 new ones and 10 previously published ones (Table 1). (Mutations in Table 2 are presented according to the nomenclature proposed by Beaudet & Tsui (1993); nucleotide numbers refer to their positions in the sequence of the ATM transcript (accession number U33841); the first nucleotide of the open reading frame was designated +1.) These mutations were found amongst 55 A-T families: many are unique to a single family, while others are shared by several families, most notably the 4 nt deletion, 7517del4, which is common to 6 A-T families from South-Central Italy (Table 2). According to this sample, there is a considerable heterogeneity of mutations in A-T, and most of them are "private". The proportion of homozygotes in this sample is relatively high due to a high degree of consanguinity the populations studied. It should be noted, however, that apparently homozygous patients from non-consanguineous families may in fact be compound heterozygotes with one allele not expressed.

This series of 44 A-T mutations is dominated by deletions and insertions. The smaller ones, of less than 12 nt, reflect identical sequence alterations in genomic DNA. Deletions spanning larger segments of the ATM transcript were found to reflect exon skipping, not corresponding genomic deletions. This phenomenon usually results from sequence alterations at splice junctions or within introns, or mutations within the skipped exons, mainly of the nonsense type (Cooper and Krawczak, 1993; Sommer, 1995; Steingrimsdottir et al., 1992; Gibson et al., 1993; Dietz and Kendzior, 1994). One large deletion spans about 7.5 Kb of the transcript and represents a genomic deletion of about 85 Kb within the ATM gene. Of these deletions and insertions, 25 are expected to result in frameshifts. Together with the 4 nonsense mutations, truncation mutations account for 66% of the total number of mutations in this sample. Seven in-frame deletions span long segments (30–124 aa) of the protein, and similarly to the truncation mutations, are expected to have a severe effect on the protein's structure. It should be noted that two base substitutions abolish the translation initiation and termination codons. The latter is expected to result in an extension of the ATM protein by an additional 29 amino acids. This mutation may affect the conformation of the nearby PI 3-kinase-like domain.

While the effect of the 4 small (1–3 aa) in-frame deletions and insertions on the ATM protein remains to be studied, it should be noted that one such deletion (8578del3) leads to a loss of a serine residue at position 2860. This amino acid is part of a conserved motif within the PI 3-kinase-like domain typical of the protein family to which ATM is related, and is present in 7 of 9 members of this family. The single missense mutation identified in this study, which leads to a Glu2904Gly substitution, results in a nonconservative alteration of another extremely conserved residue within this domain, which is shared by all of these proteins. The patient homozygous for this mutation, AT41RM, shows the typical clinical A-T phenotype. Measurement of radioresistant DNA synthesis in the patient's cell line revealed a typical A-T response, demonstrating that this patient has the classical A-T cellular phenotype.

As discussed herein above, the ATM gene of the present invention is probably involved in a novel signal transduction system that links DNA damage surveillance to cell cycle control. A-T mutations affect a variety of tissues and lead to cancer predisposition. This striking phenotype together with the existence of "partial A-T phenotypes" endow the study of ATM mutations with special significance.

The ATM gene leaves a great deal of room for mutations: it encodes a large transcript. The variety of mutations identified in this study indeed indicates a rich mutation repertoire. Despite this wealth of mutations, their structural characteristics point to a definite bias towards those that inactivate or eliminate the ATM protein. The nature or distribution of the genomic deletions among these mutations do not suggest a special preponderance of the ATM gene for such mutations, such as that of the dystrophin (Anderson and Kunkel, 1992) or steroid sulfatase (Ballabio et al., 1989) genes which are particularly prone to such deletions. Thus, one would have expected also a strong representation of missense mutations, which usually constitute a significant portion of the molecular lesions in many disease genes (Cooper and Krawczak, 1993; Sommer, 1995). However, only one such mutation was identified in the present study. Other point mutations reflected in this series are those that probably underlie the exon skipping deletions observed in many patients, again, exerting a severe structural effect on the ATM protein.

A technical explanation for this bias towards deletions and insertions could be a greater ability of the REF method to detect such lesions versus its ability to detect base substitution. Liu and Sommer (1995) have shown, however, that the detection rate of this method in a sample of 42 point mutations in the factor IX gene ranged between 88% and 100%, depending on the electrophoresis conditions. The 7 base substitutions detected directly by the REP method in the present study (Table 2), indicate that such sequence alterations are detected in our hands as well.

Since the expected result of most of these mutations is complete inactivation of the protein, this skewed mutation profile might represent a functional bias related to the studied phenotype, rather than a structural feature of the ATM gene that lends itself to a particular mutation mechanism. The classical A-T phenotype appears to be caused by homozygosity or compound heterozygosity for null alleles, and hence is probably the most severe expression of defects in the ATM gene. The plethora of missense mutations expected in the large coding region of this gene is probably rarely represented in patients with classical A-T, unless such a mutation results in complete functional inactivation of the protein. By inference, the only missense identified in this study, Glu2940Gly, which substitutes a conserved amino acid at the PI 3-kinase domain and clearly gives rise to a classical A-T phenotype, points to the importance of this domain for the biological activity of the ATM protein. Mutations in this domain abolish the telomere-preserving function of the TEL1 protein in *S. cerevisiae* (Greenwell et al., 1995), a protein which shows a particularly high sequence similarity to ATM (Savitsky et al., 1995b; Zakian, 1995). Another member of the family of PI 3-kinase-related proteins that includes ATM is the mammalian FRAP. Mutations in the PI 3-kinase domain abolish its autophosphorylation ability and biological activity (Brown et al., 1995). These observations, together with the mutation shown here, suggest that this domain in ATM is also likely to include the catalytic site, which may function as a protein kinase.

Genotype-phenotype relationships associated with the ATM gene appear therefore to extend beyond classical A-T. There are several examples of genes in which different mutations lead to related but clinically different phenotypes. For example, different combinations of defective alleles of the ERCC2 gene may result in xeroderma pigmentosum (group D), Cockayne's syndrome or trichothiodystrophy—three diseases with different clinical features involving UV sensitivity (Broughton et al., 1994, 1995).

Different mutations in the CFTR gene may lead to full-fledged cystic fibrosis, or only to congenital bilateral absence of the vas deferens which is one feature of this disease (Chillon et al., 1995; Jarvi et al., 1995). A particularly interesting example is the X-linked WASP gene responsible for Wiskott Aldrich syndrome (WAS), characterized by immunodeficiency, eczema and thrombocytopenia. Most of the mutations responsible for this phenotype cause protein truncations; however, certain missense mutations may result in X-linked thrombocytopenia, which represents a partial WAS phenotype, while compound heterozygosity for a severe and mild mutation results in females in an intermediate phenotype (Kolluri et al., 1995; Derry et al., 1995).

In a similar manner, genotypic combinations of mutations with different severities create a continuous spectrum of phenotypic variation in many metabolic diseases.

Which phenotypes are most likely to be associated with milder ATM mutations? Since cerebellar damage is the early and severe manifestation of A-T, it is reasonable to assume that the cerebellum might also be affected to some extent in phenotypes associated with milder ATM mutations. Such phenotypes may include cerebellar ataxia, either isolated (Harding, 1993) or coupled with various degrees of immunodeficiency. The latter combination has indeed been described, sometimes with chromosomal instability, and is often designated "ataxia without telangiectasia" (Ying and Decoteau, 1983; Byrne et al., 1984; Aicardi et al., 1988; Maserati, 1988; Friedman and Weitberg, 1993). Friedman and Weitberg (1993) recently suggested a new clinical category of "ataxia with immune deficiency" that would include A-T as well as other cases of cerebellar degeneration with immune deficits. Evaluation of patients with cerebellar disorders with the present invention may reveal a higher frequency of such cases than previously estimated. However, in view of the pleiotropic nature of the ATM gene, the range of phenotypes associated with various ATM genotypes may be even broader, and include mild progressive conditions not always defined as clear clinical entities. Screening for mutations in this gene in such cases may reveal wider boundaries for the molecular pathology associated with the ATM gene.

EXAMPLE 4

Identification of the Mouse Atm Gene

MATERIALS AND METHODS

Library screening:

An oligo(dT)-primed mouse brain cDNA library in a Uni-Zap XR vector, a mouse 129Sv genomic library (Stratagene, San Diego, Calif.) and a randomly primed mouse brain cDNA library in lambda-gt10 (Clontech, Palo Alto, Calif.) were used. $10^6$ pfu were screened with each probe. The libraries were plated at a density of $5 \times 10^4$ pfu per 140 mm plate, and two sets of replica filters were made using Qiabrane nylon membranes (Qiagen, Hilden, Germany) according to the manufacturer's instructions. Filters were prehybridized for 2 hours at 65° C. in 6×SSC, 5×Denhardt's, 1% N-laurylsarcosyl, 10% dextran sulfate and 100 $\mu$g/ml sheared salmon sperm DNA. Hybridization was performed at 65° C. for 16–18 hours in the same solution containing $10^6$ cpm/ml of probe labeled with $^{32}$P-dCTP by random priming. Final washes were made for 30 minutes in 0.5× SSC, 0.1% SDS at 50° C. Positive clones were plaque-purified using standard techniques.

RT-PCR:

First strand synthesis was performed using 2 $\mu$g of total RNA from mouse 3T3 cells with an oligo(dT) primer and Superscript II (Gibco-BRL, Gaithersburg, Md.). The reaction products served as templates for PCR with gene-specific primers.

Sequence analysis:

The insert of cDNA clone 15-1 (see below) was excised from a gel, self-ligated to form concatamers, and sonicated to obtain random fragments. These fragments were size-fractionated by gel electrophoresis, and the 1.0- to 1.5-kb fraction was extracted from the gel and subcloned in a pBluescript vector (Stratagene). The end portions of individual clones were sequenced with vector-specific primers in an automated sequencer (Model 373A, Applied Biosystems Division, Perkin Elmer), and the sequences were aligned with the AutoAssembler program (Applied Biosystems). In the final sequence, each nucleotide position represents at least three independent overlapping readings. In smaller cDNA inserts, sequencing was initiated with vector-specific primers, and additional sequencing primers were designed for both strands as sequencing progressed. Sequencing of RT-PCR products was performed with the PCR primers.

Fluorescence in-situ hybridization (FISH):

Preliminary chromosomal localization of the Atm gene was determined by FISH analysis. Mouse metaphase chromosomes were prepared from concanavalin A (conA) stimulated lymphocytes obtained after splenectomy as described by Boyle at al. (1992), with slight modifications. Briefly, homogenized spleen tissue was cultured for 48 hours in RPMI 1640 medium supplemented with 20% fetal bovine serum, 6 $\mu$g/ml concanavalin A, and 86.4 $\mu$M β-mercaptoethanol. The cell cycle was synchronized by incubation with methotrexate (17 hours, 4.5 mM). The S-phase block was released with BrdU (30 $\mu$M) and FUdR (0.15 $\mu$g/ml) for 5 hours. Colcemid was added for 10 minutes; the cells were incubated in KCl (0.55%) and fixed with methanol/acetic acid (3:1). The mouse Atm genomic clone used for FISH analysis was obtained by screening the mouse 129Sv genomic library with a human 236 bp PCR probe corresponding to nt 5381–5617 of the human ATM cDNA. Sequence analysis confirmed that this clone contains a 177 bp exon corresponding to nt 5705–5881 of the mouse Atm cDNA.

The mouse Atm genomic clone was labeled by nick-translation with digoxigenin-11dUTP (Boehringer Mannheim, Indianapolis, Ind.). To facilitate chromosome identification, a biotinylated mouse chromosome 9-specific painting probe (Vector Laboratories, Burlingame, Calif.) was used for cohybridization. The probe sequences and metaphase chromosomes were heat denatured separately. Hybridization was performed for 15 hours at 37° C. in a solution containing 50% formamide, 2×SSC, and 10% dextran sulfate. Post-hybridization washes were performed as described by Ried et al. (1992). The biotinylated probe sequences were detected by incubation with avidin conjugated to FITC (Vector Laboratories), and the digoxigenin labeled sequences by incubation with mouse anti-digoxin and goat anti-mouse conjugated to TRITC (Sigma Chemicals, St. Louis, Mo.). Chromosomes were counterstained with DAPI. The fluorescent signals were sequentially acquired using a cooled CCD camera (Photometrics, Tucson, Ariz.) coupled to a Leica DMRBE microscope. Gray scale images were converted to tintscale using Gene Join (Ried et al., 1992).

Linkage analysis:

Interspecific backcross progeny were generated by mating (C57BL/6J×M. spretus)F1 females and C57BL/6J males, as described by Copeland and Jenkins (1991). A total of 205 $N_2$ mice were used to map the Atm locus as described herein below. Southern blot analysis was performed (Jenkins et al., 1982). All blots were prepared with Hybond-N$^+$ membrane (Amersham). The Atm probe, REF3, a PCR-amplified fragment from the Atm mouse cDNA representing nt 6000–7264 was labeled with [$\alpha^{32}$P]dCTP using a random priming labeling kit (Stratagene); washing was done to a final stringency of 0.5×SSCP, 0.1% SDS, 65° C. Fragments of 4.9, 3.6, and 1.4 kb were detected in HindIII-digested C57BL/6J DNA and fragments of 5.6 and 4.3 kb were detected in HindIII-digested M. spretus DNA. The presence or absence of the 5.6 and 4.3 kb M. spretus-specific fragments, which cosegregated, were followed in the backcross mice.

A description of the probes and RFLPs for the loci linked to Atm, including glutamate receptor, ionotropic, kainate 4 (Grik4); thymus cell antigen-1 theta (Thy1); Casitas B-lineage lymphoma (Cbl); CD3 antigen, gamma polypeptide (Cd3g); and dopamine receptor 2 (Drd2), has been reported previously (Kingsley at al., 1989; Regnier et al., 1989; Szpirer et al., 1994). The mouse chromosomal locations of mitochondrial acetoacetyl-CoA thiolase (Acat1) and src-kinase (Csk) were determined for the first time, herein. Recombination distances were calculated as described (Green, 1981), using the computer program SPRETUS MADNESS. Gene order was determined by minimizing the number of recombination events required to explain the allele distribution patterns.

The Csk probe, a 2.2 kb EcoRI/XhoI fragment derived from the mouse cDNA (Thomas et al., 1991), was labeled with [$\alpha^{32}$P]dCTP using a nick] translation labeling kit (Boehringer Mannhein); washing was done to a final stringency of 0.1×SSPE, 0.1% SDS, 65° C. A fragment of 9.4 kb was detected in HindIII-digested C57BL/6J DNA and a fragment of 5.8 kb was detected in HindIII-digested M. spretus DNA. The presence or absence of the 5.8 kb M. spretus-specific fragment was followed in the backcross mice. The Acat1 probe, a 1.4 kb fragment from the Acat rat cDNA (Fukao et al., 1990), was labeled by nick translation and washed from the blots to a final stringency of 0.8×SSCP, 0.1% SDS, 65° C. A fragment of 23 kb was detected in EcoRI-digested C57BL/6J DNA, and fragments of 22 and 5.4 kb were detected in EcoRI-digested M. spretus DNA. The presence or absence of the 22 and 5.4 kb M. spretus-specific fragments, which cosegregated, were followed in the backcross mice.

RESULTS

Figure 3:
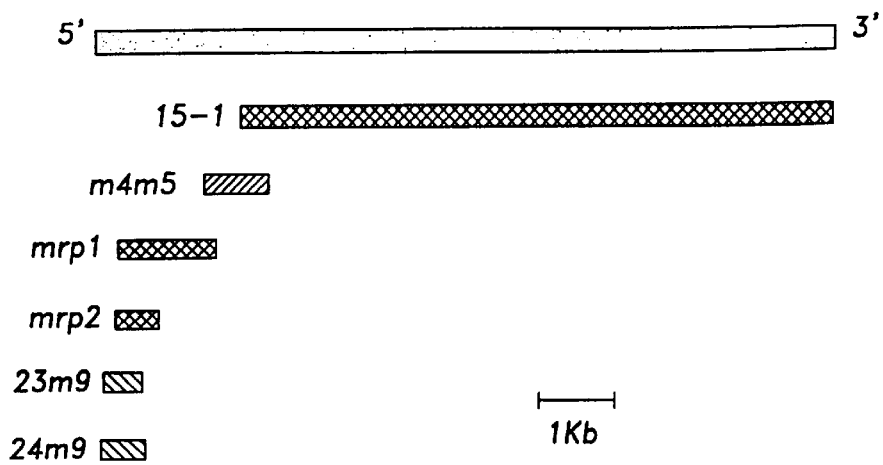
FIG. 3 is a diagram of the molecular cloning of the coding region of the Atm transcript wherein the top bar depicts the entire length of the cloned sequence, double crosshatched bars are cDNA clones, dotted bars are RT-PCR products, and bars with diagonal lines are PCR products obtained from a cDNA library.

Molecular cloning of the coding sequence of Atm gene:

In search of a cDNA clone derived from a murine gene corresponding to the human ATM, $10^6$ pfu from a mouse brain cDNA library were screened with a PCR product corresponding to nt 4021–8043 of the human ATM cDNA (Savistky et al., 1995b; the first nucleotide of the open reading frame was numbered 1). Fifteen positive clones were identified, and the longest one, of 8.5 kb (designated 15-1; FIG. 3), was further analyzed. High-stringency hybridization of this clone to panels of radiation hybrids, YAC and cosmid clones representing the human ATM locus (Rotman et al.,1994; Shiloh, 1994; Savitsky et al., 1995a,b) showed strongly hybridizing sequences within the ATM locus. Northern blotting analysis and subsequent sequencing and alignment with the human ATM transcript confirmed that 15-1 corresponded throughout its length to the human gene but was missing the 5' end of the corresponding mouse transcript.

Screening of a randomly primed mouse brain cDNA library with a probe corresponding to the 5' region of the human ATM transcript (nt 1–2456) identified 2 clones, MRP1 and MRP2, of 1.3 and 0.6 kb, respectively (FIG. 3). The gap between clones 15-1 and MRP1 was subsequently bridged using RT-PCR with primers derived from these clones, which produced the fragment m4m5 of 840 bp. Finally, a primer derived from the MRP1 sequence was designed and used with vector-specific primers to obtain two PCR products, 23m9 and 24m9, from the randomly primed brain cDNA library. All these clones and PCR products hybridized exclusively to the ATM locus in the human genome. Their sequences were assembled and formed a contig of 9620 nucleotides (FIG. 3; GenBank accession no. U43678).

Sequence comparisons:

The sequence of the contig shown in FIG. 3 shows an open reading frame (ORF) of 9201 nt, and includes a 41 nt 5' UTR and a 378 nt 3' UTR. These UTRs are probably not complete, in view of the length of the UTRs of the ATM transcript and the lack of a poly(A) tail in 15-1. The ORF encodes a putative protein of 3,066 amino acids with a molecular weight of 349.5 kDa (SEQ ID No:3). When the nucleotide and amino acid sequences corresponding to the coding regions of the mouse and human ATM transcripts were aligned, there was an overall identity of 85% at the nucleotide sequence level, and an 84% identity and 91% similarity at the amino acid level. The difference of 10 amino acids between the human and mouse proteins is the net sum of several insertions and deletions in both proteins, when compared to each other. The PI 3-kinase domain found in ATM and other related proteins was identified in the mouse sequence (SEQ ID No:12, aa residues 2750–3055), as was the leucine zipper (SEQ ID No:12, aa residues 1211 to 1243) present in the human ATM protein (SEQ ID No:3, aa residues 2855–2875 and 1217–1238 respectively).

These results indicated that applicants had obtained the entire coding sequence of Atm, the murine homolog of the human ATM gene. It is noteworthy that the human and mouse proteins were most similar within the PI 3-kinase domain at the carboxy terminus (94% identity, 97% similarity), while the other portions of these proteins show variable identity and similarity reaching a minimum of 70% and 82%, respectively, in some regions (FIG. 4).

Expression pattern:

A Northern blot representing several mouse tissues (Clontech) was probed with a fragment representing nt 2297–5311 of the Atm transcript. This probe identified a message of about 13 kb in brain, skeletal muscle and testis, which was barely detectable in heart, spleen, lung and kidney. In the testis, another band of about 10.5 kb was observed at about 50% intensity compared to the 13 kb band. This pattern seems to represent greater differences in expression levels between tissues, compared to the more uniform pattern observed in human tissues (Savitsky et al., 1995a). In addition, the 10.5 kb band, which may represent mRNA species with alternative polyadenylation, was not detected in any of 16 human tissues tested previously, but was clearly observed in cultured human fibroblasts (Savitsky et al., 1995a).

Chromosomal localization of the Atm gene by FISH:

Initial chromosomal localization of the mouse Atm gene was determined by dual-color FISH. A digoxigenin-labeled probe was cohybridized with a chromosome painting probe specific for mouse chromosome 9, that confirms the identification of DAPI-stained mouse chromosomes. Mouse chromosome 9 contains homologous regions of human chromosomes 11q, including 11q22-23, the region to which the human ATM gene was assigned. Twelve randomly selected metaphases were analyzed. Signals were observed in 90% of the cells on mouse chromosome 9C. Other chromosomal positions were not observed.

Genetic mapping of the Atm gene:

The Atm gene was further localized on the genetic map of mouse chromosome 9 using interspecific backcross analysis using progeny derived from matings of [(C57BL/6J×M. spretus) $F_1$×C57BL/6J] mice. This interspecific backcross mapping panel has been typed for over 2000 loci which are well distributed among all the autosomes as well as the X chromosome (Copeland and Jenkins, 1991). C57BL/6J and M. spretus DNAs were digested with several enzymes and analyzed by Southern blot hybridization for informative restriction fragment length polymorphisms (RFLPs), using a probe representing nt 6000–7264 of the Atm transcript.

Figures 5A, 5B:
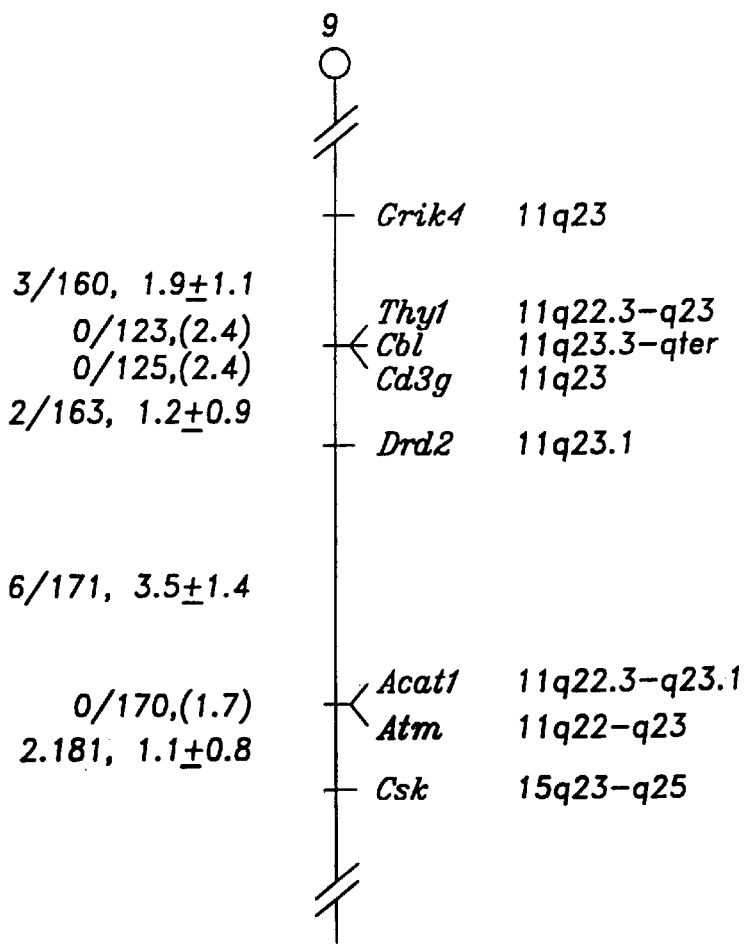
FIGS. 5A–B diagrams the chromosomal location of Atm in the mouse genome with (A) showing the segregation patterns of Atm and flanking genes wherein each column represents the chromosome identified in the backcross progeny that was inherited from the (C57BL/6J×M. spretus) $F_1$ parent, and shaded boxes represent the presence of a C57BL/6J allele and empty boxes represent the presence of a M. spretus allele, the number of offspring inheriting each type of chromosome is listed at the bottom of each column, and (B) is a diagram of a partial chromosome 9 linkage map showing the location of Atm in relation to linked genes with the number of recombinant $N^2$ animals over the total number of $N_2$ animals typed plus the recombination frequencies, expressed as genetic distance in centimorgans (±one standard error) is shown for each pair of loci to the left of the map, where no recombinants were found between loci, the upper 95% confidence limit of the recombination distance is given in parentheses, the positions of loci in human chromosomes are shown to the right of the map.

The results indicated that Atm is located in the proximal region of mouse chromosome 9 linked to Grik4, Thy1, Cbl, C3g, Drd2, Acat1 and Csk (FIG. 5B). Ninety-one mice were analyzed for every marker and are shown in the segregation analysis (FIG. 5A), however up to 203 mice were typed for some pairs of markers. Each locus was analyzed in pairwise combinations for recombination frequencies using the additional data. The ratios of the total number of mice analyzed for each pair of loci and the recombination frequencies between the loci are shown in FIG. 5B.

Two mapping methods were used to assign the Atm gene to chromosome 9, band 9C. Comparative gene mapping in mouse and human has revealed numerous regions of homology between the two species (Copeland et al., 1993). (References for the human map positions of loci cited in this study can be obtained from GDB (Genome Database), a computerized database of human linkage information maintained by The William H. Welch Medical Library of The Johns Hopkins University (Baltimore, Md.).) This is clearly demonstrated between this portion of mouse chromosome 9 and human chromosome 11q22-23. The human homologs of Grik4, Thy1, Cbl, Cd3g, Drd2, Acat1 and Atm map to 11q22-23. It is noteworthy that, similarly to the close map locations of Atm and Acat1 in the mouse, ATM and ACAT1 lie about 200 kb apart in the human genome. The mapping of Atm refines the distal end of the human 11q22-23 homology unit. Csk, 1.1 cM distal to Acat and Atm, maps to human chromosome 15q23-q25. The average length of a conserved autosomal segment in mice was estimated at 8.1 cM (Nadeau and Taylor, 1984). The conserved segment on mouse chromosome 9 which corresponds to 11q22-23 in humans, extends centromeric to Grik4 and spans approximately 19 cM.

The high degree of conservation between the human and mouse proteins suggests similar roles; however, the difference in expression patterns between mice and humans suggested by these northern results may lead to differences between the phenotypes associated with these proteins in the two organisms. To date, no phenotype identical to A-T has been reported in the mouse.

The derived chromosome 9 interspecific map of the present invention was compared with a composite mouse linkage map from Mouse Genome Database (The Jackson Laboratory, Bar Harbor, Me.), that reports location of many uncloned mouse mutations. Only one uncloned mouse mutation, luxoid (lu), lies in the vicinity of Atm, but this skeletal abnormality is highly unlikely to represent a mouse disorder corresponding to A-T. The mouse phenotype closest to A-T is severe combined immune deficiency (SCID) on mouse chromosome 16. It is characterized by a deficiency in mature B and T lymphocytes, radiation sensitivity, chromosomal instability, defective rejoining of DNA double-strand breaks and defective V(D)J recombination (Bosma and Carroll, 1991). This phenotype is caused by defects in one of the proteins with a PI 3-kinase domain, the catalytic subunit of DNA-dependent protein kinase (DNA-PKcs) (Blunt et al., 1995; Hartley et al., 1995). The reason for lack of a mouse phenotype associated with the Atm gene may be that, unlike in humans, such a phenotype is either embryonic lethal, or considerably milder than in humans. As described herein below, a knockout mouse for the Atm gene in mice has been generated and the phenotype appears in young mice to be somwhat milder than in humans.

Using a 200 bp PCR product from the human ATM sequence, mouse genomic clones were screened and isolated. The sequence of the 200 bp PCR product corresponds approximately to ATM exons 40 and 41 as set forth in SEQ ID No:24. The targeted disruption of the homologous mouse gene (Atm) involves insertion of a neomycin cassette in the targeted exon and homologous recombination in 129/Sv-ES cells. Generation and analysis of knockout mice were done in collaboration with Dr. Anthony Wynshaw-Boris at the NIH. Neomycin resistant clones were analyzed by PCR and Southern, and injected into blastocysts. Targeted ES cells showed moderate radiosensitivity. No outward phenotypic differences were observed in the heterozygous progenies thus far. Heterozygous matings resulted in homozygote nulls whose preliminary analysis are shown to be infertile, are radiosensitive and show stunted growth. Techniques used are as described in Hogan et al., *Manipulating the Mouse Embryo: A Laboratory Manual*, Cold Spring Harbor Laboratory, New York, (1994).

EXAMPLE 5

Generation of Antibodies Against the ATM Protein

Antibodies, both polyclonal and monoclonal, were generated against peptide sequences based on the human ATM sequence as set forth in SEQ ID Nos:4–7,13–15:

HEPANSSASQSTDLC (SEQ ID No:4),
CKRNLSDIDQSFDKV (SEQ ID No:5),
PEDETELHPTLNADDQEC (SEQ ID No:6),
CKSLASFIKKPFDRGEVESMEDDTNG (SEQ ID No:7),
CRQLEHDRATERRKKEVEKFK (SEQ ID No:13)
CLRIAKPNVSASTQASRQKK (SEQ ID No:14)
CARQEKSSSGLNHILAA (SEQ ID No:15)

Two rabbits each and six mice each were immunized with each of the antigens.

Additional peptide sequences based on the mouse atm sequence to which polyclonal antibodies were raised includes:

CRQLEHDRATERKKEVDKF (SEQ ID No:16)
CFKHSSQASRSATPANSD (SEQ ID No:17)
RPEDESDLHSTPNADDQEC (SEQ ID No:18)

Glutathione S-transferase recombinant fusions with the ATM fragments from which polyclonals and monoclonals have been raised are set forth in SEQ ID Nos:19–23.

Antibodies raised against the ATM protein detect monospecifically a high molecular weight of the expected size of 350 kDa on Western blots of protein lysates derived from fibroblast and lymphoblastoid cell lines. Because of the high frequency of truncation mutations in the ATM gene, mutated ATM protein can be identified if such proteins are stable. Indirect immunofluorescence showed the ATM protein to be predominantly nuclear. Cell-fractionation studies of normal fibroblast cells identified the presence of the ATM protein in both the nuclear and microsomal fractions.

Throughout this application various publications and patents are referenced by citation or number, respectively. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

*illustrates several mutations found in A—T patients*

| Patient[1] | Ethnic/ geographic origin | Complementation group[4] | Mutation mBNA sequence change | Protein alteration | Codon[9] | Patient's genotype[10] |
|---|---|---|---|---|---|---|
| AT2RO | Arab | A | Deletion of 11 nt[5] | Frameshift, truncation | 499 | Homozygote |
| AT3NG | Dutch | A | Deletion of 3 nt | Deletion, 1 residue[8] | 1512 | Compound heterozygote |
| AT15LA | Phillipine | A | Insertion, +A | Frameshift, truncation | 557 | Compound heterozygote |
| AT3LA[2] AT4LA[2] | African-American | C | Deletion of 139 nt[6]/ Deletion of 298 nt[6] | Frameshift, truncation | 1196 | Compound heterozygote |
| AT2BR | Celtic/Irish | C | Deletion, 9 nt | Deletion, 3 residues | 1198–1200 | Homozygote |
| AT1ABR AT2ABR | Australian (Irish/British) | E | Deletion, 9 nt | Deletion, 3 residues | 1198–1200 | Homozygote |
| AT5BI[2] AT6BI[2] | Indian/English | D | Deletion, 6 nt | Deletion, 2 residues | 1079–1080 | Compound heterozygote |
| F-2079[3] | Turkish | ND | Insertion, +C[5] | Frameshift, truncation | 504 | Homozygote |
| AT29RM | Italian | ND | Deletion of 175 nt | Frameshift, truncation | 132 | Homozygote |
| AT103LO | Canadian | ND | Insertion, +A | Frameshift, truncation | 1635 | Homozygote |
| F-596[3] | Palestinian Arab | ND | Deletion[7] | Truncation | Most of ORF | Homozygote |

[1]Cell line designation.
[2]Sibling patients in both of whom the same mutation was identified.
[3]Patient expected to be homozygous by descent for an A—T mutation.
[4]According to the methods of Jaspers et al. (1988) ND: not determined.
[5]An identical sequence change was observed in genomic DNA
[6]No evidence for deletion was observed in genomic DNA. In both siblings, a normal mRNA was observed in addition to the two deleted species. The two deleted mRNAs may represent abnormal splicing events caused by a splice site mutation.
[7]Reflects a genomic deletion segregating with the disease in Family N.
[8]The deleted serine residue is located within the PI3-kinase signature sequence (1507–1527 of SEQ ID No:2).
[9]Numbers refer to residue positions in SEQ ID No:2.
[10]In all the compound heterozygotes, the second mutation is still unidentified.

TABLE 2

*Mutations in the ATM gene in patients with classical A—T.*

| mRNA sequence change[1] | Predicted protein alteration | Codon[6] | Patient | Ethnic/ geographical origin | Genotype[11] |
|---|---|---|---|---|---|
| Truncations and exon skipping deletions: | | | | | |
| 9001delAG | Truncation | 3001 | 91RD90[9] | Turkish | Hmz |
| 8946insA | Truncation | 2983 | AP1O3LO | American | Hmz |
| 8370G->A | Trp->ter; truncation | 2769 | AT2SF | American | Compd Htz |
| 8283delTC | Truncation | 2762 | AT28RM | Italian | Compd Htz |
| 8269del403[3] | Truncation | 2758 | AT12RM | Italian | Hmz |
| 8269del1503 | Del, 50 aa | 2758 | F-2086 | Turkish | Compd Htz |
| | | | GM9587 | American | Compd Htz |
| 8140C->T | Gln->ter; truncation | 2714 | IARC12/AT3 | French | Hmz |
| 7883del5 | Truncation | 2628 | ATF104 | Japanese | Hmz |
| | | | JCRB316 | Japanese | Compd Htz |
| 7789del139/7630del298[4,5] | Truncation | 2544 | AT4LA | Carribean Black | Comp Htz |
| 7630del159[3] | Del, 53 aa | 2544 | F-2086 | Turkish | Compd Htz |
| | | | AT13BER | | Compd Htz |
| 7517del4 | Truncation | 2506 | AT43RM[10] | Italian | Hmz |
| | | | AT59RM[10] | Italian | Hmz |
| | | | AT22RM[10] | Italian | Hmz |
| | | | AT57RM[10] | Italian | Compd Htz |
| | | | AT7RM[10] | Italian | Compd Htz |
| | | | AT8RM[10] | Italian | Compd Htz |
| 6573del5 | Truncation | 2192 | AT12ABR | Australian | Compd Htz |
| 6348del105[3] | Del, 35 aa | 2116 | IARC15/AT4 | French | Hmz |
| 6199del149[3] | Truncation | 2067 | WG1101 | Canadian | Hmz |
| 5979del5 | Truncation | 1994 | AT5RM | Italian | Compd Htz |
| 5712insA | Truncation | 1905 | AT15LA | Philippino | Compd Htz |
| 5554insC | Truncation | 1852 | F-2079[9] | Turkish | Hmz |
| 5539del11 | Truncation | 1847 | AT2RO[9] | Arab | Hmz |
| 5320del355[6] | Truncation | 1774 | AT7RM | Italian | Compd Htz |
| 5320del7 | Truncation | 1774 | AT2SF | American | Compd Htz |

TABLE 2-continued

Mutations in the ATM gene in patients with classical A—T.

| mRNA sequence change[1] | Predicted protein alteration | Codon[6] | Patient | Ethnic/ geographical origin | Genotype[11] |
|---|---|---|---|---|---|
| 5178del142[3] | Truncation | 1727 | AT50RM | Italian | Compd Htz |
| 4612del165[3] | Del, 55 aa | 1538 | ATL105 | Japanese | Hmz |
| 44437del175[3] | Truncation | 1480 | AT29RM | Italian | Hmz |
| 4110del127[3] | Truncation | 1371 | AT2TAN[9] | Turkish | Hmz |
| 3403del174[3] | Del, 58 aa | 1135 | F-2095 | Turkish | Compd Htz |
| 2839del83[3] | Truncation | 947 | F-2080[9] | Turkish | Hmz |
|  |  |  | AT10TAN[9] | Turkish | Hmz |
| 2467del372[3,5] | Del, 124 aa | 823 | AT6LA | English/Irish | Hmz |
| 2377del90[3] | Del, 30 aa | 793 | AT21RM[9] | Italian | Hmz |
| 22284delCT | Truncation | 762 | F-169[9] | Palestinian Arab | Hmz |
| 2125del125[3] | Truncation | 709 | F-2078[9] | Turkish | Hmz |
| 2113delT | Truncation | 705 | AT5RM | Italian | Compd Htz |
| 1563delAG[5] | Truncation | 522 | AT8LA[9] | Swiss/German | Hmz |
| 1339C->T | Arg->ter; truncation | 447 | F-2005[9] | Druze | Hmz |
| 1240C->T | Gln->ter; truncation | 414 | AT26RM | Italian | Hmz |
| 755delGT | Truncation | 252 | AT24RM | Italian | Hmz |
| 497del7514[7] | Truncation | 166 | F-596[9] | Palestinian-Arab | Hmz |
| −30del215 | Incorrect* initiation | 5′ UTR | F-303 | Bedouine | Hmz |
| In-frame genomic deletions and insertion: |  |  |  |  |  |
| 8578del3 | Del, 1 aa | 2860 | AT3NG | Dutch | Compd Htz |
| 7636del9 | Del, 3 aa | 2547 | AT2BR | Celtic/Irish | Hmz |
|  |  |  | AT1ABR | Australian (Irish) | Hmz |
|  |  |  | AT1SF | American | Compd Htz |
| 7278del6[5] | Del, 2 aa | 2427 | AT5BI | Indian/English | Compd Htz |
|  |  |  | GM5823 | English | Compd Htz |
| 5319ins9 | Ins, 3 aa | 1774 | 251075-008T | Finnish | Compd Htz |
| Other base substitutions: |  |  |  |  |  |
| 9170G->C | ter->Ser Extension of protein by 29 amino acids | ter | F-2089[9] | Turkish | Hmz |
| 8711A->G | Glu2904Gly | 2904 | AT41RM | Italian | Hmz |
| 2T->C | Met->Thr Initiation codon abolished | 1 | AT8BI | British | Compd Htz |

[1]Presented according to the nomenclature proposed by Beaudet & Tsui (1993). Nucleotide numbers refer to their positions in the sequence of the ATM transcript (accession number U33841). The first nucleotide of the open reading frame was designated +1.
[2]Three adjacent exons skipped.
[3]One exon skipped.
[4]This allele produces two transcripts, with one or two ajacent exons skipped.
[5]The same mutation was found in two affected siblings.
[6]Two exons skipped.
[7]This transcript is produced by an allele containing a large genomic deletion spanning approximately 85 Kb within the ATM gene in Family ISAT 9 (Savitsky, et al., 1995a).
[8]For deletions, the number of the first codon on the amino terminus side is indicated. Codon numbers are according to the ATM protein sequence published by Savitsky et al. (1995b). In each section of the table, the mutations are ordered according to the codon numbers in this column, beginning with the one closest to the carboxyl terminus.
[9]Consanguineous family.
[10]All patients are from the same region.
[11]Genotypic combinations in which the mutation was found. Hmz: homozygote, Compd Htz: compound heterozygote. Each patient represents one family.

TABLE 3

Comparison of the ATM protein to related proteins in different species

| Protein | Size (aa) | Species | % identity/similarity Carboxy terminus* | % identity/similarity Rest of protein** |
|---|---|---|---|---|
| TEL1 | 2789 | S. cerevisiae | 45/67 | 19/44 |
| MEC1 | 2368 | S. cerevisiae | 37/63 | 20/46 |
| rad3 | 2386 | S. pombe | 38/59 | 21/46 |
| ME1-41 | 2356 | D. melanogaster | 37/59 | 22/47 |
| TOR1 | 2470 | S. cerevisiae | 33/58 | 19/45 |
| TOR2 | 2473 | S. cerevisiae | 35/60 | 20/45 |

TABLE 3-continued

Comparison of the ATM protein to related proteins in different species

| Protein | Size (aa) | Species | % identity/similarity | |
|---|---|---|---|---|
| | | | Carboxy terminus* | Rest of protein** |
| mTOR | 2549 | R. norvegicus | 32/59 | 18/44 |
| DNA-PK$_{cs}$ | 4096 | H. sapiens | 28/51 | 18/43 |

*350 aa of the carboxy terminus, containing the P1-3 kinase-like domain.
**The entire protein excluding the carboxy terminal 350 aa. An average value is given, since the values obtained for different parts of the proteins vary only by 1–3%.

REFERENCES

Aicardi et al., "Ataxia-ocularmotor apraxia: A syndrome mimicking ataxia-telangiectasia" Ann. Neurol. 24:497–502 (1988).

Aksentijevitch et al., "Familial Mediterranean fever in Moroccan Jews: Demonstration of a founder effect by extended haplotype analysis" Am. J. Hum. Genet., 53:644–651 (1993).

Ambrose et al., "A physical map across chromosome 11q22-23 containing the major locus for ataxia-telangiectasia. Genomics, 21:612–619 (1994).

Anderson and Kunkel, "The molecular and biochemical basis of Duchenne muscular dystrophy" Trends Biochem. Sci. 17:289–292 (1992).

Attree et al., "The Lowe's oculocerebrorenal syndrome gene encodes protein highly homologous to inositol polyphosphate-5-phosphatase" Nature, 358:239–242 (1992).

Ballabio et al., "Molecular heterogeneity of steroid sulfatase deficiency: a multicenter study on 57 unrelated patients, at DNA and protein levels" Genomics 4:36–40 (1989).

Barker, "A more robust, rapid alkaline denaturation sequencing method", BioTechniques, Vol. 14, No. 2, pp. 168–169 (1993).

Berger et al., "Isolation of a candidate gene for Norrie disease by positional cloning" Nature Genet. 1:199–203, (1992)

Beaudet and Tsui, "A suggested nomenclature for designating mutations" Hum. Mutat. 2:245–248 (1993).

Blunt et al., 1995. Defective DNA-dependent protein kinase activity is linked to V(D)J recombination and DNA repair defects associated with the murine scid mutation. Cell 80:813–823.

Bosma and Carroll, 1991. The SCID mouse mutant: definition, characterization, and potential uses. Rev. Immunol. 9:323–350.

Boyle et al., 1992. Rapid physical mapping of cloned DNA on banded mouse chromosomes by fluorescence in situ hybridization. Genomics 12:106–115.

Broughton et al., "Mutations in the xeroderma pigmentosum group D DNA repair/transcription gene in patients with trichothiodystrophy" Nature Genet. 7:189–194 (1994).

Broughton et al., "Molecular and cellular analysis of the DNA repair defect in a patient in xeroderma pigmentosum group D who has the clinical features of xeroderma pigmentosum and Cockayne's syndrome" Am. J. Hum. Genet. 56:167–174 (1995).

Brown et al., "Control of p70 S6 kinase by kinase activity of FRAP in vivo" Nature 377:441–446 (1995).

Buckler et al., "Exon amplification: a strategy to isolate mammalian genes based on RNA splicing" Proc. Natl. Acad. Sci. USA, 88:4005–4009 (1991).

Burke and Olson, "Preparation of Clone Libraries in Yeast Artificial-Chromosome Vectors" in Methods in Enzymology, Vol. 194, "Guide to Yeast Genetics and Molecular Biology", eds. C. Guthrie and G. Fink, Academic Press, Inc., Chap. 17, pp. 251–270 (1991).

Byrne et al., "Ataxia-without-telangiectasia" J Neurol. Sci. 66:307–317 (1984).

Capecchi, "Altering the genome by homologous recombination" Science 244:1288–1292 (1989).

Chakravarti et al., "Nonuniform recombination within the human beta-globin gene cluster" Am. J. Hum. Genet., 36:1239–1258 (1984).

Chelly et al., "Isolation of a candidate gene for Menkes disease that encodes a potential heavy metal binding protein" Nature Genet. 3:14–19 (1993).

Chessa et al., "Heterogeneity in ataxia telangiectasia: classical phenotype associated with intermediate cellular radiosensitivity" Am. J. Med. Genet. 42:741–746 (1992).

Chillon et al., "Mutations in the cystic fibrosis gene in patients with congenital absence of the vas deferens" New Engl. J. Med. 332:1475–1480 (1995).

Church et al., "Isolation of genes from complex sources of mammalian genomic DNA using exon amplification" Nature Genet. 6:98–104 (1993).

Collins, F. S. "Positional cloning: let's not call it reverse anymore" Nature Genet., 1:3–6 (1992).

Cooper and Krawczak, Human gene mutation. BIOS Scientific Publishers, London (1993).

Copeland and Jenkins, 1991. Development and applications of a molecular genetic linkage map of the mouse genome. Trends Genet. 7:113–118.

Copeland et al., 1993. A genetic linkage map of the mouse: current applications and future prospects. Science 262:57–66.

Davies et al., "Targeted alterations in yeast artificial chromosomes for inter-species gene transfer", Nucleic Acids Research, Vol. 20, No. 11, pp. 2693–2698 (1992).

Derry et al., "WSP gene mutations in Wiskott-Aldrich syndrome and X-linked thrombocytopenia" Hum. Mol. Genet. 4:1127–1135 (1995).

Dickinson et al., "High frequency gene targeting using insertional vectors", Human Molecular Genetics, Vol. 2, No. 8, pp. 1299–1302 (1993).

Dietz and Kendzior, "Maintenance of an open reading frame as an additional level of scrutiny during splice site selection" Nature Genet. 8:183–188 (1994).

Duyk et al., "Exon trapping: A genetic screen to identify candidate transcribed sequences in cloned mammalian genomic DNA" Proc. Natl. Acad. Sci. USA, 87:8995–8999 (1990).

Fiorilli et al., "Variant of ataxia-telangiectasia with low-level radiosensitivity" Hum. Genet. 70:274–277 (1985).

Fodor et al, "Multiplexed biochemical assays with biological chips", Nature 364:555–556 (1993)

Foroud et al. "Localization of the AT locus to an 8 cM interval defined by STMY and S132" Am. J. Hum. Genet., 49:1263–1279 (1991).

Friedman and Weitberg, "Ataxia without telangiectasia" Movement Disorders 8:223–226 (1993).

Frohman, M. A. "On beyond classic RACE (rapid amplification of cDNA ends)" PCR Methods and Applications, 4:S40–S58 (1994).

Frohman et al., "Rapid production of full-length cDNAs from rare transcripts: Amplification using a single gene-specific oligonucleotide primer" Proc. Natl. Acad. Sci. USA, 85:8998–9002 (1988).

Fukao et al., 1990. Molecular cloning and sequence of the complementary DNA encoding human mitochondrial acetoacrtyl-coenzyme A thiolase and study of the variant enzymes in cultured fibroblasts from patients with 3-ketothiolase deficiency. J. Clin. Invest. 86:2086–2092.

Gatti et al., "Genetic haplotyping of ataxia-telangiectasia families localizes the major gene to an 850 kb region on chromosome 11q23.1" *Int. J. Radiat. Biol.* (1994).

Gatti et al. "Localization of an ataxia-telangiectasia gene to chromosome 11q22-23" *Nature,* 336: 577–580 (1988).

Gibson et al., "A nonsense mutation and exon skipping in the Fanconi anaemia group C gene" *Hum. Mol. Genet.* 2:797–799 (1993).

Gilboa et al. "Transfer and expression of cloned genes using retroviral vectors" *BioTechniques* 4(6):504–512 (1986).

Gottlieb and Jackson, "Protein kinases and DNA damage" *Trends Biochem. Sci.* 19:500–503 (1994).

Green, 1981. Linkage, recombination and mapping. In: Genetics and Probability in Animal Breeding Experiments. Oxford University Press, New York, pp. 77–113.

Greenwell et al., "TEL1, a gene involved in controlling telomere length in *Saccharomyces cerevisiae,* is homologous to the human ataxia telangiectasia (ATM) gene" *Cell* 82:823–829 (1995).

Harding, "Clinical features and classification of inherited ataxias" *Adv. Neurol.* 61:1–14 (1993).

Harnden, "The nature of ataxia-telangiectasia: problems and perspectives" *Int. J. Radiat. Biol.* 66:S13–S19 (1994).

Hartley et al., 1995. DNA-dependent protein kinase catalytic subunit: a relative of phosphatidylinositol 3-kinase and the ataxia telangiectasia gene product. Cell 82:849–856.

Hastbacka et al., "Linkage disequilibrium mapping in isolated founder populations: diastrophic dysplasia in Finland" *Nature Genet.,* 2:204–211 (1992).

Hogervorst et al., "Rapid detection of BRCA1 mutations by the protein truncation test" *Nature Genetics* 10:208–212 (1995).

Huxley et al., "The human HPRT gene on a yeast artificial chromosome is functional when transferred to mouse cells by cell fusion", *Genomics,* 9:742–750 (1991).

Jakobovits et al., "Germ-line transmission and expression of a human-derived yeast artificial chromosome", *Nature,* Vol. 362, pp. 255–261 (1993).

James et al., "A radiation hybrid map of 506 STS markers spanning human chromosome 11", *Nature Genet.* 8:70 (1994).

Jarvi et al., "Cystic fibrosis transmembrane conductance regulator and obstructive azoospermia" *The Lancet* 345:1578 (1995).

Jaspers et al., "Genetic complementation analysis of Ataxia-Telangiectasia and Nijmegen breakage syndrome: A survey of 50 patients", *Cytogenet. Cell Genet.,* 49:259 (1988).

Jenkins et al., 1982. "Organization, distribution and stability of endogenous ecotropic murine leukemia virus DNA sequences in chromosomes of *Mus musculus*". J. Virol. 43:26–36.

Kawasaki E S. Amplification of RNA. In: PCR protocols: A Guide to Methods and Applications, Innis Mass., Gelfand D H, Sninsky J J, White T J, eds. Academic Press, 1990, pp21–27.

Kerem et al., "Identification of the cystic fibrosis gene: genetic analysis" *Science,* 245:1073–1080 (1989).

Kingsley et al., 1989. A molecular genetic linkage map of mouse chromosome 9 with new regional localizations for Gsta, T3g, Ets-1, and Ldlr loci. Genetics 123:165–172.

Kolluri et al., "Identification of WASP mutations in patients with Wiskott-Aldrich syndrome and isolated thrombocytopenia reveals allelic heterogeneity at the WAS locus" *Hum. Mol. Genet.* 4:1119–1126 (1995).

Lamb et al., "Introduction and expression of the 400 kilobase precursor amyloid protein gene in transgenic mice", *Nature Genetics,* Vol. 5, pp. 22–29 (1993).

Lange et al., "Localization of an ataxia-telangiectasia gene to a 850 kb interval on chromosome 11q23.1 by linkage analysis of 176 families in an international consortium" *Am. J. Hum. Genet.* (1995).

Lehesjoki et al., "Localization of the EPM1 gene for progressive myoclonus epilepsy on chromosome 21: linkage disequilibrium allows high resolution mapping" *Hum. Mol. Genet.,* 2:1229–1234 (1993).

Lichter et al., "High-resolution mapping of human chromosome 11 by in situ hybridization with cosmid clones" *Science* 247:64–69 (1990).

Litt and Luty, "A hypervariable microsatellite revealed by in vitro amplification of a dinucleotide repeat within the cardiac muscle actin gene" *Am. J. Hum. Genet.,* 44:397–401 (1989).

Liu and Sommer, "Restriction endonuclease fingerprinting (REF): a sensitive method for screening mutations in long, contiguous segments of DNA" *BioTechniques* 18:470–477 (1995).

Llerena et al., "Spontaneous and induced chromosome breakage in chorionic villus samples: a cytogenetic approach to first trimester prenatal diagnosis of ataxia-telangiectasia syndrome" *J. Med. Genet.,* 26:174–178 (1989).

Lovett et al., "Direct selection: A method for the isolation of cDNA encoded by large genomic regions", *Proc. Natl. Acad. Sci. USA* 88, 9628 (1991).

Maserati et al., "Ataxia-without-telangiectasia in two sisters with rearrangements of chromosomes 7 and 14" *Clin. Genet.* 34:283–287 (1988).

McConville et al., "Genetic and physical mapping of the ataxia-telangiectasia locus on chromosome 11q22-23" *Int. J. Radiat. Biol.* (1994).

McConville et al., "Paired STSs amplified from radiation hybrids, and from associated YACs, identify highly polymorphic loci flanking the ataxia-telangiectasia locus on chromosome 11q22-23" *Hum. Mol. Genet.,* 2:969–974 (1993).

McConville et al., "Fine mapping of the chromosome 11q22-23 region using PFGE, linkage and haplotype analysis; localization of the gene for ataxia telangiectasia to a 5 cM region flanked by NCAM/DRD2 and STMY/CJ52.75, phi2.22" *Nucleic Acids Res.,* 18:4335–4343 (1990).

Miki et al. "A strong candidate for the breast and ovarian cancer susceptibility gene BRCA1" *Science,* 266:66–71 (1994).

Mitchison et al., "Fine genetic mapping of the Batten Disease locus (CLN3) by haplotype analysis and demonstration of allelic association with chromosome 16p microsatellite loci" *Genomics,* 16:455–460 (1993).

Morgan et al., "The selective isolation of novel .cDNAs encoded by the regions surrounding the human interleukin 4 and 5 genes" *Nucleic Acids Res.,* 20:5173–5179 (1992).

Nadeau and Taylor 1984. Lengths of chromosomal segments conserved since divergence of man and mouse. Proc. Natl. Acad. Sci. USA 81:814–818.

Orita et al. Detection of polymorphisms of human DNA by gel electrophoresis as single-strand conformation polymorphisms. Proc Natl Acad Sci USA 1989; 86:2766–2770

Oskato et al., "Ataxia-telangiectasia: allelic association with 11q22-23 markers in Moroccan-Jewish patients. 43*rd* Annual Meeting of the American Society of Human Genetics, New Orleans, La. (1993).

Ozelius et al., "Strong alleleic association between the torsion dystonia gene (DYT1) and loci on chromosome 9q34 in Ashkenazi Jews" *Am. J. Hum. Genet.* 50:619–628 (1992).

Parimoo et al., "cDNA selection: Efficient PCR approach for the selection of cDNAs encoded in large chromosomal DNA fragments" *Proc. Natl. Acad. Sci. USA*, 88:9623–9627 (1991).

Pease et al., "Light-generated oligonucleotide arrays for rapid DNA sequence analysis", *Proc. Natl. Acad. Sci. USA* 91(11):5022–5026 (1994)

Regnier et al., 1989. Identification of two murine loci homologous to the v-abl oncogene. J. Virol. 63:3678–3682.

Richard et al., "A radiation hybrid map of human chromosme 11q22-23 containing the Ataxia-Telangiectasia disease locus", *Genomics* 17, 1 (1993).

Ried et al., 1992. Simultaneous visualization of seven different DNA probes using combinatorial labeling and digital imaging microscopy. Proc. Natl. Acad. Sci. USA 89:1388–1392.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Rotman et al., "Three dinucleotide repeat polymorphisms at the ataxia-telangiectasia locus" *Human Molecular Genetics* (1994b).

Rotman et al., "A YAC contig spanning the ataxia-telangiectasia locus (groups A and C) on chromosome 11q22-23. *Genomics* (1994c).

Rotman et al., "Physical and genetic mapping of the ATA/ATC locus in chromosome 11q22-23" *Int. J. Radiat. Biol.* (1994d).

Rotman et al., "Rapid identification of polymorphic CA-repeats in YAC clones" *Molecular Biotechnology* (1995).

Savitsky et al., "A single gene with homologies to phosphatidylinositol 3-kinases and rad3+ is Mutated in all complementation groups of ataxia-telangiectasia" *Science*, 268:1749–1753 (Jun. 23, 1995a)

Savitsky et al., "The complete sequence of the coding region of the ATM gene reveals similarity to cell cycle regulators in different species" *Hum. Mol. Genet.* 4:2025–2032 (1995b).

Schedl et al., "A yeast artificial chromosome covering the tyrosinase gene confers copy number-dependent expression in transgenic mice", *Nature*, Vol. 362, pp. 258–261 (1993).

Sirugo et al., "Friedreich ataxia in Louisiana Acadians: Demonstration of a founder effect by analysis of microsatellite-generated extended haplotypes" *Am. J.Hum. Genet.*, 50:559–566 (1992).

Shiloh, "Ataxia-telangiectasia: closer to unraveling the mystery" *European Journal of Human Genetics* (1995) Shiloh et al., *Am. J. Hum. Genet.* 55 (suppl.), A49 (1994)

Sommer, "Recent human germ-line mutation: Inferences from patients with hemophilia B" *Trends Gene.* 11:141–147 (1995).

Steingrimsdottir et al., "Mutations which alter splicing in the human hypoxanthine-guanine phosphoribosyl-transferase gene" *Nucleic Acids Res.* 6:1201–1208 (1992).

Strauss et al., "Germ line transmission of a yeast artificial chromosome spanning the murine $\alpha_1$ (I) collagen locus", *Science*, Vol. 259, pp. 1904–1907 (1993).

Szpirer et al., 1994. The genes encoding the glutamate receptor subunits KA1 and KA2 (GRIK4 and GRIK5) are located on separate chromosomes in human, mouse and rat. *Proc. Natl. Acad. Sci. USA* 91:11849–11853.

Tagle et al., "Magnetic capture of expressed sequences encoded within large genomic segments" *Nature*, 361:751–753 (1993).

Taylor et al., "Genetic and cellular features of ataxia telangiectasia" *Int. J. Radiat. Biol.* 65:65–70 (1994).

Taylor et al., Variant forms of ataxia telangiectasia. J. Med. Genet. 24, 669–677 (1987).

The European Polycystic Kidney Disease Consortium, "The polycystic kidney disease 1 gene encodes a 14 kb transcript and lies within a duplicated region on chromosome 16" *Cell*, 77:881–894 (1994).

The Huntington's Disease Collaborative Research Group, "A novel gene containing a trinucleotide repeat that is expanded and unstable on Huntington's disease chromosomes" *Cell*, 72:971–983 (1993).

Thomas et al., 1991. Phosphorylation of c-Src on tyrosine 527 by anchor protein tyrosine kinase. Science 254:568–571.

Trofatter et al., "A novel moesin-, ezrin-, radixin-like gene is a candidate for the neurofibromatosis 2 tumor suppressor" *Cell*, 72:791–800 (1993).

Vanagaite et al., "Physical localization of microsatellite markers at the ataxia-telangiectasia locus at 11q22-23. *Genomics*, 22:231–233 (1994a).

Vanagaite et al., "High-density microsatellite map of ataxia-telangiectasia locus" *Human Genetics* 95:451–453 (1995).

Vetrie et al., "The gene involved in X-linked agammaglobulinemia is a member of the src family of protein-tyrosine kinases" *Nature*, 361:226–233 (1993).

Weber and May, "Abundant class of human DNA polymorphisms which can be typed using the polymerase chain reaction" *Am. J. Hum. Genet.*, 44:388–396 (1989).

Weemaes et al., "Nijmegen breakage syndrome: A progress report" *Int. J. Radiat. Biol.* 66:S185–S188 (1994).

Ying and Decoteau, "Cytogenetic anomalies in a patient with ataxia, immune deficiency, and high alpha-fetoprotein in the absence of telangiectasia" *Cancer Genet. Cytogenet.* 4:311–317 (1983).

Zakian, "ATM-related genes: What do they tell us about functions of the human gene?" *Cell* 82:685–687 (1995).

Ziv et al., "Ataxia-telangiectasia: linkage analysis in highly inbred Arab and Druze families and differentiation from an ataxia-microcephaly-cataract syndrome" *Hum. Genet.*, 88:619–626 (1992).

Ziv et al., "The ATC (ataxia-telangiectasia complementation group C) locus localizes to 11q22-q23. *Genomics*, 9:373–375 (1991).

Ziv et al., "Ataxia telangiectasia: a variant with altered in vitro phenotype of fibroblast cells" *Mutation Res.* 210:211–219 (1989).

What is claimed is:

1. A purified amino acid sequence selected from the group consisting of SEQ ID No:3 and analogs thereof and mutations of SEQ ID No:3 which cause ataxia-telangiectasia.

2. The purified amino acid sequence as set forth in claim 1 having signal transduction activity.

3. The purified amino acid sequence as set forth in claim 1 wherein said amino acid sequence codes for the protein phosphatidylinositol 3-kinase.

4. A peptide amino acid sequence isolated from the amino acid sequence as set forth in claim 1 having immunogenic properties.

5. A purified amino acid sequence as set forth in SEQ ID No:3 and analogs thereof.

\* \* \* \* \*